US012577211B2

(12) United States Patent
Murphy et al.

(10) Patent No.: US 12,577,211 B2
(45) Date of Patent: Mar. 17, 2026

(54) PROBENECID COMPOUNDS FOR THE TREATMENT OF INFLAMMASOME-MEDIATED LUNG DISEASE

(71) Applicant: Bacainn Biotherapeutics, Ltd., George Town (KY)

(72) Inventors: Chris Murphy, Upton, MA (US); Ronald Farquhar, Boston, MA (US); Roland E. Dolle, Eureka, MO (US); Manuel Navia, Lexington, MA (US)

(73) Assignee: Bacainn Biotherapeutics, Ltd., George Town (KY)

( * ) Notice: Subject to any disclaimer, the term of this patent is extended or adjusted under 35 U.S.C. 154(b) by 553 days.

(21) Appl. No.: 18/013,355

(22) PCT Filed: Jun. 24, 2021

(86) PCT No.: PCT/US2021/038994

§ 371 (c)(1),
(2) Date: Dec. 28, 2022

(87) PCT Pub. No.: WO2022/005881

PCT Pub. Date: Jan. 6, 2022

(65) Prior Publication Data

US 2023/0257357 A1 Aug. 17, 2023

Related U.S. Application Data

(60) Provisional application No. 63/045,253, filed on Jun. 29, 2020.

(51) Int. Cl.

| | |
|---|---|
| ***C07D 239/42*** | (2006.01) |
| ***A61P 29/00*** | (2006.01) |
| ***C07C 311/59*** | (2006.01) |
| ***C07D 211/34*** | (2006.01) |
| ***C07D 277/30*** | (2006.01) |

(52) U.S. Cl.

CPC ............ *C07D 239/42* (2013.01); *A61P 29/00* (2018.01); *C07C 311/59* (2013.01); *C07D 211/34* (2013.01); *C07D 277/30* (2013.01)

(58) Field of Classification Search

CPC .................................................... C07D 239/42

See application file for complete search history.

(56) References Cited

U.S. PATENT DOCUMENTS

| | | | | |
|---|---|---|---|---|
| 8,569,017 B2 * | 10/2013 | Ryffel | ................ G01N 33/5308 436/99 |
| 2005/0267152 A1 | 12/2005 | Bloomfield et al. | |

FOREIGN PATENT DOCUMENTS

| | | |
|---|---|---|
| GB | 2 276 161 A | 9/1994 |
| JP | H10-510821 | 10/1998 |
| JP | 2007-530698 A | 11/2007 |
| JP | 2009-534380 | 9/2009 |
| JP | 2010-533185 A | 10/2010 |
| WO | WO-96/19477 | 6/1996 |
| WO | WO-99/36398 A1 | 7/1999 |
| WO | WO-02/06255 A2 | 1/2002 |
| WO | WO-2005/097740 A1 | 10/2005 |
| WO | WO-2007/123516 A1 | 11/2007 |
| WO | WO-2008/124000 A2 | 10/2008 |
| WO | WO-2009/009122 A2 | 1/2009 |
| WO | WO-2010/118367 A2 | 10/2010 |
| WO | WO-2011/145669 A1 | 11/2011 |
| WO | WO-2014/020350 A1 | 2/2014 |
| WO | WO-2015/134790 A1 | 9/2015 |
| WO | WO-2019/014611 A2 | 1/2019 |
| WO | WO-2019/079119 A1 | 4/2019 |
| WO | WO-2019/195753 | 10/2019 |

OTHER PUBLICATIONS

Ryffel et al. CAS: 166:414735, 2016.*
International Search Report and Written Opinion on PCT PCT/US2021/038994 dated Nov. 23, 2021 (10 pages).
Pubchem, Substance Record for SID 403443370, Jan. 24, 2020, Retrieved on Aug. 16, 2021 from https://pubchem.ncbi.nlm.nih.gov/substance/403443370.
Database Registry [Online] Chemical Abstract Service, Columbus, Ohio, US; Oct. 11, 2007 (Oct. 11, 2007) , 4-Piperidinecarboxylic acid, 1-[4-[ (dimethylamino) sulfonyl] phenyl]-11, XP093188780, Database accession No. 950329-66-5.
Database Registry [Online] Chemical Abstract Service, Columbus, Ohio, US; Jun. 20, 2019 (Jun. 20, 2019) , Benzenesulfonamide, N,N-diethyl-4-[[4-(1-oxopropyl)-1-piperazinyl] carbonyl] 11, XP093188941, Database accession No. 2341420-87-7.
Database Registry [Online] Chemical Abstract Service, Columbus, Ohio, US; Dec. 3, 2013 (Dec. 3, 2013) , 4-Oxazolecarboxylic acid, 2-[4-[(dimethylamino) sulfonyl] phenyl]-11, XP093188942, Database accession No. 1485846-63-6.
Database Registry [Online] Chemical Abstract Service, Columbus, Ohio, US; Oct. 30, 2013 (Oct. 30, 2013), Benzenesulfonamide, 4-(4-formyl-1-piperidinyl)-N,N-dimethyl-11, XP093188769, Database accession No. 1466538-86-2.
Database Registry [Online] Chemical Abstract Service, Columbus, Ohio, US; Dec. 1, 2013 (Dec. 1, 2013), Benzenesulfonamide, 4-[4-(2-aminoethyl)-1-piperidinyl]-N,N-dim ethyl-11, XP093188621, Database accession No. 1484376-32-0.
Zhang Xiangna et al: "Development of small molecule inhibitors targeting NLRP3 inflammasome pathway for inflammatory diseases", European Journal of Medicinal Chemistry, Elsevier Masson, vol. 185, Oct. 30, 2019.
CAS Registry No. "294885-74-8 ", STN, CAS American Chemical Society.

(Continued)

*Primary Examiner* — Rei Tsang Shiao
(74) *Attorney, Agent, or Firm* — Foley & Lardner LLP

(57) ABSTRACT

Disclosed herein are methods, compounds, and compositions for treating or preventing inflammasome-mediated diseases or conditions, including inflammasome-mediated lung diseases or conditions.

29 Claims, 20 Drawing Sheets

(56) References Cited

OTHER PUBLICATIONS

Abd El-Gilil, S. M., "Design, synthesis, molecular docking and biological screening of N-ethyl-N-methylbenzenesulfonamide derivatives as effective antimicrobial and antiproliferative agents", Journal of Molecular Structure, 2019, vol. 1194, pp. 144 to 156, DOI: 10.1016/j.molstruc. 2019. 04. 048.

Bashandy, M. S., "1-(4-(Pyrrolidin-1-ylsulfonyl)phenyl) ethanone in Heterocyclic Synthesis: Synthesis, Molecular Docking and Anti-Human Liver Cancer Evaluation of Novel Sulfonamides Incorporating Thiazole, Imidazo[1,2-a]pyridine, Imidazo[2, 1-c][1,2,4]triazole, Imidazo[2, 1-b]thiazole, 1,3,4-Thiadiazine and 1,4-Thiazine Moieties", International Journal of Organic Chemistry, 2015, vol. 05, No. 03, pp. 166 to 190, DOI: 10.4236/ijoc.2015.53018.

Bheeter, C. B. et al., "Palladium-catalysed direct heteroarylation of bromobenzenes bearing S02R substituents at C2 or C4", RSC Advances, 2013, vol. 3, No. 17, pp. 5987 to 5996, DOI: 10.1039/c3ra40769a.

CAS Registry No. 1485846-63-6, etc., Database Registry (online), 2013 (search date: Apr. 10, 2025).

Hanke et al (2013) Synthesis and pharmacological characterization of benzenesulfonamides as dual species inhibitors of human and murine mPGES-1.

Hughes, J. M. E. et al., "Desulfonylative Arylation of Redox-Active Alkyl Sulfones with Aryl Bromides", Organic Letters, 2019, vol. 21, No. 14, pp. 5650 to 5654, DOI: 10.1021/acs.orglett.9b01987.

Knochel, P. et al., "Nickel-Catalyzed Cross-Coupling Reactions of Aryltitanium (IV) Alkoxides with Aryl Halides", Synlett, 2007, vol. 2007, No. 13, pp. 2077 to 2080, DOI: 10.1055/s-2007-984906.

Liu, C. et al., "Synthesis of Biaryls via Decarbonylative Palladium-Catalyzed Suzuki-Miyaura Cross-Coupling of Carboxylic Acids", iScience, 2019, vol. 19, pp. 749 to 759, DOI: 10.1016/j.isci.2019.08.021.

Malapit, C. A. et al., "Base-free nickel-catalysed decarbonylative Suzuki-Miyaura coupling of acid fluorides", Nature, 2018, vol. 563, No. 7729, pp. 100 to 104, DOI: 10.1038/s41586-018-0628-7.

Sabatka, J. J. et al., ”Measurement of lipophilicity by high-performance liquid chromatography”, Journal of Chromatography A, 1987, vol. 384, pp. 349 to 356, DOI: 10.1016/S0021-9673(01)94682-5.

Tang, J. et al., "Catalytic Decarboxylative Cross-Coupling of Aryl Chlorides and Benzoates without Activating ortho Substituents", Angewandte Chemie International Edition, 2015, vol. 54, No. 44, pp. 13130 to 13133, DOI: 10.1002/anie.201505843.

* cited by examiner

FIGURE 9A
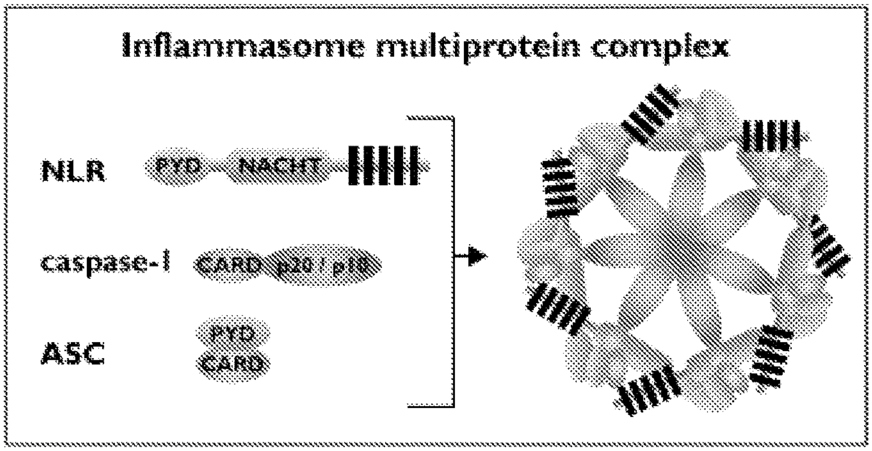
FIGURE 9B
NS
FIGURE 9C
Nigericin
FIGURE 9D
Nigericin/BT032 (350 uM)
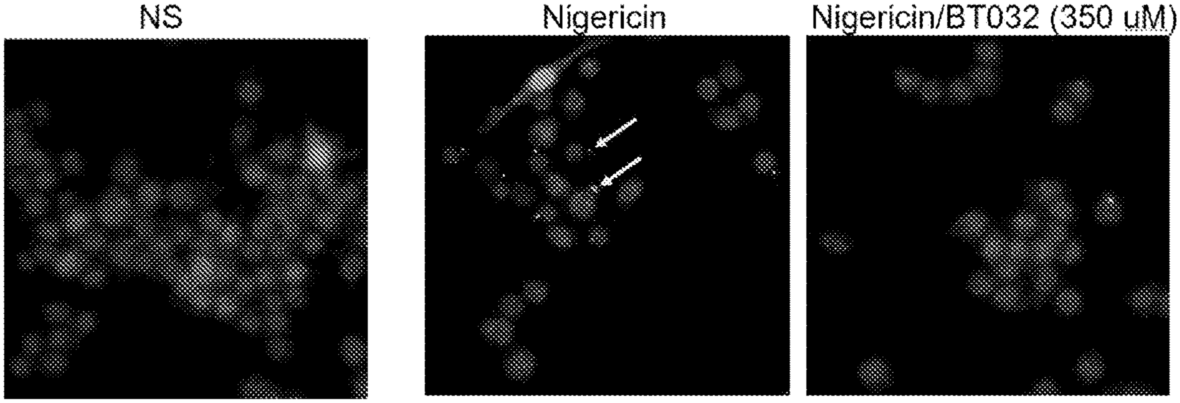

PROBENECID COMPOUNDS FOR THE TREATMENT OF INFLAMMASOME-MEDIATED LUNG DISEASE

CROSS-REFERENCE TO RELATED APPLICATION

The present application claims priority to U.S. Provisional Patent Application No. 63/045,253, filed on Jun. 29, 2020, the contents of which are hereby incorporated by reference in their entirety.

TECHNICAL FIELD

The technology of the present disclosure relates generally to methods, compounds, and compositions for treating or preventing inflammasome-mediated diseases or conditions, including inflammasome-mediated lung diseases or conditions.

BACKGROUND

Inflammation is an adaptive response to noxious stimuli. Innate immunity comprises a system of germline-encoded receptors that inspect the intracellular and extracellular compartments for signs of infection and recognize highly conserved microbial motifs or pathogen-associated molecular patterns (PAMPs). These pattern-recognition receptors (PRRs) are expressed by host infection defense cells, such as macrophages, monocytes, dendritic cells, and epithelial cells. Membrane-bound Toll-like receptors (TLRs) and C-type lectins are the PRRs that probe the extracellular milieu and the endosomal compartments for PAMPs, while the cytosol is scanned by intracellular nucleic acid sensors, such as interferon-inducible protein (also known as AIM2) and retinoic acid-inducible gene-like helicases. Activation of these receptors causes proinflammatory cytokine production and type I interferon-dependent antiviral responses via the transcription factor NF-κB.

Nucleotide oligomerization domain (NOD)-like receptors (NLRs) are a type of intracellular PRR that recognize PAMPs and the host-derived signals, DAMPS (danger-associated molecular patterns). NLRs are composed of a conserved central domain, which mediates nucleotide binding and oligomerization, a COOH-terminal leucine-rich domain (LRR), which senses NLR agonists and has an autoinhibitory effect in their absence, and an $NH_2$-terminal region, which is required for protein-protein interaction. The human NLR gene family is composed of 22 members, which, depending on their $NH_2$-terminal domains, are classified into four subfamilies: NLRA, NLRB, NLRC, and NLRP. Activation of certain NLRs (NLRP1 (NACHT, LRR and PYD domains-containing protein 1), NLRP3 (NACHT, LRR and PYD domains-containing protein 3), and NLRC4 (NLR family CARD domain-containing protein 4)) leads to assembly of the inflammasome. The inflammasome is an intracellular multimeric protein complex that regulates the maturation and release of proinflammatory cytokines of the IL-1 family (e.g., IL-1β and IL-18) in response to pathogens and endogenous danger signals. Growing evidence indicates that the inflammasome plays a key role in the pathogenesis of acute and chronic respiratory diseases. Hence, there is a need to develop improved techniques for treating such disorders related to inflammasome activity.

SUMMARY

In one aspect, the present disclosure provides a compound having the structure of Formula I,

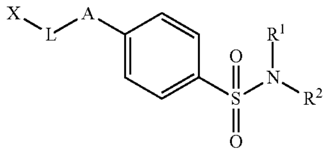

I tautomers thereof and/or pharmaceutically acceptable salts thereof;

wherein

A is absent, or is selected from the group consisting of $C(O)N(R^3)$, phenylene, oxazolylene, thiazolylene, piperidinylene, and

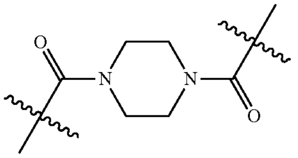

;

L is absent or $C_{1-10}$ alkylene;

X is H, CHO, COOH, $C(O)NR^4R^5$, $COOR^6$, $NH_2$ or NHR;

R is 2-chloropyrimidin-4-yl;

$R^1$ and $R^2$ are independently a substituted or unsubstituted $C_{1-6}$ alkyl group, or one of $R^1$ and $R^2$ is H, and the other is cyclohexyl-NH—C(O), or $R^1$ and $R^2$ together are a $C_{4-6}$ alkylene group and form a 5-, 6-, or 7-member ring with the nitrogen to which they are attached, said ring optionally substituted with a phenyl group;

$R^3$ and $R^4$ are independently selected from H or a $C_{1-6}$ alkyl group;

$R^5$ is selected from H, PEG, or a $C_{1-6}$ alkyl group; and $R^6$ is selected from a substituted or unsubstituted $C_{1-10}$ alkyl, $C_{2-10}$ alkenyl, or $C_{7-14}$ aralkyl group.

In some embodiments, A is absent. In some embodiments, A is $C(O)N(R^3)$. In some such embodiments, N is attached to L or X. In other such embodiments, C is attached to L or X. In some embodiments, $R^3$ $C_{1-6}$ alkyl, and in some embodiments, $R^3$ is H or methyl. In some embodiments, A is phenylene, oxazolylene, thiazolylene, piperidinylene or

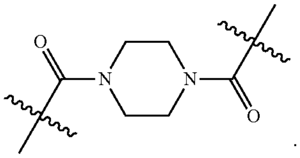 [SMILES: *C(=O)N1CCN(C(*)=O)CC1]

.

In some embodiments, A is phenylene, oxazolylene, thiazolylene, or piperidinylene.

In some embodiments, L is absent. In some embodiments, L is a $C_{1-10}$ alkylene.

In some embodiments, X is H. In some embodiments, X is COOH. In some embodiments, X is $C(O)NR^4R^5$. In some embodiments, X is $COOR^6$. In some embodiments, X is $NH_2$ or NHR.

In some embodiments, each of $R^1$ and $R^2$ is independently a $C_{1-6}$ alkyl, optionally substituted with one or more F, OH, $CF_3$, $C_{3-7}$ cycloalkyl group or $SO_2$-alkyl. In some embodiments, $R^1$ and $R^2$ together are a $C_{4-6}$ alkylene group and form a 5-, 6-, or 7-member ring with the nitrogen to which they are attached. In some embodiments, one of $R^1$ and $R^2$ is H, and the other is cyclohexyl-NH—C(O).

In some embodiments, A is absent, or is selected from the group consisting of $C(O)N(R^3)$, phenylene, oxazolylene, thiazolylene, and piperidinylene; L is absent or $C_{1-10}$ alkylene; X is H, COOH, or $NH_2$; $R^1$ and $R^2$ are independently a substituted or unsubstituted $C_{1-6}$ alkyl group; and $R^3$ is selected from H or a $C_{1-6}$ alkyl group.

In some embodiments, A is absent and L is $C_{3-10}$ alkylene. In some embodiments, A is phenylene, oxazolylene, thiazolylene, or piperidinylene, and L is absent or a $C_{1-5}$ alkylene.

In some embodiments, the compound, tautomer thereof, and/or the pharmaceutically acceptable salt thereof is selected from the group consisting of

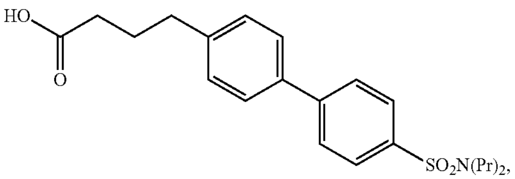

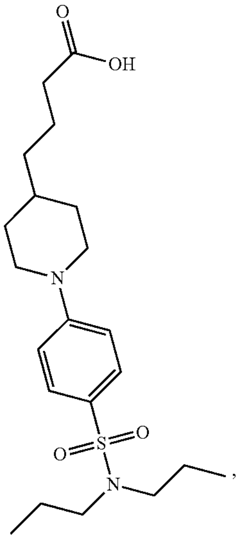
,
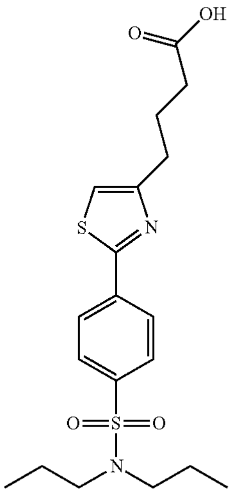
,
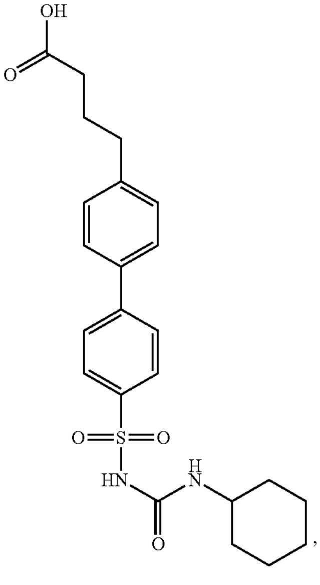
, and

-continued

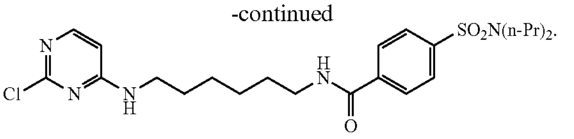

In some embodiments, the present disclosure relates to a pharmaceutical composition comprising the compound, tautomer thereof and/or pharmaceutically acceptable salt thereof and a pharmaceutically acceptable carrier.

In one aspect, the present disclosure relates to a method for treating or preventing an inflammasome-mediated disease or condition in a mammalian subject in need thereof, comprising administering to the subject a therapeutically effective amount of a compound of the present technology, tautomer thereof, and/or pharmaceutically acceptable salt thereof, or a pharmaceutical composition comprising the compound and a pharmaceutically acceptable carrier.

In some embodiments, the inflammasome-mediated disease or condition is associated with NLRP1 inflammasome activation and/or NLRP3 inflammasome activation.

In some embodiments, the inflammasome-mediated disease or condition is an inflammasome-mediated lung disease or condition.

In some embodiments, the compound, tautomer thereof, and/or pharmaceutically acceptable salt or the pharmaceutical composition comprises:

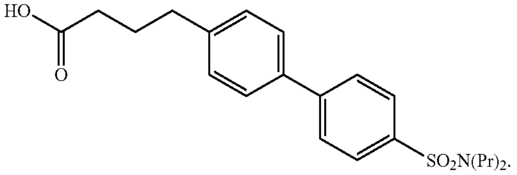

In some embodiments, the compound, tautomer thereof, and/or pharmaceutically acceptable salt or the pharmaceutical composition comprises:

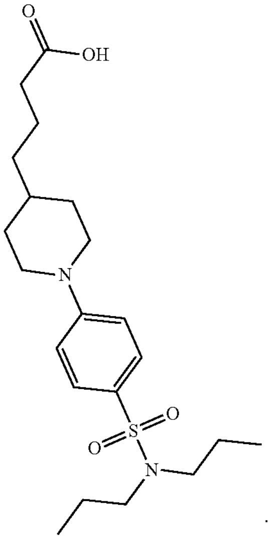 [SMILES: CCCN(CCC)S(=O)(=O)c1ccc(N2CCC(CCCC(=O)O)CC2)cc1]

In some embodiments, the compound, tautomer thereof, and/or pharmaceutically acceptable salt or the pharmaceutical composition comprises:

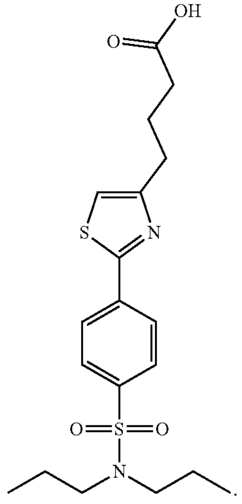 [SMILES: CCCN(CCC)S(=O)(=O)c1ccc(-c2nc(CCCC(=O)O)cs2)cc1]

In some embodiments, the compound, tautomer thereof, and/or pharmaceutically acceptable salt or the pharmaceutical composition comprises:

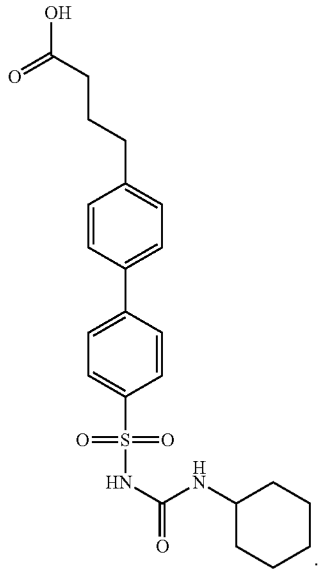 [SMILES: O=C(O)CCCc1ccc(-c2ccc(S(=O)(=O)NC(=O)NC3CCCCC3)cc2)cc1]

In some embodiments, the compound, tautomer thereof, and/or pharmaceutically acceptable salt or the pharmaceutical composition comprises:

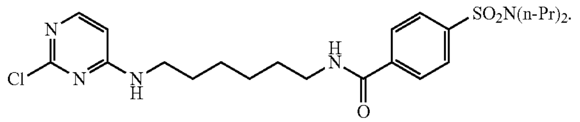

In some embodiments, the inflammasome-mediated lung disease or condition is/is caused by a pathogen selected from the group consisting of: pandemic influenza; *Streptococcus pneumonia; Pseudomonas aeruginosa; Mycobacterium tuberculosis*; respiratory syndromes caused by rhinovirus, Flaviviruses, Dengue virus, Zika virus, or West Nile virus; idiopathic pulmonary fibrosis (IPF); chronic obstructive pulmonary disease (COPD); acute exacerbations of COPD (AECOPD); asthma; acute respiratory distress syndrome (ARDS); COVID-19; Middle East Respiratory Syndrome (MERS); Severe Acute Respiratory Syndrome (SARS); silicosis; and asbestosis.

In some embodiments, the inflammasome-mediated lung disease or condition is associated with inhalation of an irritant. In some embodiments, the inhaled irritant comprises a gas, a mist, a fume, or a dust. In some embodiments, the inhaled irritant is selected from the group consisting of silica, asbestos, smoke, cigarette smoke, nanoparticles.

In some embodiments, the administering step is selected from the group consisting of intranasal administration, intramuscular administration, subcutaneous administration, administration by inhalation, and oral administration.

In some embodiments, the treating or preventing inflammasome-mediated disease or condition comprises reducing the level of one or more inflammatory cytokines in the subject as compared to an untreated control subject.

In some embodiments, the one or more inflammatory cytokines is selected from the group consisting of IL-1β, IL-18, IL-1α, IL-6, IL-33, TNF-α, CCL2, IFN-γ, IL-10, IL12p70, MCP-1, HMGB1, and any combination thereof. In some embodiments, the one or more inflammatory cytokines is IL-1β.

In some embodiments, the treating or preventing inflammasome-mediated lung disease or condition comprises reducing cellular infiltrate levels in the lungs of the subject as compared to an untreated control subject, wherein the cellular infiltrates comprise one or more of alveolar macrophages, neutrophils, inflammatory $Ly6C^+$ macrophages, and dendritic cells.

In some embodiments, the treating or preventing inflammasome-mediated disease or condition comprises reducing apoptosis-associated speck-like protein containing a caspase activating and recruitment domain (ASC) speck formation in the subject as compared to an untreated control subject.

In one aspect, the present disclosure relates to a use of a composition in the preparation of a medicament for treating or preventing an inflammasome-mediated disease or condition in a subject in need thereof, wherein the composition comprises a therapeutically effective amount of a compound of the present technology, tautomer thereof, and/or pharmaceutically acceptable salt thereof, or a pharmaceutical composition comprising the compound and a pharmaceutically acceptable carrier.

In some embodiments, the inflammasome-mediated disease or condition is associated with NLRP1 inflammasome activation and/or NLRP3 inflammasome activation.

In some embodiments, the inflammasome-mediated disease or condition is an inflammasome-mediated lung disease or condition.

In some embodiments, the compound, tautomer thereof, and/or pharmaceutically acceptable salt or the pharmaceutical composition comprises:

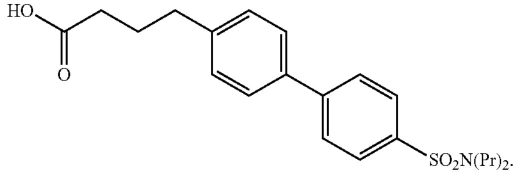

In some embodiments, the compound, tautomer thereof, and/or pharmaceutically acceptable salt or the pharmaceutical composition comprises:

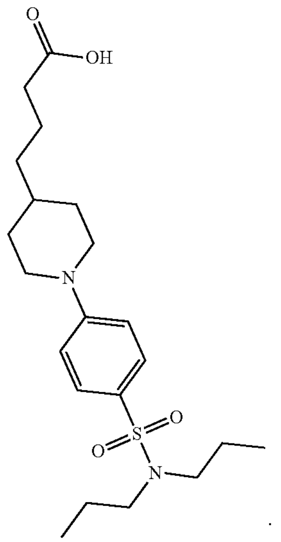 [SMILES: CCCN(CCC)S(=O)(=O)c1ccc(N2CCC(CCCC(=O)O)CC2)cc1]

In some embodiments, the compound, tautomer thereof, and/or pharmaceutically acceptable salt or the pharmaceutical composition comprises:

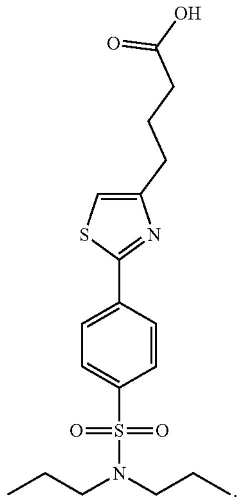 [SMILES: CCCN(CCC)S(=O)(=O)c1ccc(-c2nc(CCCC(=O)O)cs2)cc1]

In some embodiments, the compound, tautomer thereof, and/or pharmaceutically acceptable salt or the pharmaceutical composition comprises:

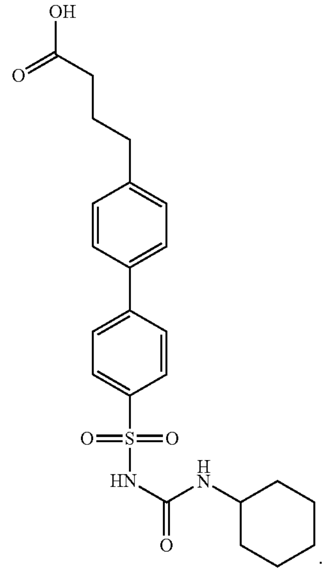 [SMILES: O=C(O)CCCc1ccc(-c2ccc(S(=O)(=O)NC(=O)NC3CCCCC3)cc2)cc1]

In some embodiments, the compound, tautomer thereof, and/or pharmaceutically acceptable salt or the pharmaceutical composition comprises:

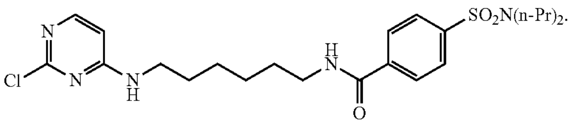

In some embodiments, the inflammasome-mediated lung disease or condition is/is caused by a pathogen selected from the group consisting of: pandemic influenza; *Streptococcus pneumonia; Pseudomonas aeruginosa; Mycobacterium tuberculosis*; respiratory syndromes caused by rhinovirus, Flaviviruses, Dengue virus, Zika virus, or West Nile virus; idiopathic pulmonary fibrosis (IPF); chronic obstructive pulmonary disease (COPD); acute exacerbations of COPD (AECOPD); asthma; acute respiratory distress syndrome (ARDS); COVID-19; Middle East Respiratory Syndrome (MERS); Severe Acute Respiratory Syndrome (SARS); silicosis; and asbestosis.

In some embodiments, the inflammasome-mediated lung disease or condition is associated with inhalation of an irritant. In some embodiments, the inhaled irritant comprises a gas, a mist, a fume, or a dust. In some embodiments, the inhaled irritant is selected from the group consisting of silica, asbestos, smoke, cigarette smoke, nanoparticles.

In some embodiments, the administering step is selected from the group consisting of intranasal administration, intramuscular administration, subcutaneous administration, administration by inhalation, and oral administration.

In some embodiments, the treating or preventing inflammasome-mediated disease or condition comprises reducing the level of one or more inflammatory cytokines in the subject as compared to an untreated control subject.

In some embodiments, the one or more inflammatory cytokines is selected from the group consisting of IL-1β, IL-18, IL-1α, IL-6, IL-33, TNF-α, CCL2, IFN-γ, IL-10, IL12p70, MCP-1, HMGB1, and any combination thereof. In some embodiments, the one or more inflammatory cytokines is IL-1β.

In some embodiments, the treating or preventing inflammasome-mediated lung disease or condition comprises reducing cellular infiltrate levels in the lungs of the subject as compared to an untreated control subject, wherein the cellular infiltrates comprise one or more of alveolar macrophages, neutrophils, inflammatory Ly6C+ macrophages, and dendritic cells.

In some embodiments, the treating or preventing inflammasome-mediated disease or condition comprises reducing apoptosis-associated speck-like protein containing a caspase activating and recruitment domain (ASC) speck formation in the subject as compared to an untreated control subject.

In one aspect, the present disclosure relates to a compound of the present technology, tautomer thereof, and/or pharmaceutically acceptable salt thereof, or a pharmaceutical composition comprising the compound and a pharmaceutically acceptable carrier, for use in treating or preventing an inflammasome-mediated disease or condition in a subject in need thereof.

In some embodiments, the inflammasome-mediated disease or condition is associated with NLRP1 inflammasome activation and/or NLRP3 inflammasome activation.

In some embodiments, the inflammasome-mediated disease or condition is an inflammasome-mediated lung disease or condition.

In some embodiments, the compound, tautomer thereof, and/or pharmaceutically acceptable salt or the pharmaceutical composition comprises:

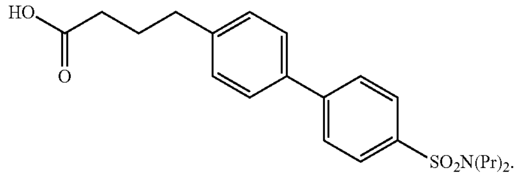

In some embodiments, the compound, tautomer thereof, and/or pharmaceutically acceptable salt or the pharmaceutical composition comprises:

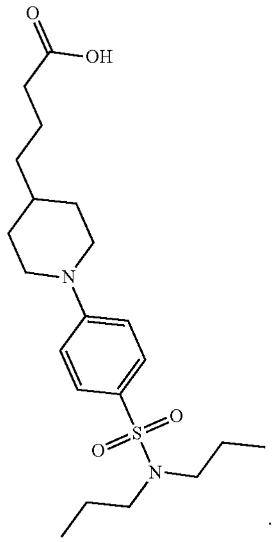 [SMILES: CCCN(CCC)S(=O)(=O)c1ccc(N2CCC(CCCC(=O)O)CC2)cc1]

In some embodiments, the compound, tautomer thereof, and/or pharmaceutically acceptable salt or the pharmaceutical composition comprises:

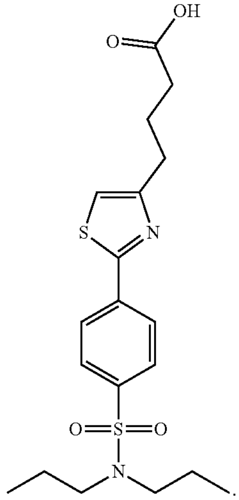 [SMILES: CCCN(CCC)S(=O)(=O)c1ccc(-c2nc(CCCC(=O)O)cs2)cc1]

In some embodiments, the compound, tautomer thereof, and/or pharmaceutically acceptable salt or the pharmaceutical composition comprises:

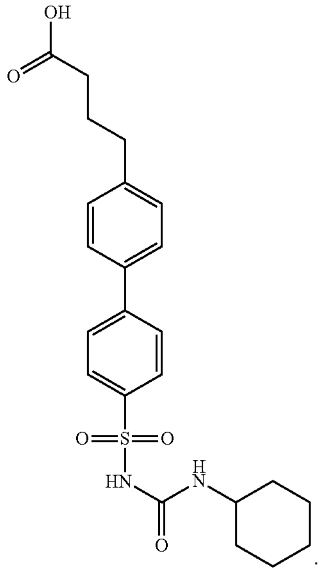 [SMILES: O=C(O)CCCc1ccc(-c2ccc(S(=O)(=O)NC(=O)NC3CCCCC3)cc2)cc1]

In some embodiments, the compound, tautomer thereof, and/or pharmaceutically acceptable salt or the pharmaceutical composition comprises:

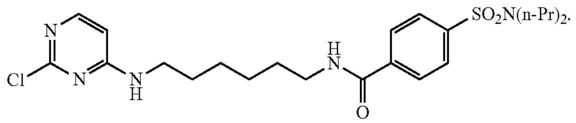

In some embodiments, the inflammasome-mediated lung disease or condition is/is caused by a pathogen selected from the group consisting of: pandemic influenza; *Streptococcus pneumonia; Pseudomonas aeruginosa; Mycobacterium tuberculosis*; respiratory syndromes caused by rhinovirus, Flaviviruses, Dengue virus, Zika virus, or West Nile virus; idiopathic pulmonary fibrosis (IPF); chronic obstructive pulmonary disease (COPD); acute exacerbations of COPD (AECOPD); asthma; acute respiratory distress syndrome (ARDS); COVID-19; Middle East Respiratory Syndrome (MERS); Severe Acute Respiratory Syndrome (SARS); silicosis; and asbestosis.

In some embodiments, the inflammasome-mediated lung disease or condition is associated with inhalation of an irritant. In some embodiments, the inhaled irritant comprises a gas, a mist, a fume, or a dust. In some embodiments, the inhaled irritant is selected from the group consisting of silica, asbestos, smoke, cigarette smoke, nanoparticles.

In some embodiments, the administering step is selected from the group consisting of intranasal administration, intramuscular administration, subcutaneous administration, administration by inhalation, and oral administration.

In some embodiments, the treating or preventing inflammasome-mediated disease or condition comprises reducing the level of one or more inflammatory cytokines in the subject as compared to an untreated control subject.

In some embodiments, the one or more inflammatory cytokines is selected from the group consisting of IL-1β, IL-18, IL-1α, IL-6, IL-33, TNF-α, CCL2, IFN-γ, IL-10, IL12p70, MCP-1, HMGB1, and any combination thereof. In some embodiments, the one or more inflammatory cytokines is IL-1β.

In some embodiments, the treating or preventing inflammasome-mediated lung disease or condition comprises reducing cellular infiltrate levels in the lungs of the subject as compared to an untreated control subject, wherein the cellular infiltrates comprise one or more of alveolar macrophages, neutrophils, inflammatory $Ly6C^+$ macrophages, and dendritic cells.

In some embodiments, the treating or preventing inflammasome-mediated disease or condition comprises reducing apoptosis-associated speck-like protein containing a caspase activating and recruitment domain (ASC) speck formation in the subject as compared to an untreated control subject.

BRIEF DESCRIPTION OF THE DRAWINGS

FIG. 9A is a schematic showing an inflammasome multiprotein complex (adapted from Review InvivoGen, Inflammasomes, available at www.invivogen.com/review-inflammasome (2021)). In this illustrative inflammasome, the inflammasome complex contains a Nod-like receptor (NLR), the adapter apoptosis-associated speck-like (ASC) protein, and Caspase-1. As shown in this illustrative example of an inflammasome multiprotein complex, the NLR portion contains a pyrin domain (PYD) and nucleotide-binding and oligomerization domain (NACHT); the Caspase-1 portion contains a caspase recruitment domain (CARD) and p20 and p10 subunits; the ASC portion contains a PYD and CARD.

FIGS. 9B-9D are pictures showing the ability of probenecid analogs of the present technology (e.g., BT032) to inhibit the formation of the inflammasome complex following NLRP3 activation. NLRP3-deficient immortalized BMDMs reconstituted with ASC-cerulean (pseudocolor RED) and NLRP3-Flag were either not stimulated (FIG. 9B) or stimulated with NLRP3 agonist nigericin (3 μM) for 90 mins (FIG. 9C). ASC-cerulean macrophages were also pretreated with BT032 (350 μM) for 60 mins prior to nigericin challenge (FIG. 9D). Macrophages were fixed with 4% paraformaldehyde and imaged for the formation of inflammasome specks as identified by intense, punctate staining in the cytosol of cells. Cell nuclei were stained with DAP (4',6'-diamidino-2-phenylindole; BLUE). Representative images shown are maximum intensity projections of 3D deconvoluted z stacks using ImageJ.

DETAILED DESCRIPTION

I. Definitions

Figure 1:
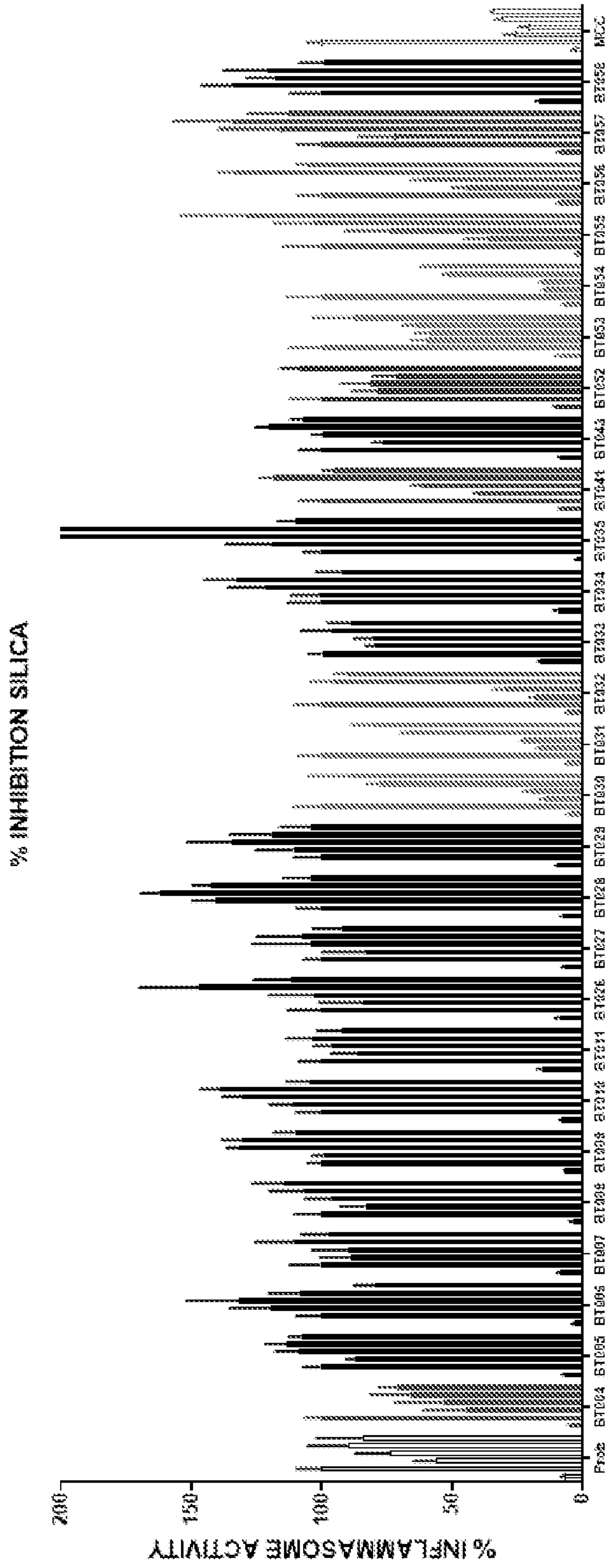
FIG. 1 is a chart showing the dose-response of probenecid analogs on the inhibition of inflammasome activity as assessed by secreted IL-1β ELISA in macrophages pre-activated with lipopolysaccharide (LPS; 100 ng/mL). The macrophages were stimulated with the NLRP3 activator, silica (250 μg/mL). From left to right: the first bar for each compound is non-silica activated; the second bar is silica activated but no compound; the following bars are with the compound at 300 μM, 150 μM, 30 μM, and 3 μM. Prob=probenecid; MCC=MCC950, a specific small molecule inhibitor of NLRP3 inflammasome. From left to right, the compounds listed on the x-axis are as follows: Prob, BT004, BT005, BT006, BT007, BT008, BT009, BT010, BT011, BT026, BT027, BT028, BT029, BT030, BT031, BT032, BT033, BT034, BT035, BT041, BT043, BT052, BT053, BT054, BT055, BT056, BT057, BT058, MCC.

The following terms are used herein, the definitions of which are provided for guidance.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. It will be understood by those of skill in the art that substituted groups of the present technology are chemically stable groups that allow isolation of the compounds in which they appear. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; sulfonamides; amines; N-oxides; azides; amides; ureas; amidines; guanidines; nitro groups; nitriles (i.e., CN); and the like.

Alkyl groups include straight chain and branched chain alkyl groups having (unless indicated otherwise) from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. In some embodiments the alkyl group is substituted with 1, 2, or 3 substituents.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $—CH{=}CH(CH_3)$, $—CH{=}C(CH_3)_2$, $—C(CH_3){=}CH_2$, $—C(CH_3){=}CH(CH_3)$, $—C(CH_2CH_3){=}CH_2$, among others. Representative substituted alkenyl groups may be mono-substituted or substituted more than once, such as, but not limited to, mono-, di- or tri-substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heteroalkyl groups and heteroalkenyl groups are, respectively, alkyl groups (as defined herein) and alkenyl groups (as defined herein) that include from 1 to 6 heteroatoms selected from N, O and S. It will be understood that each heteroatom present is bonded to at least one carbon atom within the heteroalkyl or heteroalkenyl group. In some embodiments the heteroalkyl or heteroalkenyl groups include 1, 2, or 3 heteroatoms. Heteroalkyl and heteroalkenyl groups may be substituted or unsubstituted. Examples of heteroalkyl groups include but are not limited to $CH_3CH_2OCH_2$, $CH_3NHCH_2$, $CH_3CH_2N(CH_3)CH_2$, $CH_3CH_2SCH_2$, $CH_3CH_2OCH_2CH_2OCH_2CH_2$. Examples of heteroalkenyl groups include but are not limited to $CH_2{=}CHOCH_2$, $CH_2{=}CHN(CH_3)CH_2$, and $CH_2{=}CHSCH_2$. Representative substituted heteroalkyl or heteroalkenyl groups may be substituted one or more times with substituents such as those listed above (e.g., 1, 2 or 3 times), and include without limitation haloheteroalkyl (e.g., trifluoromethyloxyethyl), carboxyalkylaminoalkyl, methyl acrylate and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent cycloalkyl groups are cycloalkylene groups, divalent heteroalkyl groups are heteroalkylene groups, divalent alkenyl groups are alkenylene groups, and so forth. Substituted groups having a single point of attachment to the compound of the present technology are not referred to with the "ene" designation. Thus, e.g., chloroethyl is not referred to herein as chloroethylene.

The term "administering" a molecule to a subject means delivering the molecule to the subject or cells. "Administering" includes prophylactic administration of the composition (i.e., before the disease and/or one or more symptoms of the disease are detectable) and/or therapeutic administration of the composition (i.e., after the disease and/or one or more symptoms of the disease are detectable). The methods of the present technology include administering one or more compounds. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

Use of the terms "comprising", "including" or similar terms to describe or define an embodiment of a compound, composition or method having one or more elements shall be understood to also disclose embodiments "consisting" or "consisting essentially" of the elements and vice versa. In other words, disclosure of embodiments open to elements beyond those listed ("comprising"), also are to be understood to disclose embodiments which are closed to additional elements ("consisting") or which may only include additional elements that do not materially affect the characteristics of the embodiment ("consisting essentially"). Likewise, embodiments consisting or consisting essentially of the listed elements shall be understood to disclose embodiments comprising those elements.

The term "conjugating," and grammatical equivalents, when made in reference to conjugating a molecule of interest and a polymer means covalently linking the molecule of interest to the polymer. Linkage may be direct. Alternatively, linkage may be indirect via a linking group or moiety. Methods for conjugation to polymers are known in the art, including methods for conjugation to a polypeptide to produce a fusion protein (Pasut, *Polymers* 6:160-178 (2014); Medscape, *Nanomedicine* 5(6):915-935 (2010)). In some embodiments, the conjugate comprises probenecid conjugated to a PEG polymer.

As used herein, the terms "effective amount" or "therapeutically effective amount," or "pharmaceutically effective amount" refer to a quantity sufficient to achieve a desired therapeutic and/or prophylactic effect, e.g., an amount which results in the full or partial amelioration of inflammasome-mediated lung disease or symptoms associated with inflammasome-mediated lung disease in a subject in need thereof. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In some embodiments, multiple doses are administered. Additionally or alternatively, in some embodiments, multiple therapeutic compositions or compounds are administered. In the methods described herein, the therapeutic compounds may be administered to a subject having one or more signs or symptoms of an inflammasome-mediated lung disease (e.g., elevated pulmonary concentrations of inflammatory cytokines, such as IL-1β or IL-18).

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

"Polymer" is a substance that has a molecular structure consisting chiefly or entirely of a large number of similar units bonded together. Polymers may occur naturally (e.g., cellulose, polypeptides, nucleotides sequences, etc.) or are artificial (e.g., plastics, resins, etc.). Polymers may be used as carriers of drugs to which they are conjugated (i.e., a polymer carrier), and may enhance the solubility of the conjugated drug, improve its pharmacokinetic profile, protect the drug against degradation, release the drug under certain conditions, such as change in pH or in the presence of enzymes, such as esterases, lipases or proteases. In addition, a targeting moiety or a solubilizer may also be introduced into the conjugate to boost its therapeutic index (Medscape, *Nanomedicine* 5(6):915-935(2010)). Polymers (including polymeric carriers) may also be utilized to restrict the distribution of the drug conjugated to it by, for example, preventing the conjugated drug from crossing into specific body compartments (e.g., from the gastrointestinal lumen to the underlying tissue). Polymers (including polymer carriers) are pharmaceutically acceptable and may be natural polymers and/or synthetic linear polymers, and include polyethylene glycol (PEG), dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly(hydroxyalkylmethaacrylamide), polyglycerol, 25 polyamidoamine (PAMAM), polyethylenimine (PEI), and polypeptides.

As used herein, "inflammasome activation" means that an inflammasome is formed by association of a pattern recognition receptor such as NLRP3 with apoptosis associated speck-like protein containing a CARD (ASC) and a caspase-1 precursor due to a stimulating factor such as pathogen components and that caspase-1 is activated. Caspase-1 cleaves the pro-inflammatory cytokines IL-1β and IL-18 to their active forms and mediates a type of inflammatory cell death known as pyroptosis. Other intracellular pattern recognition receptors (PRRs), such as NLR family members, NLRP1 and NLRC4, non-NLR PRRs such as the double-stranded DNA (dsDNA) sensors absent in melanoma 2 (AIM2) and interferon-gamma-inducible protein 16 (IFI16), are also capable of forming inflammasomes. The probenecid analogs of the present technology may inhibit inflammasome activation and thus inhibit the production of activated caspase-1. As a result, the probenecid analogs of the present technology may inhibit the release of one or more inflammatory cytokines such as IL-1β, IL-18, IL-1α, IL-6, IL-33, TNF-α, CCL2, IFN-γ, IL-10, IL12p70, MCP-1, and HMGB1, reduce cellular infiltrates in the lung, reduce ASC speck formation, and provide protection against inflammasome-mediated lung disease.

As used herein, "inflammasome-mediated disease or condition" refers to a disease or condition that is associated with NLRP3 and/or NLRP1 inflammasome activation or activity. In some embodiments, the inflammasome-mediated disease or condition is an inflammasome-mediated lung disease or condition.

As used herein, "inflammasome-mediated lung disease or condition," refers to acute or chronic respiratory inflammation-related disease or condition or diseases or conditions caused by pathogens, including, but not limited to, pandemic influenza (e.g., influenza A), *Streptococcus pneumoniae, Pseudomonas aeruginosa, Mycobacterium tuberculosis*, and other bacterial infections, acute respiratory distress syndrome (ARDS), respiratory syndromes caused by novel emerging respiratory viruses (i.e., Severe Acute Respiratory Syndrome coronavirus 2 (SARS-CoV-2), which causes COVID-19, Middle East Respiratory Syndrome coronavirus (MERS-CoV), which causes MERS, Severe Acute Respiratory Syndrome coronavirus (SARS-CoV), which causes SARS), respiratory syndromes caused by rhinovirus, Flaviviruses, Dengue virus, Zika virus, and/or West Nile virus, idiopathic pulmonary fibrosis (IPF), chronic obstructive pulmonary disease (COPD), acute exacerbations of COPD (AECOPD), asthma, and inflammasome-mediated lung disease or condition triggered by environmental exposure to irritants, including, but not limited to, silica (e.g., silicosis), asbestos (e.g., asbestosis), smoke, cigarette smoke, and nanoparticles, such as titanium dioxide. As demonstrated by the experimental examples presented herein, the probenecid analogs of the present technology (e.g., BT032, BT132) are effective as inhibitors of inflammasome activation and are effective in methods for preventing or treating inflammasome-mediated lung disease or condition. Therefore, because the probenecid analogs of the present technology are effective in such methods, a person of ordinary skill in the art would understand that the probenecid analogs of the present technology (e.g., BT032, BT132) are effective in methods for treating any inflammasome-mediated lung disease or condition and are not limited to the illustrative diseases/pathogens that cause inflammasome-mediated lung diseases or conditions listed herein.

As used herein, "to inhibit inflammasome activation" means to completely or partially inhibit the inflammasome activation by a stimulating factor. In other words, "to inhibit inflammasome activation" means to reduce the amount of produced activated caspase-1 or the amount of released inflammatory cytokine, such as IL-1β, IL-18, IL-1α, IL-6, IL-33, TNF-α, MCP-1, and HMGB1, or the formation of ASC specks, with the compounds of the present technology as compared to a non-treated control.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

"Tautomers" refers to isomeric forms of a compound that are in equilibrium with each other, and involve migration of at least one atom or group (e.g., a hydrogen atom) and at least one change in bond valence (e.g., between a single and double bond). The presence and concentrations of the isomeric forms will depend on the environment the compound is found in and may be different depending upon, for example, whether the compound is a solid or is in an organic or aqueous solution, what the temperature is, and whether an acid or base is present. For example, in aqueous solution, as shown below imines may be in equilibrium with enamines, which are referred to as tautomers of each other:

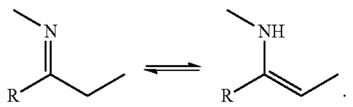

Similarly, those of skill in the art will be familiar with other tautomeric forms such as, e.g., keto/enol tautomers, keto/phenol tautomers, and the like. Because of the limits of representing compounds by structural formulas, it is to be understood that all chemical formulas of the compounds described herein represent all tautomeric forms of compounds and are within the scope of the present technology.

"Treating," "treat," "treated," or "treatment" as used herein covers the treatment of a disease or disorder or condition described herein (e.g., inflammasome-mediated lung disease or an inflammasome-mediated lung condition), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. Symptoms may be assessed by methods known in the art.

As used herein, "prevention" or "preventing" of a disorder or condition refers to a compound that, in a statistical sample, reduces the occurrence of the disorder or condition in the treated sample relative to a control sample, or delays the onset of one or more symptoms of the disorder or condition relative to the control sample.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, ayes, etc. In some embodiments, the mammal is murine. In some embodiments, the mammal is human.

A subject "in need" of treatment according to the methods and/or compositions of the present technology includes a subject that is "suffering" from an inflammasome-mediated lung disease or condition (i.e., a subject that is experiencing and/or exhibiting one or more clinical and/or subclinical symptoms of an inflammasome-mediated lung disease or condition), and a subject "at risk" of an inflammasome-mediated lung disease or condition. A subject "in need" of treatment includes animal models of inflammasome-mediated lung disease or condition. Subject "at risk" of inflammasome-mediated lung disease or condition refers to a subject that is not currently exhibiting inflammasome-mediated lung disease or condition symptoms and is predisposed to expressing one or more symptoms of the disease or condition. This predisposition may be based on family history, genetic factors, environmental factors such as exposure to detrimental compounds present in the environment, etc. It is not intended that the present technology be limited to any particular signs or symptoms. Thus, it is intended that the present technology encompass subjects that are experiencing any range of disease or condition, from sub-clinical symptoms to full-blown inflammasome-mediated lung disease, wherein the subject exhibits at least one of the indicia (e.g., signs and symptoms) associated with the inflammasome-mediated lung disease or condition.

II. General

Activation of certain NLRs (NLRP1, NLRP3, and NLRC4) leads to assembly of inflammasomes, which are large macromolecular signaling complexes that control the proteolytic activation of proinflammatory cytokines of the IL-1 family (e.g., IL-1β and IL-18) in response to any array of stimuli such as pathogens (e.g., viral or bacterial infections), environmental irritants, and endogenous danger signals. Growing evidence indicates that the inflammasome plays a key role in the pathogenesis of acute and chronic respiratory diseases. For example, inflammasome activation may be involved in acute lung inflammation after viral infection and during progression of several chronic pulmonary diseases, including idiopathic pulmonary fibrosis (IPF), chronic obstructive pulmonary disease (COPD), acute exacerbations of COPD (AECOPD), and asthma.

In one aspect, the present technology provides methods, compounds, and compositions for treating, preventing, or ameliorating inflammasome-mediated disease. In some embodiments, the inflammasome-mediated disease is an inflammasome-mediated lung disease. In some embodiments, inflammasome-mediated lung diseases comprise acute or chronic respiratory inflammation-related disease or disease caused by pathogens, including, but not limited to, pandemic influenza (e.g., influenza A), *Streptococcus pneumoniae, Pseudomonas aeruginosa, Mycobacterium tuberculosis*, and other bacterial infections, acute respiratory distress syndrome (ARDS), respiratory syndromes caused by novel emerging respiratory viruses (i.e., Severe Acute Respiratory Syndrome coronavirus 2 (SARS-CoV-2), which causes COVID-19, Middle East Respiratory Syndrome coronavirus (MERS-CoV), which causes MERS, Severe Acute Respiratory Syndrome coronavirus (SARS-CoV), which causes SARS), respiratory syndromes caused by rhinovirus, Flaviviruses, Dengue virus, Zika virus, and/or West Nile virus, idiopathic pulmonary fibrosis (IPF), chronic obstructive pulmonary disease (COPD), acute exacerbations of COPD (AECOPD), asthma, and inflammasome-mediated lung disease triggered by environmental exposure to irritants, such as, but not limited to, silica (e.g., silicosis), asbestos (e.g., asbestosis), smoke, cigarette smoke, and nanoparticles, such as titanium dioxide.

As demonstrated by the experimental examples presented herein, the probenecid analogs of the present technology (e.g., BT032, BT132, BT135, BT136, BT137, and BT159) are effective as inhibitors of inflammasome activation and are effective in methods for preventing or treating inflammasome-mediated diseases or conditions. The experimental examples also demonstrate that the probenecid analogs of the present technology are effective in methods for preventing or treating inflammasome-mediated lung diseases or conditions. Therefore, because the probenecid analogs of the present technology are effective in such methods, a person of ordinary skill in the art would understand that the probenecid analogs of the present technology (e.g., BT032, BT132, BT135, BT136, BT137, and BT159) are effective in methods for treating any inflammasome-mediated lung disease and are not limited to the illustrative diseases/pathogens that cause inflammasome-mediated lung disease listed herein.

In some embodiments, treating or preventing and inflammasome-mediated lung disease comprises reducing pro-inflammatory cytokine production, cellular infiltrates in the lung, ASC speck formation, and/or reducing the hyper-inflammation that frequently accompanies inflammasome-mediated lung disease. In some embodiments, the pro-inflammatory cytokines include IL-1β, IL-18, IL-1α, IL-6, IL-33, TNF-α, MCP-1, and HMGB1.

III. Compounds of the Present Technology

The present technology provides compositions for treating inflammasome-mediated disease. In some embodiments, the present technology provides compositions for treating inflammasome-mediated lung disease and conditions.

In some embodiments, the present technology discloses a probenecid analog defined by Formula I and pharmaceutically acceptable salts thereof:

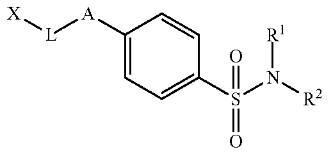

I tautomers thereof and/or pharmaceutically acceptable salts thereof;

wherein

A is absent, or is selected from the group consisting of $C(O)N(R^3)$, phenylene, oxazolylene, thiazolylene, piperidinylene and

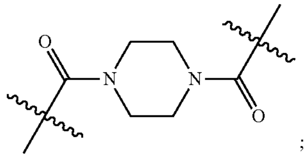 [SMILES: *C(=O)N1CCN(C(*)=O)CC1]

;

L is absent or $C_{1-10}$ alkylene;

X is H, CHO, COOH, $C(O)NR^4R^5$, $COOR^6$, $NH_2$ or NHR;

R is 2-chloropyrimidin-4-yl;

$R^1$ and $R^2$ are independently a substituted or unsubstituted $C_{1-6}$ alkyl group, or one of $R^1$ and $R^2$ is H, and the other is cyclohexyl-NH—C(O), or $R^1$ and $R^2$ together are a $C_{4-6}$ alkylene group and form a 5-, 6-, or 7-member ring with the nitrogen to which they are attached, said ring optionally substituted with a phenyl group;

$R^3$ and $R^4$ are independently selected from H or a $C_{1-6}$ alkyl group;

$R^5$ is selected from H, PEG, or a $C_{1-6}$ alkyl group; and $R^6$ is selected from a substituted or unsubstituted $C_{1-10}$ alkyl, $C_{2-10}$ alkenyl, or $C_{7-14}$ aralkyl group.

In some embodiments of the compounds of Formula I, A may be absent. In some embodiments, A may be $C(O)N(R^3)$, wherein $R^3$ is H or a $C_{1-6}$ alkyl group. In some such embodiments $R^3$ may be H or methyl. In some embodiments, A may be phenylene, oxazolylene, thiazolylene, piperidinylene or

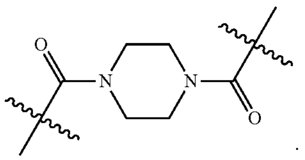 [SMILES: *C(=O)N1CCN(C(*)=O)CC1]

For example, A may be phenylene.

In some embodiments of compounds of Formula I, L may be absent. In some embodiments L may be a $C_{1-10}$ alkylene, for example a $C_1$, $C_2$, $C_3$, $C_4$, $C_5$, $C_6$, $C_7$, $C_8$, $C_9$, or $C_{10}$ alkylene or a range between and including any two of the foregoing values of L.

In some embodiments of compounds of Formula I, X may be H. In some embodiments, X may be COOH. In some embodiments, X may be $COOR^6$, where $R^6$ may be defined as herein. For example, $R^6$ may be a substituted or unsubstituted $C_{1-10}$ alkyl group, or a $C_{1-6}$ alkyl group, e.g., a substituted or unsubstituted methyl or ethyl group. $R^6$ may be a substituted or unsubstituted $C_{2-10}$ alkenyl group, or a $C_{2-6}$ alkenyl group, e.g., a substituted or unsubstituted allyl group. $R^6$ may be a substituted or unsubstituted $C_{7-14}$ aralkyl group or a substituted or unsubstituted $C_{7-10}$ aralkyl group, e.g., a substituted or unsubstituted benzyl or phenethyl group. In some embodiments X may be $NH_2$ or X may be NHR where R is R is 2-chloropyrimidin-4-yl. In some embodiments, X may be $C(O)NR^4R^5$ where $R^4$ and $R^5$ may be as defined herein. For example $R^4$ may be H, or $R^4$ may be a $C_{1-6}$ alkyl group. In some embodiments, $R^5$ may be H. In some embodiments, $R^5$ may be a $C_{1-6}$ alkyl group. In some embodiments, $R^5$ may be a polyethylene glycol (PEG).

PEG may have any suitable geometry (linear, branched, multi-arm) and any suitable average molecular weight. In some embodiments, the PEG is a linear PEG. In some embodiments, the PEG may have an average molecular weight in the range of about 100 Da to about 40 kDa. (Unless otherwise indicated, "average molecular weight" means weight average molecular weight.) In some embodiments, the average molecular weight of the polymer is about 100 Da, 200 Da, 300 Da, 400 Da, 500 Da, 550 Da, 600 Da, 700 Da, 800 Da, 900 Da, 1 kDa, 1.5 kDa, 2 kDa, 3 kDa, 4 kDa, 5 kDa, 7.5 kDa, 10 kDa, 15 kDa, 20 kDa, 25 kDa, 30 kDa, 40 kDa, or any range between and including two of these values. For example, the PEG may have an average molecular weight in the range of about 500 Da to about 2 or to about 3 kDa.

In some embodiments, the PEG may be functionalized at one or more of its termini with amine ($NH_2$) and/or aldehyde (CHO) groups and include linear mono-amines and mono-aldehydes, linear bi-amines and bi-aldehydes, multi-arm-amines and multi-arm-aldehydes, branched mono-, bi- and multi-armed-amines and aldehydes and multi-arm-forked-amines and aldehydes. The PEG may terminate in a hydroxyl or in a $C_{1-6}$ ether, e.g., a methyl or ethyl ether. In some embodiments the PEG may be functionalized with an amine at one terminus and a hydroxyl or $C_{1-6}$ ether at another terminus. In some such embodiments, the PEG is a linear PEG.

In some embodiments of compounds of Formula I, each of $R^1$ and $R^2$ may independently be a $C_{1-6}$ alkyl group. The latter may be optionally substituted, e.g., with one or more (e.g., 1, 2, or 3) F, OH, $CF_3$, $C_{3-7}$ cycloalkyl group or $SO_2$-alkyl. In some embodiments, $R^1$ and $R^2$ together may be a $C_{4-6}$ alkylene group and form a 5-, 6-, or 7-member ring with the nitrogen to which they are attached. Thus, $R^1$ and $R^2$ together may be a $C_{4-6}$ alkylene group and form a pyrrolidine, piperidine, or azepane, each of which may be optionally substituted with a phenyl group. In some embodiments, one of $R^1$ and $R^2$ is H, and the other is cyclohexyl-NH—C(O).

In some embodiments of compounds of Formula I, A is absent, or is selected from the group consisting of C(O)N($R^3$), phenylene, oxazolylene, thiazolylene, and piperidinylene, L is absent or $C_{1-10}$ alkylene; X is H, COOH, or $NH_2$; $R^1$ and $R^2$ are independently a substituted or unsubstituted $C_{1-6}$ alkyl group; and $R^3$ is selected from H or a $C_{1-6}$ alkyl group. In some embodiments, A may be absent and L may be $C_{3-10}$ alkylene. In some embodiments, A may be phenylene, oxazolylene, thiazolylene, or piperidinylene, and L is absent or a $C_{1-5}$ alkylene. In some embodiments, X may be COOH or $NH_2$.

It will be appreciated by those of skill in the art that disclosure of any compound herein, including compounds of Formula I and other probenecid analogs also discloses tautomers thereof, and/or pharmaceutically acceptable salts thereof. In some embodiments, the present technology discloses a probenecid analog defined by Formula Ia (BT004):

(Ia)

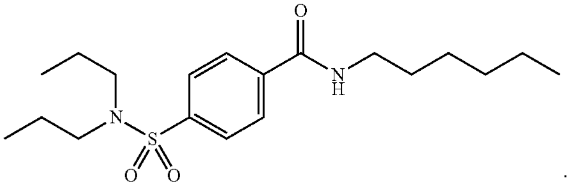

In some embodiments, the present technology discloses a probenecid analog defined by Formula Ib (BT005):

(Ib)

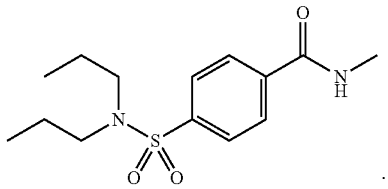

In some embodiments, the present technology discloses a probenecid analog defined by Formula Ic (BT006):

(Ic)

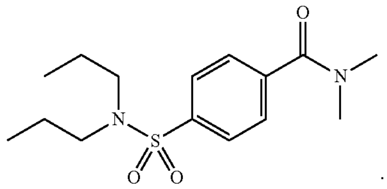

In some embodiments, the present technology discloses a probenecid analog defined by Formula Id (BT007):

(Id)

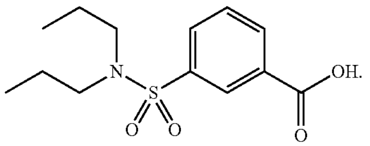

In some embodiments, the present technology discloses a probenecid analog defined by Formula Ie (BT008):

(Ie)

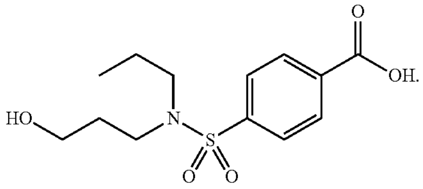

In some embodiments, the present technology discloses a probenecid analog defined by Formula If (BT009):

(If)

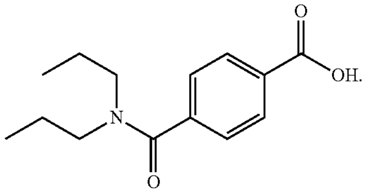

In some embodiments, the present technology discloses a probenecid analog defined by Formula Ig (BT010):

(Ig)

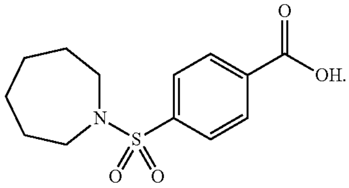

In some embodiments, the present technology discloses a probenecid analog defined by Formula Ih (BT011):

(Ih)

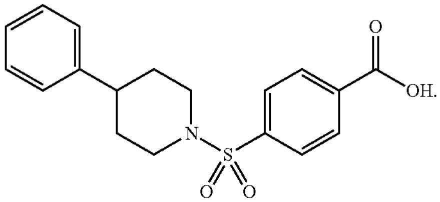

In some embodiments, the present technology discloses a probenecid analog defined by Formula Ii (BT026):

(Ii)

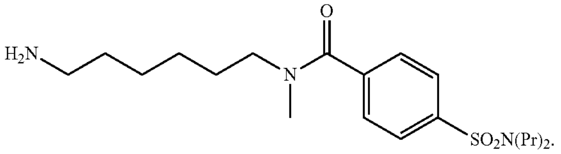

In some embodiments, the present technology discloses a probenecid analog defined by Formula Ij (BT027):

(Ij)

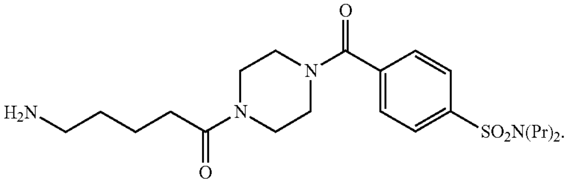

In some embodiments, the present technology discloses a probenecid analog defined by Formula Ik (BT028):

(Ik)

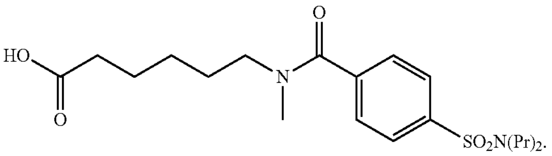

In some embodiments, the present technology discloses a probenecid analog defined by Formula Il (BT029):

(Il)

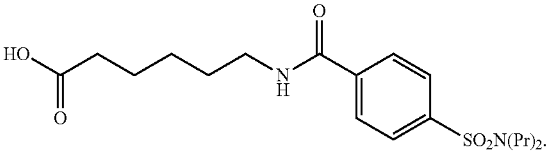

In some embodiments, the present technology discloses a probenecid analog defined by Formula Im (BT030):

(Im)

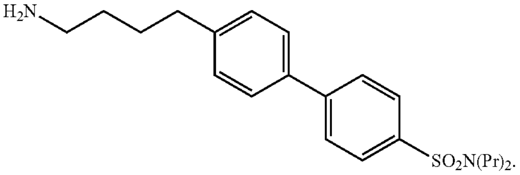

In some embodiments, the present technology discloses a probenecid analog defined by Formula In (BT031):

(In)

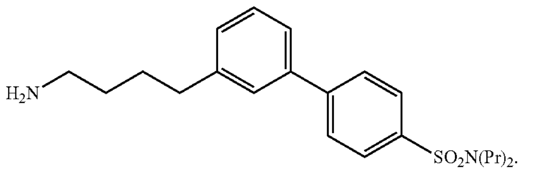

In some embodiments, the present technology discloses a probenecid analog defined by Formula Io (BT032):

(Io)

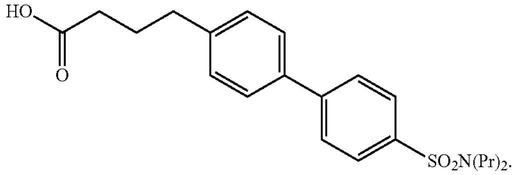

In some embodiments, the present technology discloses a probenecid analog defined by Formula Ip (BT033):

(Ip)

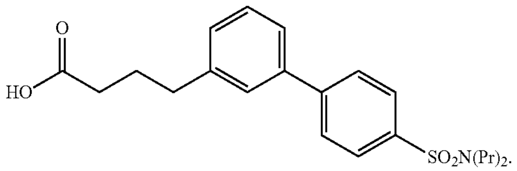

In some embodiments, the present technology discloses a probenecid analog defined by Formula Iq (BT034):

(Iq)

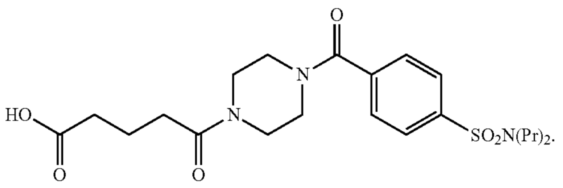

In some embodiments, the present technology discloses a probenecid analog defined by Formula Is (BT041):

(Is)

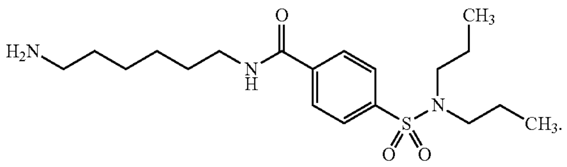

In some embodiments, the present technology discloses a probenecid analog defined by Formula It (BT043):

(It)

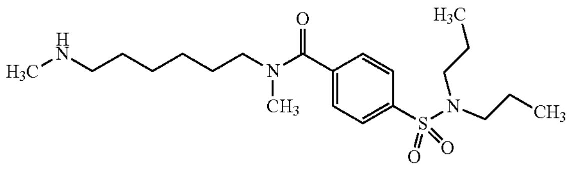

In some embodiments, the present technology discloses a probenecid analog defined by Formula Iu (BT052, also known as BT159):

(Iu)

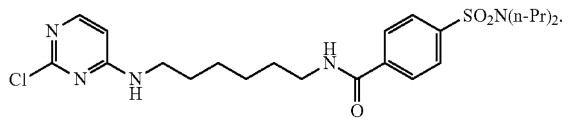

In some embodiments, the present technology discloses a probenecid analog defined by Formula Iv (BT053):

(Iv)

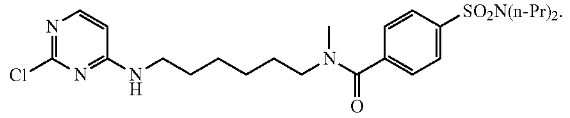

In some embodiments, the present technology discloses a probenecid analog defined by Formula Iw (BT054):

(Iw)

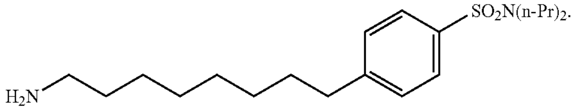

In some embodiments, the present technology discloses a probenecid analog defined by Formula Ix (BT055):

(Ix)

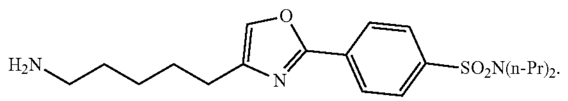

In some embodiments, the present technology discloses a probenecid analog defined by Formula Iy (BT056):

(Iy)

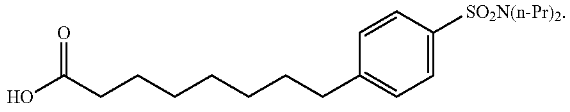

In some embodiments, the present technology discloses a probenecid analog defined by Formula Iz (BT057):

(Iz)

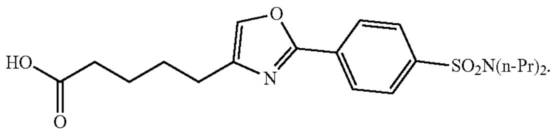

In some embodiments, the present technology discloses a probenecid analog defined by Formula Iaa (BT058):

(Iaa)

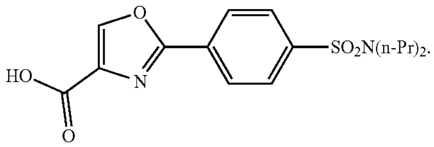

In some embodiments, the present technology discloses a probenecid analog defined by Formula Iab (BT132):

(Iab)

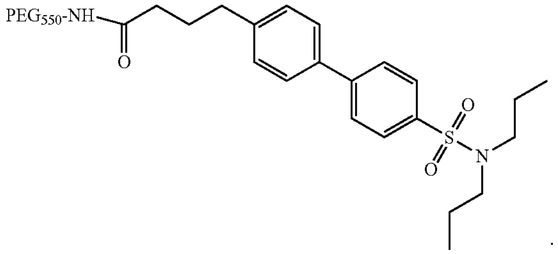

In some embodiments, the present technology discloses a probenecid analog defined by Formula Iac (BT133):

(Iac)

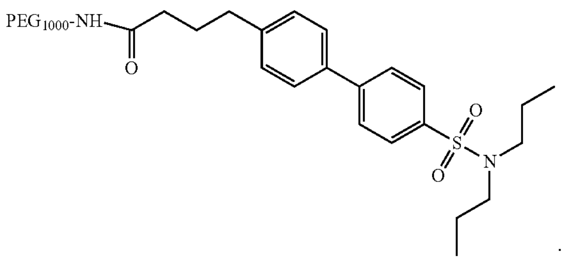

In some embodiments, the present technology discloses a probenecid analog defined by Formula Iad (BT134):

(Iad)

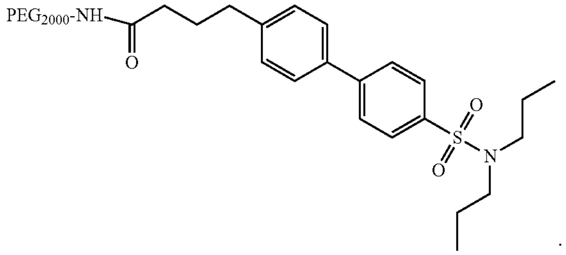

In some embodiments, the present technology discloses a probenecid analog defined by Formula Iae (BT135):

(Iae)

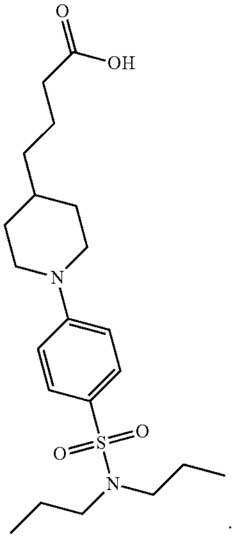

In some embodiments, the present technology discloses a probenecid analog defined by Formula Iaf (BT136):

(Iaf)

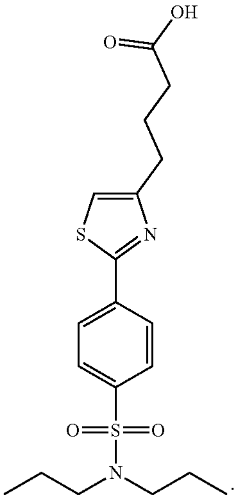

In some embodiments, the present technology discloses a probenecid analog defined by Formula Iag (BT137):

(Iag)

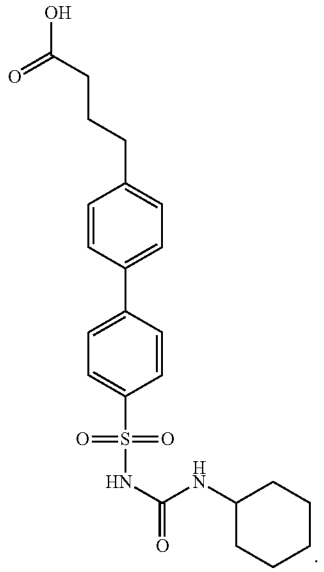

In some embodiments, the present technology discloses a probenecid analog defined by Formula Iah (BT138):

(Iah)

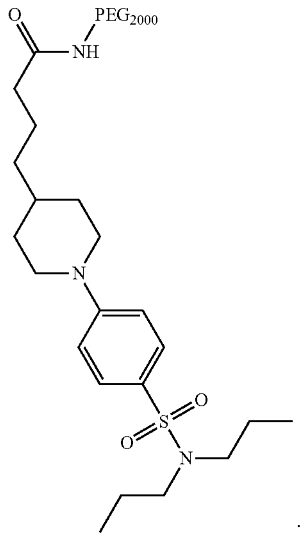

In some embodiments, the present technology discloses a probenecid analog defined by Formula Iai (BT139):

(Iai)

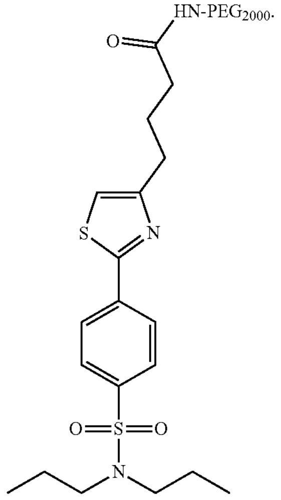

In some embodiments, the present technology discloses a probenecid analog defined by Formula Iaj (BT140):

(Iaj)

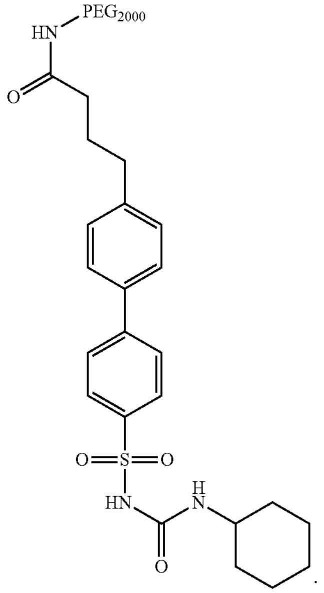

In another aspect, the present disclosure provides compounds of Formula II:

II

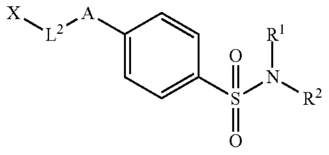

tautomers thereof and/or pharmaceutically acceptable salts thereof;

wherein

A is absent, or is selected from the group consisting of C(O)N($R^3$), phenylene, oxazolylene, thiazolylene, piperidinylene, and

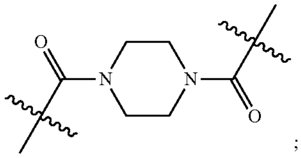 [SMILES: *C(=O)N1CCN(C(*)=O)CC1]

;

$L^2$ is absent or is a $C_{1-12}$ alkylene or $C_{1-12}$ heteroalkylene group, or a peptide comprising 2-10 amino acid residues;

X is H, CHO, COOH, C(O)N$R^4R^5$, COO$R^6$, $NH_2$ or NHR;

R is 2-chloropyrimidin-4-yl;

$R^1$ and $R^2$ are independently a substituted or unsubstituted $C_{1-6}$ alkyl group, or one of $R^1$ and $R^2$ is H, and the other is cyclohexyl-NH—C(O), or $R^1$ and $R^2$ together are a $C_{4-6}$ alkylene group and form a 5-, 6-, or 7-member ring with the nitrogen to which they are attached, said ring optionally substituted with a phenyl group;

$R^3$ and $R^4$ are independently selected from H or a $C_{1-6}$ alkyl group;

$R^5$ is selected from H, a polymer carrier, or a $C_{1-6}$ alkyl group, wherein the polymer carrier is pharmaceutically acceptable polymer; and $R^6$ is selected from a substituted or unsubstituted $C_{1-10}$ alkyl, $C_{2-10}$ alkenyl, or $C_{7-14}$ aralkyl group.

In the present aspect, probenecid (or analogs thereof, e.g., as defined in Formula II) is attached to a polymer carrier via a linker $L^2$. In some embodiments, the linker can serve as a spacer to distance the probenecid analog and the polymer in order to avoid interference, with, for example, binding capabilities. The linker comprises one or more atoms, e.g., one or more atoms selected from C, N, or O. In some such embodiments the linker may further comprise one or more H atoms, e.g., NH, N($CH_3$), or $CH_2$.

In some embodiments, the linker is a biodegradable linker. In some embodiments, the biodegradable linker comprises an oligopeptide having from 2 to 10 amino acid residues. The residues may be selected from the naturally occurring amino acids.

In some embodiments, the linker comprises a substituted or unsubstituted $C_1$-$C_z$ alkylene, cycloalkylene, cycloalkyl-alkylene, heteroalkylene, alkenylene, or heteroalkenylene group, wherein z may be any integer from 1 to 12, i.e., 1, 2, 3, 4, 5, 6, 7, 8, 9, 10, 11 or 12. For example, the linker may comprise a C1-Cz fluoroalkyl group where one or more of the hydrogen atoms are fluorine atoms, such as 1, 2 or 3 or more fluorines. In some embodiments, $L^2$ is a heteroalkylene containing one or two NH groups, including but not limited to ($C_1$-$C_{10}$ alkylene)-NH (e.g., $CH_2CH_2NH$, $CH_2CH_2CH_2NH$, $CH_2CH_2CH_2CH_2NH$, $CH_2CH(CH_3)CH(CH_3)CH_2NH$), ($C_n$ alkylene)NH($C_p$ alkylene) where n, p are independently an integer from 1-10, but n+p does not exceed 10 (e.g., $CH_2CH_2CH_2NH\ CH_2CH_2$), NH—($C_1$-$C_{10}$ alkylene)NH (e.g., $NH(CH_2)_5NH$, $NH(CH_2)_6NH$, $NH(CH_2)_8\ NH$), or NH($C_n$ alkylene)NH($C_p$ alkylene) where n and p are integers as defined previously (e.g., $NHCH_2CH_2CH_2NH\ CH_2CH_2$, $NH(CH_2)_6NHCH_2$). In some embodiments, $L^2$ is a heteroalkylene that contains one or two oxygen atoms, including but not limited to ($C_1$-$C_{10}$ alkylene)-O (e.g., $CH_2CH_2O$, $CH_2CH_2CH_2O$, $CH_2CH_2CH_2CH_2O$, $CH_2CH(CH_3)CH(CH_3)CH_2O$), ($C_n$ alkylene)O($C_p$ alkylene) where n, p are independently an integer from 1-10, but n+p does not exceed 10 (e.g., $CH_2CH_2CH_2OCH_2CH_2$), O—($C_1$-$C_{10}$ alkylene)O (e.g., $O(CH_2)_5O$, $O(CH_2)_6O$, $O(CH_2)_8O$), or O($C_n$ alkylene)O($C_p$ alkylene) where n and p are integers as defined previously (e.g., $OCH_2CH_2CH_2O\ CH_2CH_2$, $O(CH_2)_6OCH_2$). In some embodiments, $L^2$ is a heteroalkylene containing an O and an NH group, including but not limited to NH—($C_1$-$C_{10}$ alkylene)O, (e.g., $NH(CH_2)_5O$, $NH(CH_2)_6O$, $NH(CH_2)_8O$), or NH($C_n$ alkylene)O($C_p$ alkylene) where n and p are integers as defined previously (e.g., $NHCH_2CH_2OCH_2CH_2$, $O(CH_2)_6NHCH_2$).

In some embodiments, the polymer carrier is selected from the group consisting of PEG, dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly(hydroxyalkylmethaacrylamide), polyglycerol, 25 polyamidoamine (PAMAM), polyethylenimine (PEI), and polypeptides (i.e., comprising alpha-amino acid residues). The polymer may have any suitable weight average molecular weight, e.g., from about 100 Da to about 40 kDa. In some embodiments, the average molecular weight of the polymer is about 100 Da, 200 Da, 300 Da, 400 Da, 500 Da, 550 Da, 600 Da, 700 Da, 800 Da, 900 Da, 1 kDa, 1.5 kDa, 2 kDa, 3 kDa, 4 kDa, 5 kDa, 7.5 kDa, 10 kDa, 15 kDa, 20 kDa, 25 kDa, 30 kDa, 40 kDa, or any range between and including two of these values. In some embodiments, the polymer carrier is PEG and may have the structure disclosed herein above.

In addition, variables A, X, R, $R^1$, $R^2$, $R^3$, $R^4$, $R^5$, $R^6$, may also have any of the values disclosed herein, e.g., any of the values disclosed with respect to Formula I, as all such embodiments are intended for use with Formula II as well.

The probenecid-polymer conjugates may be prepared using standard techniques known in the art. In some embodiments, a difunctional linker containing at least two functional groups containing heteroatoms selected from N, O, and S in which one of the functional groups is protected may be conjugated using standard ester, thioester and amide bond forming technology. For example, a diamino-alkylene linker in which one of the amino groups is protected by a urethane protecting group (e.g., Boc. Cbz, etc.) may be coupled to probenecid in the presence of a coupling agent (e.g., DCC, EDC/HOBt, etc.). Alternatively, an active ester, mixed anhydride or acid halide derivative of probenecid may be prepared and reacted with the mono-protected diamine. (See, for example, Bodanszky, M. & Bodanszky, A., *The Practice of Peptide Synthesis*, Springer-Verlag, New York, 1984.) The protecting group may be removed and the free amine reacted with an aldehyde derivative of the polymer under reducing conditions to provide the conjugate. Similarly, a linker with a protected aldehyde (e.g., 1,1-dimethoxy) and an amine may be coupled to the probenecid, deprotected to form the aldehyde and subjected to reductive amination with an amino-bearing polymer to form the conjugate. Variations of these schemes using α,ω-carboxy amines, α,ω-aminoalcohols, α,ω-carboxyalcohols, α,ω-aminothiols, and the like to link probenecid and the polymer will be readily understood by those of skill in the art.

IV. Use of the Compositions of the Present Technology

The present technology provides methods for treating, preventing, or ameliorating inflammasome-mediated lung disease or conditions in a mammalian subject in need thereof, comprising administering to the subject a therapeutically effective amount of one or more probenecid analogs of the present technology. In some embodiments, the inflammasome-mediated lung disease or condition is/is caused by a pathogen selected from one or more of, but not limited to, pandemic influenza (e.g., influenza A), *Streptococcus pneumoniae, Pseudomonas aeruginosa, Mycobacterium tuberculosis*, acute respiratory distress syndrome (ARDS), COVID-19, MERS, SARS, respiratory syndromes caused by rhinovirus, Flaviviruses, Dengue virus, Zika virus, and/or West Nile virus, idiopathic pulmonary fibrosis (IPF), chronic obstructive pulmonary disease (COPD), acute exacerbations of COPD (AECOPD), asthma, and silicosis. In some embodiments, the probenecid analog is a compound of Formula I and pharmaceutically acceptable salts thereof, including a compound of any one of Formulas Ia-Iaj. In some embodiments, the probenecid analog is a compound of Formulas Io (BT032), Iab (BT132), Iac (BT133), Iae (BT135), Iaf (BT136), or Iag (BT137). In a further embodiment, the probenecid analogs of the present technology reduce pro-inflammatory cytokine production and/or reduce cellular infiltrates in the lung. In some embodiments, the probenecid analogs of the present technology diminish IL-1β secretion.

As demonstrated by the experimental examples presented herein, the probenecid analogs of the present technology (e.g., BT032, BT132) are effective as inhibitors of inflammasome activation and are effective in methods for preventing or treating inflammasome-mediated lung disease or conditions. Therefore, because the probenecid analogs of the present technology are effective in such methods, a person of ordinary skill in the art would understand that the probenecid analogs of the present technology (e.g., BT032, BT132) are effective in methods for treating any inflammasome-mediated lung disease or conditions and are not limited to the illustrative diseases/pathogens that cause inflammasome-mediated lung disease or conditions listed herein.

V Combination Therapies

In some embodiments, the probenecid analogs of the present technology may be combined with one or more additional therapeutic agents for the prevention, amelioration, or treatment of inflammasome-mediated lung disease or conditions.

In one embodiment, an additional therapeutic agent is administered to a subject in combination with a probenecid analog of the present technology (e.g., a compound of Formula I, including but not limited to Formulas Io (BT032), Iab (BT132), Iac (BT133), Iae (BT135), Iaf (BT136), or Iag (BT137)) such that a synergistic therapeutic effect is produced.

In some embodiments, the probenecid analogs of the present technology (e.g., a compound of Formula I, including but not limited to Formulas Io (BT032), Iab (BT132), Iac (BT133), Iae (BT135), Iaf (BT136), or Iag (BT137)) are combined with one or more compounds for the treatment or prevention of inflammasome-mediated lung disease or conditions or diseases or conditions caused by pathogens including, but not limited to, pandemic influenza (e.g., influenza A), *Streptococcus pneumoniae, Pseudomonas aeruginosa, Mycobacterium tuberculosis*, acute respiratory distress syndrome (ARDS), COVID-19, MERS, SARS, respiratory syndromes caused by rhinovirus, Flaviviruses, Dengue virus, Zika virus, and/or West Nile virus, idiopathic pulmonary fibrosis (IPF), chronic obstructive pulmonary disease (COPD), acute exacerbations of COPD (AECOPD), asthma, and silicosis.

As demonstrated by the experimental examples presented herein, the probenecid analogs of the present technology (e.g., BT032, BT132) are effective as inhibitors of inflammasome activation and are effective in methods for preventing or treating inflammasome-mediated lung disease or conditions. Therefore, because the probenecid analogs of the present technology are effective in such methods, a person of ordinary skill in the art would understand that the probenecid analogs of the present technology (e.g., BT032, BT132) are effective in methods for treating any inflammasome-mediated lung disease or conditions and are not limited to the illustrative diseases/pathogens that cause inflammasome-mediated lung disease or conditions listed herein.

The multiple therapeutic agents may be administered in any order or even simultaneously. If simultaneously, the multiple therapeutic agents may be provided in a single, unified form, or in multiple forms (by way of example only, either as a single formulation or as two separate formulations). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

In some embodiments, the methods of the present technology may further comprise administering one or more antibiotic and/or anti-inflammatory agents. Examples of antibiotic/anti-inflammatory agents used singly or in combination in the methods of the present technology include, but are not limited to tetracyclines, macrolide antibiotics (e.g., azithromycin), fluoroquinolones, ceftazidime, ciprofloxacin, levofloxacin, gentamicin, cefepime, aztreonam, carbapenems, ticarcillin, ureidopenicillins, isoniazid, rifampin, ethambutol, pyrazinamide, streptomycin, corticosteroids (e.g., hydrocortisone, cortisone, ethamethasoneb, fludrocortisone, bethamethasone, prednisone, prednisolone, triamcinolone, methylprednisone, dexamethasone), non-steroidal agents such as COX inhibitors, LOX inhibitors, p38 kinase inhibitors, immunosuppressant agents such as cyclosporin, and cytokine synthesis inhibitors, minocycline, and doxycycline, and diuretics, or any combination thereof.

VI. Modes of Administration

Any method known to those in the art for contacting a cell, organ, or tissue with compounds of the present technology may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of a compound of the present technology to a mammal such as a human. When used in vivo for therapy, a compound of the present technology is administered to a mammal in an amount effective to obtain the desired result, e.g., of treating the mammal. The effective amount is determined during pre-clinical trials and clinical trials by methods familiar to physicians and clinicians. The dose and dosage regimen will depend upon the degree of the disease or condition in the subject, the characteristics of the particular compound of the present technology used, e.g., its therapeutic index, the subject, and the subject's history.

An effective amount of a compound of the present technology useful in the present methods, such as in a pharmaceutical composition or medicament, may be administered to a mammal in need thereof by any of a number of well-known methods for administering pharmaceutical compositions or medicaments. The compounds of the present technology may be administered systemically or locally.

The compounds of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

In some embodiments, the pharmaceutical compositions of the present disclosure contain a pharmaceutically acceptable carrier and/or excipient suitable for rendering the compound or mixture administrable orally as a tablet, capsule or pill, or parenterally, intravenously, intradermally, intramuscularly, intracutaneously, subcutaneously, or transdermally.

Pharmaceutical compositions are typically formulated to be compatible with the intended route of administration. Administering the pharmaceutical composition of the present disclosure may be accomplished by any means known to the skilled artisan. Routes of administration include, but are not limited to, parenteral, intranasal/respiratory (e.g., inhalation), intravenous, intramuscular, intradermal, intraperitoneal, intratracheal, intracutaneous, subcutaneous, oral, transdermal (topical), sublingual, ocular, vaginal, rectal, and transmucosal administration. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In some embodiments, the compounds for use according to the present disclosure may be formulated for intra-alveolar administration, For example, in some embodiments, the compounds for use according to the present disclosure may be administered during a bronchoscopy procedure or microendoscopy procedure, which delivers the compound to alveolar spaces (i.e., microdosing in the lung).

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In some embodiments, administration is topical and/or at the luminal surface of the tissue to be treated. "Topical" administration of a composition means contacting the composition with the skin. "Luminal surface" refers to the inner open space or cavity of a tubular organ, such as the interior central space in an artery or vein through which blood flows; the interior of the gastrointestinal tract; the pathways of the bronchi in the lungs; the interior of renal tubules and urinary collecting ducts; the pathways of the female genital tract, starting with a single pathway of the vagina, splitting up in two lumina in the uterus, both of which continue through the fallopian tubes.

In some embodiments, the compounds of the present technology are administered topically and/or at a luminal surface of the target tissue. This is advantageous to reduce potential systemic toxic side effects of the compounds.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EXPERIMENTAL EXAMPLES

The present technology is further illustrated by the following examples, which should not be construed as limiting in any way.

Example 1: Synthesis of Probenecid Analogs

Illustrative examples of the general synthesis of probenecid analogs of the present technology are shown in Schemes 1-14.

Scheme 1 - Synthesis of BT132 (also referred to as BT032-1)

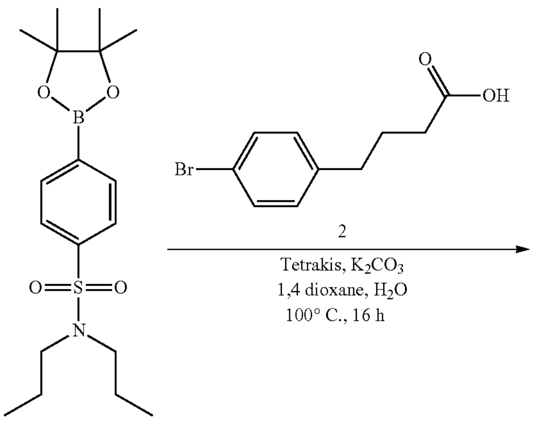

1

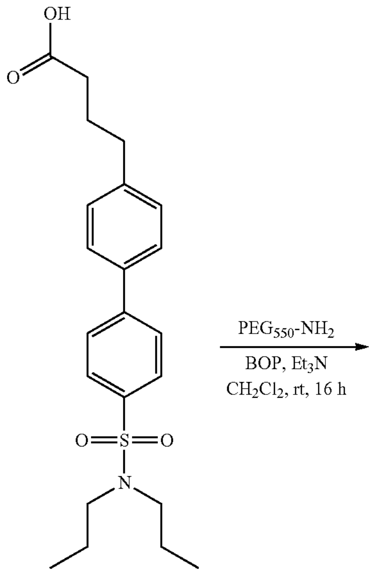

3

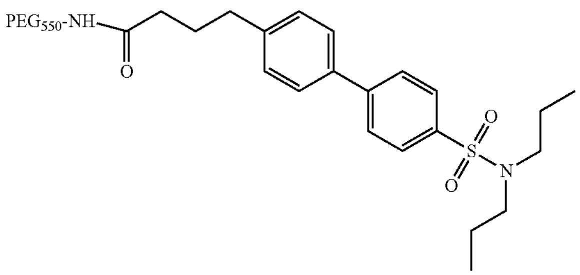

BT032-1

General procedure for Suzuki biaryl coupling reaction. To a solution of dioxaborolane 1 (Scheme 1; 1.5 mmol, 1.0 eq) in aqueous dioxane (5.0 mL) was added 4-(4-bromophenyl) butanoic acid (1.65 mmol, 1.1 eq), potassium phosphate (4.5 mmol, 3.0 eq) and palladium acetate ($(Pd(OAc)_2)$, 0.075 mmol, 0.5 eq). The reaction mixture was stirred at 100° C. for 18 h. The reaction mixture was cooled to room temperature, diluted with water (10.0 mL), acidified with 1 M aqueous HCl, and extracted with ethyl acetate (10.0 mL×2). The organic phase was washed with brine (20.0 mL), dried over sodium sulfate, filtered, and concentrated under reduced pressure to give a residue. The residue was purified by chromatography. 4-(4'-(N,N-dipropylsulfamoyl)-[1,1'-biphenyl]-4-yl)butanoic acid 3, also referred to herein as BT032, (0.8 mmol, 76% yield) was obtained as a white solid. MS: m/z=404 $(M+H)^+$.

General procedure for amide coupling reaction and formation of the PEG amides. To a solution of acid 3 (Scheme 1; 1.0 mmol, 1.0 eq) and polyethylene glycol amine ($(PEG_{550}-NH_2)$, 1.2 mmol, 1.2 eq) in dichloromethane (3.0 mL) was added BOP (benzotriazol-1-yloxytris(dimethylamino)phosphonium hexafluorophosphate, 1.2 mmol, 1.2 eq) and triethylamine (2.0 mmol, 2 eq). The reaction mixture was stirred at 25° C. for 16 h. The reaction mixture was poured into water and extracted with ethyl acetate (10.0 mL×2). The combined organic layers were washed sequentially with 1 M aqueous HCl (10 mL), saturate aqueous sodium bicarbonate (10 mL), brine (10.0 mL×2), dried over $Na_2SO_4$, filtered, and concentrated under reduced pressure to give a residue. The residue was purified by combi-flash chromatography eluted with 5-10% MeOH in $CH_2Cl_2$. $PEG_{550}$ amide BT032-1 (55 mg, 0.26 mmol, 26% yield) was obtained as a white solid. MS (electron spray ionization (ESI)=936 (average MW).

Scheme 2 - Synthesis of BT133 (also referred to as BT032-2)

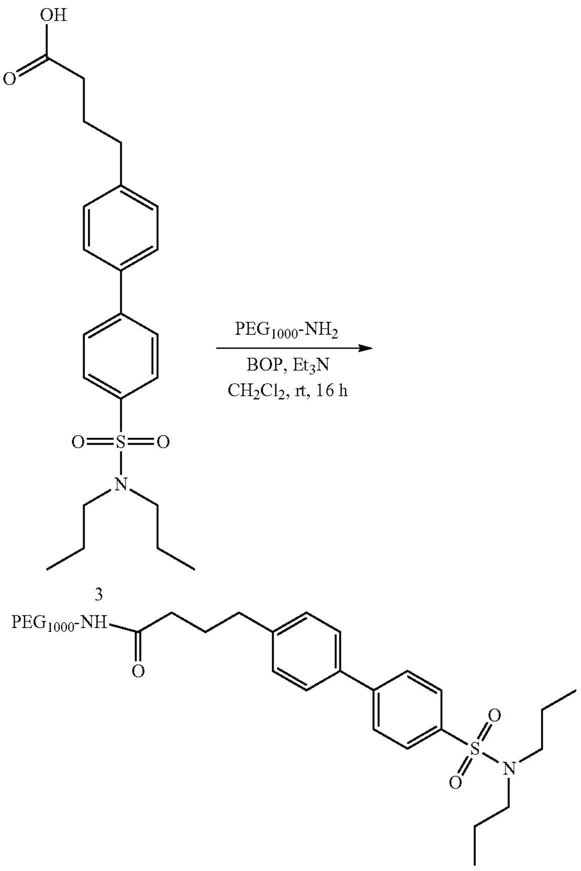

BT032-2

$PEG_{1000}$ amide BT032-2 was prepared from compound 3 (prepared as in Scheme 1) by adapting the general procedure of Scheme 1 for PEG amidation using $NH_2-PEG_{1000}$ as indicated in Scheme 2. Reaction details are found in the table below. BT032-2 was obtained as a white solid (100 mg) in 49% yield. MS (ESI)=1386 (average MW).

| S. No. | Reaction | Scale | Conditions | Yield | Comments |
|---|---|---|---|---|---|
| 1 | 3 to 5 | 0.20 g | Compound 3 (1.0 equiv.), Compound 4 (1.2 equiv.), $Pd(dppf)Cl_2CH_2Cl_2$ (0.2 equiv.), CuI (0.5 equiv.), $Et_3N$ (3 equiv.), 1,4-dioxane, 100° C., 4 h | 0.10 g (49%) | Compound 3 consumed; TLC showed formation of new spot; after work-up crude was purified by combi-flash chromatography eluted with 30-50% EtOAc in hexanes; $^1H$ NMR and UPLC consistent |
| 2 | 1 to 3 | 5.0 g | Compound 1 (1.0 equiv.), Compound 2 (1.1 equiv), $Pd(OAc)_2$ (0.05 equiv.), $K_3PO_4$ (3 equiv.), 1,4-dioxane, $H_2O$, 100° C., 16 h | 2.0 g (30%) | Compound 1 consumed; TLC showed formation of new spot; after work-up crude was purified by combi-flash chromatography eluted with 30-50% EtOAc in hexanes; $^1H$ NMR and UPLC consistent |

-continued

Scheme 3 - Synthesis of BT134 (also referred to as BT032-3)

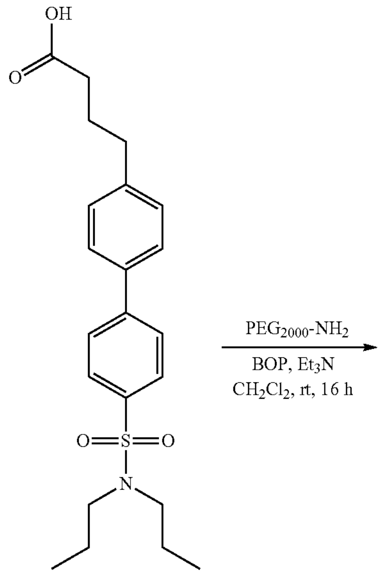

3

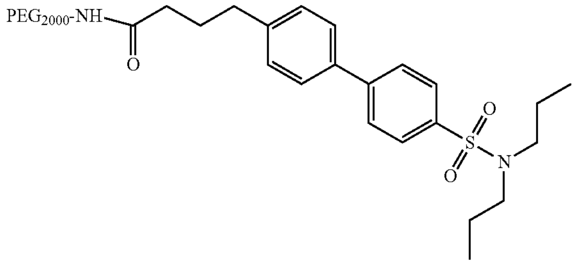

BT032-3

$PEG_{2000}$ amide BT032-3 was prepared from compound 3 (prepared as in Scheme 1) by adapting the general procedure of Scheme 1 for PEG amidation using $NH_2$-$PEG_{2000}$ as indicated in Scheme 3. Reaction details are found in the table below. BT032-3 was obtained as a white solid (800 mg) in 67% yield. MS (ESI)=2386 (average MW).

| S. No. | Reaction | Scale | Conditions | Yield | Comments |
|---|---|---|---|---|---|
| 1 | 3 to BT032-3 | 200 mg | Compound 3 (1.0 equiv.), $PEG_{(2000)}$-$NH_2$ (1.2 equiv.), BOP (1.2 equiv.), $Et_3N$ (2 equiv.), $CH_2Cl_2$, rt, 16 h | 800 mg (67%) | Compound 3 consumed; TLC showed formation of new spot; after work-up crude was purified by combi-flash chromatography eluted with 5-10% MeOH in $CH_2Cl_2$; $^1H$ NMR consistent and HPLC analysis in progress. |

Scheme 4 - Synthesis of BT135 (also referred to as BT0135) and BT138 (also referred to as BT0138)

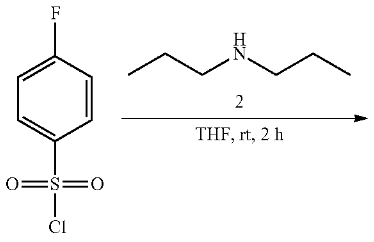

1

-continued

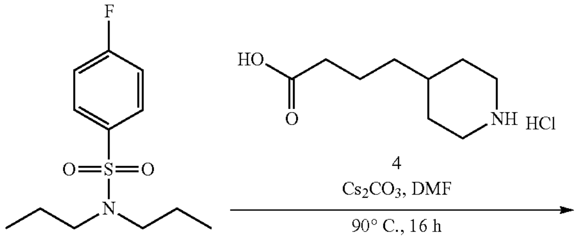

3

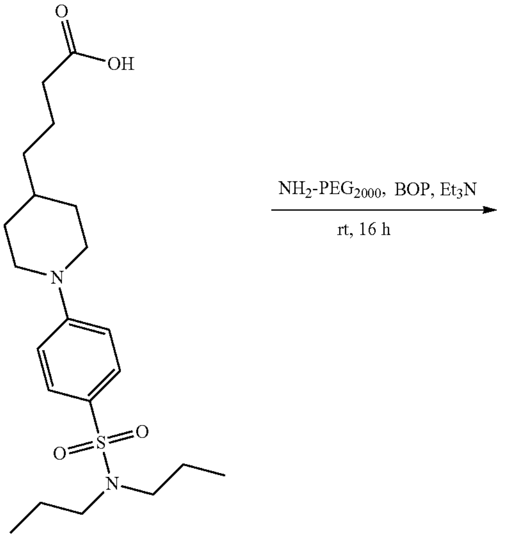

BT0135

-continued

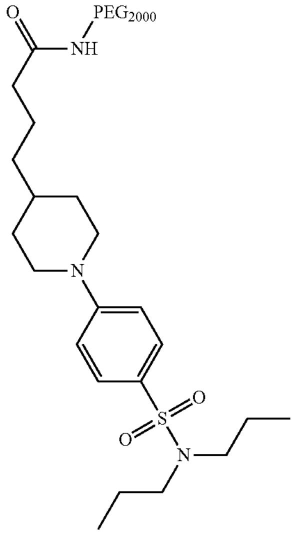

BT0138

Preparation of BT0135. To a solution of fluoride 3, the preparation of which is described in Kayumov, M., et al., *Advanced Synthesis & Catalysis* 362(4):776-781 (2020) (Scheme 4; 1.0 mmol, 1.0 eq) and piperidine 4 (1.1 eq.) in dimethylsulfoxide (5 mL) was added excess cesium carbonate (4.0 eq). The reaction mixture was stirred at 90° C. for 16 h. The reaction mixture was poured into water (5 mL), acidified with 1 M aqueous HCl, and extracted with ethyl acetate (10.0 mL×2). The organic phase was washed with brine (20.0 mL), dried over sodium sulfate, filtered, and concentrated under reduced pressure to give a residue. The residue was purified by chromatography. 4-(1-(4-(N,N-dipropylsulfamoyl)-phenyl)piperidin-4-yl)butanoic acid BT0135 (0.53 mmol, 53% yield) was obtained as a white solid. MS: m/z=411 $(M+H)^+$.

$PEG_{2000}$ amide BT0138 was prepared by adapting the general procedure of Scheme 1 for PEG amidation using $NH_2$-$PEG_{2000}$ as indicated in Scheme 4. Reaction details are found in the table below. BT0138 was obtained as a white solid (1.40 g) in 48% yield. MS (ESI)=2408 (average MW).

| S. No. | Reaction | Scale | Conditions | Yield | Comments |
|---|---|---|---|---|---|
| 1 | 1 to 3 | 5.0 g | Compound 1 (1.0 equiv.), Compound 2 (3.2 equiv.), rt, 2 h | 6.20 g (92%) | Compound 1 consumed; TLC showed formation of new spot; after work-up crude was used as such for next reaction; $^1H$ NMR and LCMS consistent |
| 2 | 3 to BT0135 | 250 mg | Compound 3 (1.0 equiv.), Compound 4 (1.1 equiv.), $Cs_2CO_3$ (4 equiv.), DMSO, 90° C., 16 h | 140 mg (36%) | Compound 3 consumed; TLC showed formation of new spot; after work-up crude was purified by combi-flash chromatography eluted with 10-50% EtOAc in hexanes; $^1H$ NMR and LCMS consistent |
| 3 | 3 to BT0135 | 2.0 g | Compound 3 (1.0 equiv), Compound 4 (1.1 equiv.), $Cs_2CO_3$ (4 equiv.), DMSO, 90° C., 16 h | 1.70 g (53%) | Compound 3 consumed; TLC showed formation of new spot; after work-up crude was purified by combi-flash chromatography eluted with 10-50% EtOAc in hexanes; $^1H$ NMR and LCMS consistent; HPLC analysis is under progress |

-continued

| S. No. | Reaction | Scale | Conditions | Yield | Comments |
|---|---|---|---|---|---|
| 4 | BT0135 to BT0138 | 500 mg | Compound BT0135 (1.0 equiv.), $PEG_{2000}$-$NH_2$ (1.2 equiv.), BOP (1.2 equiv.), $Et_3N$ (2 equiv.), $CH_2Cl_2$, rt, 16 h | 1.40 g (48%) | Compound 3 consumed; TLC showed formation of new spot; after work-up crude was purified by combi-flash chromatography eluted with 5-10% MeOH in DCM; $^1H$ NMR and LCMS consistent; HPLC analysis is under progress |

Scheme 5 - Synthesis of BT136 (also referred to as BT0136) and BT139 (also referred to as BT0139)

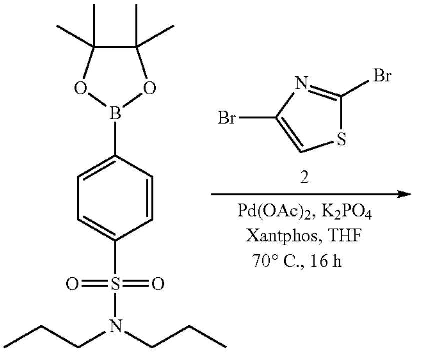

1

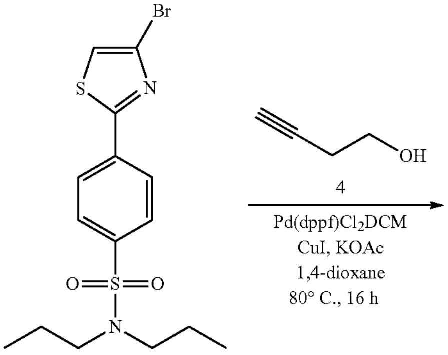

3

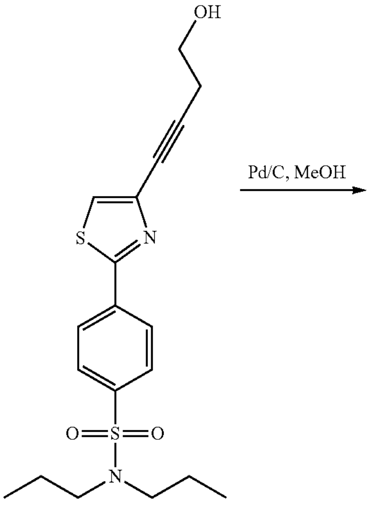

5

-continued

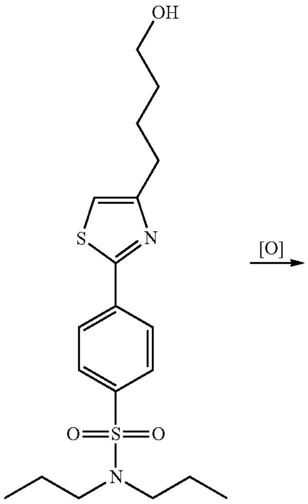

6

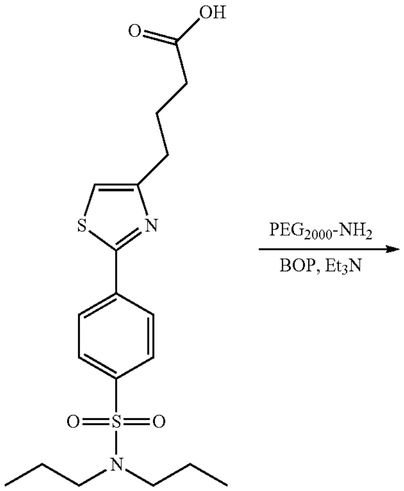

BT0136

-continued

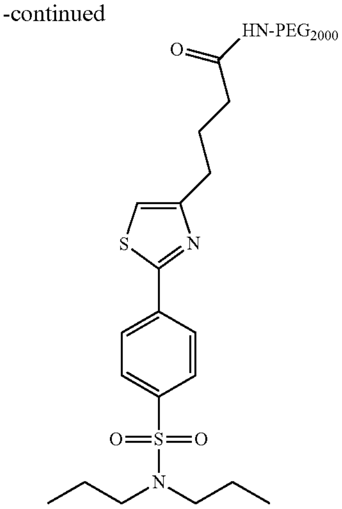

BT0139

Compound 3 of Scheme 5 was prepared by adapting the general procedure for Suzuki coupling in Scheme 1 using the boronic ester 1 and the dibromothiazole 2. Reaction details are in the table below.

Preparation of BT0136. To an ice-cold solution of alcohol 6 (Scheme 5; 1.0 mmol, 1.0 eq) in acetonitrile (1.5 mL) was added an excess of freshly prepared Jones reagent (2.67 molar; 0.5 mL). The reaction mixture was stirred at 0-5° C. for 2 h. The reaction mixture was poured into ice water (5 mL) and extracted with ethyl acetate (10.0 mL×2). The combined organic layers were washed with brine (10.0 mL×2), dried over $Na_2SO_4$, filtered, and concentrated under reduced pressure to give a residue. The residue was purified by chromatography. 4-(2-(4-(N,N-dipropylsulfamoyl)phenyl)thiazol-4-yl)butanoic acid BT0136 (0.3 mmol, 31% yield) was obtained as a white solid. MS: m/z=411 $(M+H)^+$.

$PEG_{2000}$ amide BT0139 was prepared by adapting the general procedure of Scheme 1 for PEG amidation using $NH_2$-$PEG_{2000}$ as indicated in Scheme 5. Reaction details are found in the table below. BT0139 was obtained as a white solid (160 mg) in 28% yield. MS (ESI)=2408 (average MW).

| S. No. | Reaction | Lot | Scale | Conditions | Yield | Comments |
|---|---|---|---|---|---|---|
| 1 | 3 to 5 | IN-PSN-C-34 | 100 mg | Compound 3 (1.0 equiv.), Compound 4 (1.3 equiv.), $Pd(dppf)Cl_2$•$CH_2Cl_2$ (0.2 equv.), CuI (0.5 equiv.), $Et_3N$ (3 equiv.), 1,4-dioxane rt to 80° C., in sealed tube 16 h | 60 mg (55%) | Compound 3 consumed; TLC showed formation of new spot; after work-up crude was purified by combi-flash chromatography eluted with 40-60% EtOAc in hexane; $^1H$ NMR consistent |
| 2 | 5 to 6 | IN-PSN-C-34 | 50 mg | Compound 5 (1.0 equiv.), 10% Pd/C (25 mg), H2 bladder, methanol rt 16 h | 30 mg (50%) | Compound 6 consumed; TLC showed formation of new spot; after work-up crude was purified by combi-flash chromatography eluted with 40-60% EtOAc in hexane; $^1H$ NMR consistent |
| 3 | 1 to 3 | IN-PSN-C-35 | 2.5 g | Compound 1 (1.0 equiv.), Compound 2 (1.2 equiv.), $Pd(OAc)_2$ (0.025 equiv.), Xaniphos (0.025 equiv, $K_3PO_4$ (3 equiv.), THF, sealed tube, rt to 70° C., 16 h | 2.5 g (80%) | Compound 1 & 2 consumed; TLC showed formation of new spot; after work-up crude was purified by combi-flash chromatography eluted with 20-30% EtOAc in hexanes; $^1H$ NMR consistent |
| 1 | 5 to 6 | IN-PSN-C-52 | 10.0 g | Compound 5 (1.0 equiv.), 10% Pd/C (25 mg), autoclave, $H_2$ (200 psi), MeOH, rt, 48 h | 7.50 g (74%) | Compound 5 consumed; TLC and UPLC showed formation of new spot; after filtration and concentration, crude was washed with hexanes; $^1H$ NMR consistent |
| 2 | BT0136 to BT0139 | IN-PSN-C-60 | 300 mg | Compound BT0136 (1.0 equiv.), $PEG_{(2000)}$-$NH_2$ (1.2 equiv.), BOP (1.2 equiv.), $Et_3N$ (2 equiv.), $CH_2Cl_2$, rt, 16 h | 500 mg (28%) | BT0136 consumed; TLC and UPLC showed formation of new spot; after work-up crude was purified by reverse phase combi-flash chromatography eluted with 40-80% ACN in water; analysis is under progress |
| 3 | 6 to BT0136 | IN-PSN-C-62 | 7.50 g | Compound 6 (1.0 equiv.), Jones reagent (0.5 mL, 2.67 molar), acetonitrile, 0° C.-5° C., 2 h | 2.40 g (31%) | Compound 6 consumed; TLC and UPLC showed formation of new spot; after work-up crude was purified by reverse phase combi-flash chromatography eluted with 5-10% MeOH in $CH_2Cl_2$; further it was washed with 10% EtOAc in hexanes; NMR, HPLC and UPLC consistent |

| S. No. | Reaction | Scale | Conditions | Yield | Comments |
|---|---|---|---|---|---|
| 1 | BT0136 to BT0139 | 300 mg | Compound BT0136 (1.0 equiv.), $PEG_{(2000)}$-$NH_2$ (1.2 equiv.), BOP (1.2 equiv.), $Et_3N$ (2 equiv.), $CH_2Cl_2$, rt, 16 h | 500 mg (28%) | BT0136 consumed; TLC and UPLC showed formation of new spot; after work-up crude was purified by reverse phase combi-flash chromatography eluted with 40-80% ACN in water; $^1H$ NMR, HPLC and UPLC consistent |
| 2 | 6 to BT0136 | 7.50 g | Compound 6 (1.0 equiv.), Jones reagent (0.5 mL, 2.67 molar), acetonitrile, 0° C.-5° C., 2 h | 2.40 g (31%) | Compound 6 consumed; TLC and UPLC showed formation of new spot; after work-up crude was purified by combi-flash chromatography eluted with 5-10% MeOH in $CH_2Cl_2$; further it was washed with 10% EtOAc in hexanes; $^1H$ NMR, HPLC and UPLC consistent |

Scheme 6 - Synthesis of BT137 (also referred to as BT0137) and BT140 (also referred to as BT0140)

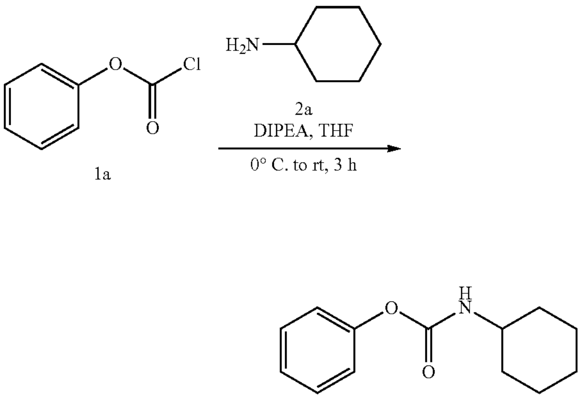

1a 2a 3a

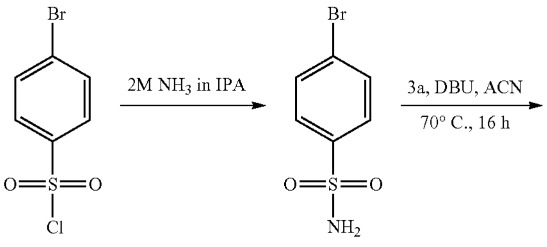

1 2

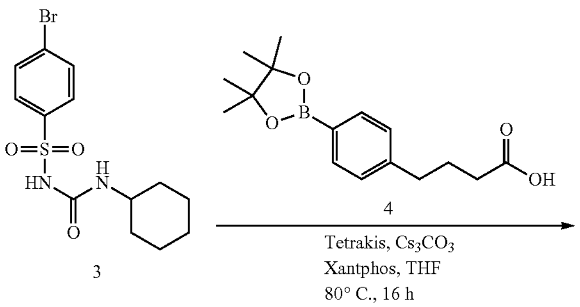

3 4

-continued

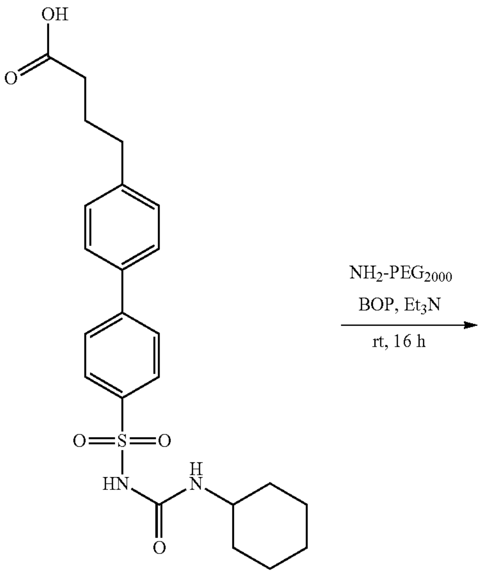

BT0137

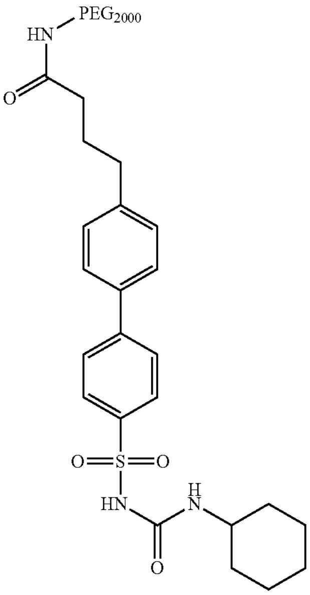

BT0140

Acid BT137 was prepared by adapting the general procedure of Scheme 1 for Suzuki coupling using the aryl bromide and boronic acid ester indicated in Scheme 6. Reaction details are found in the table below. BT0137 was obtained as a white solid in 89% yield. MS: m/z=445 $(M+H)^+$.

$PEG_{2000}$ amide BT0140 was prepared by adapting the general procedure of Scheme 1 for PEG amidation using $NH_2$-$PEG_{2000}$ as indicated in Scheme 6. Reaction details are found in the table below. BT0140 was obtained as a white solid (160 mg) in 33% yield. MS (ESI)=2442 (average MW).

| S. No. | Reaction | Scale | Conditions | Yield | Comments |
|---|---|---|---|---|---|
| 1 | 1a to 3a | 5.0 g | Compound 1a (1.0 equiv.), Compound 2a (1.1equiv,), DIPEA (1.2 equiv.), THF, 0° C. to RT, 3 h | 6.20 g (89%) | Compound 1 consumed; TLC showed formation of new spot; after work-up crude was washed with hexanes and dried, $^1H$ NMR and LCMS consistent |
| 2 | 2 to 3 | 500 mg | Compound 2 (1.0 equiv), Compound 3a (1.2 equiv.), DBU (1.5 equiv.), ACN, 70° C., 16 h | 600 mg (79%) | Compound 2 consumed; TLC showed formation of new spot; after work-up crude was purified by combi-flash chromatography eluted with 30-60% ethyl acetate in hexanes; $^1H$ NMR and LCMS consistent |
| 3 | 3 to BT0137 | 500 mg | Compound 3 (1.0 equiv), Compound 4 (1.1 equiv.), tetrakis (0.1 equiv.), $K_2CO_3$ (1.2 equiv.), 1,4-dioxane, 100° C., 16 h | 160 mg (89%) | Compound 3 consumed; TLC showed formation of new spot; after work-up crude was purified by combi-flash chromatography eluted with 5-10% MeOH in $CH_2Cl_2$; further it was purified by reverse phase combi-flash chromatography eluted with 40-80% ACN in water; $^1H$ NMR consistent |

Scheme 7 - Synthesis of BT004

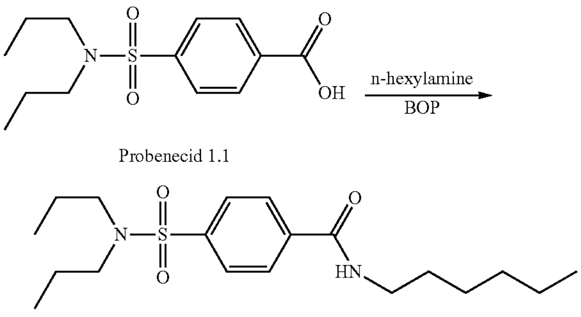

Probenecid 1.1

BT004

To a solution of acid probenecid 1.1 (Cayman Chemical Company, 1180 East Ellsworth Rd., Ann Arbor, MI, 48108; 1 mmol, 1.0 eq) and n-hexylamine (1.2 eq) in dichloromethane (3.0 mL) was added benzotriazol-1-yloxytris(dimethylamino)phosphonium hexafluorophosphate (BOP, 1.2 eq) and diisopropylethylamine (2.0 mmol, 2 eq). The reaction mixture was stirred at 25° C. for 16 h. The reaction mixture was poured into water and extracted with ethyl acetate (10 mL×2). The combined organic layers were washed sequentially with 1 M aqueous hydrochloric acid (HCl; 10 mL), saturated aqueous sodium bicarbonate ($NaHCO_3$; 10 mL), brine (10 mL×2), dried over sodium sulfate (sodium sulfate), filtered, and concentrated under reduced pressure to give a residue. The residue was purified by chromatography. 4-(N,N-Dipropylsulfamoyl)-N-hexylbenzamide BT004 (0.89 mmol, 89% yield) was obtained as a white solid. MS: m/z=370 $(M+H)^+$.

Scheme 8 - Synthesis of BT030

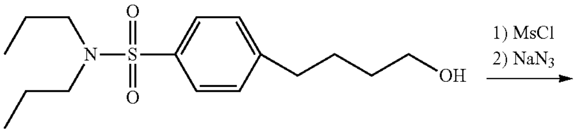

Alcohol 2.1

-continued

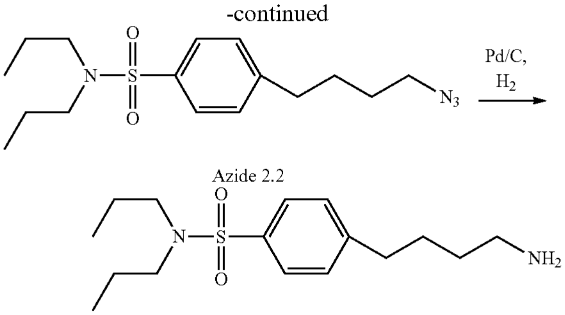

Azide 2.2

BT030

To a cold solution of alcohol 2.1 (Intonation Research Laboratories, A-1B, Chilka Nagar Main Rd, Industrial Development Area, Nacharam, Secunderabad, Telangana 500076, India; 1 mmol, 1.0 eq) in dichloromethane (DCM; 5 mL) was added and triethylamine (2 q) followed by methane sulfonyl chloride (MsCl, 1.2 eq). The reaction mixture was stirred at 5° C. for 3 h. The reaction mixture was poured into water and extracted with ethyl acetate (10 mL×2). The combined organic layers were washed sequentially with 1 M aqueous hydrochloric acid (HCl; 10 mL), saturated aqueous sodium bicarbonate ($NaHCO_3$; 10 mL), brine (10 mL×2), dried over sodium sulfate (sodium sulfate), filtered, and concentrated under reduced pressure to give the corresponding methane sulfonate. The crude sulfonate was dissolved in dimethylformamide (5 mL) and the solution chilled. Sodium azide ($NaN_3$; 2 eq) was then added and the reaction mixture was stirred at 60° C. for 6 h. The reaction mixture was poured into water and extracted with ethyl acetate (10 mL×2). The combined organic layers were washed sequentially with 1 M aqueous hydrochloric acid (HCl; 10 mL), saturated aqueous sodium bicarbonate ($NaHCO_3$; 10 mL), brine (10 mL×2), dried over sodium sulfate (sodium sulfate), filtered, and concentrated under reduced pressure to give the corresponding azide 2.2. Compound 2.2 was used directly in the next reaction. Azide 2.2 was dissolved in ethanol (10 mL) and 10% palladium on carbon (Pd/C; 0.3 eq). The reaction mixture was stirred under an atmosphere of hydrogen gas at ambient temperature and pressure for 12 h. The reaction mixture was filtered to remove the Pd/C catalyst, the solvent was removed under reduced pressure to give a residue which was purified by chromatography. 4-(4-Aminobutyl)-N,N-dipropylbenzenesulfonamide BT030 (0.45 mmol, 45% yield) was obtained as a white solid. MS: m/z=389 (M−H).

Scheme 9 - Synthesis of BT031

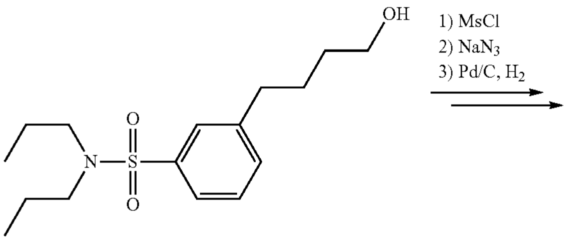

Alcohol 3.1

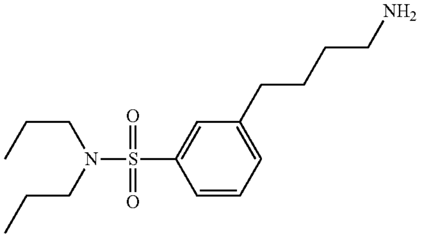

BT031

The same reaction conditions used to prepare BT030 were applied to the synthesis of BT031 starting with alcohol 3.1. 3-(4-Aminobutyl)-N,N-dipropylbenzenesulfonamide BT030 was obtained as a white solid. MS: m/z=389 (M−H).

Scheme 10 - Synthesis of BT053

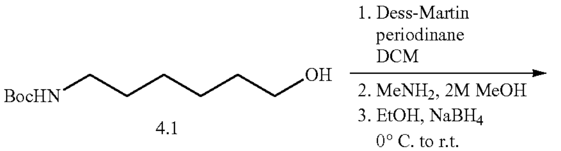

4.1

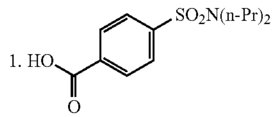

1.1

HATU, $Et_3N$

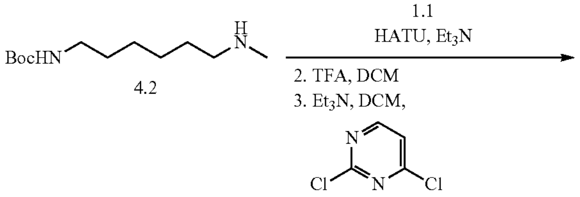

4.2

-continued

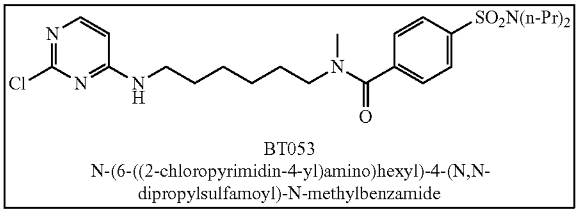

BT053

N-(6-((2-chloropyrimidin-4-yl)amino)hexyl)-4-(N,N-dipropylsulfamoyl)-N-methylbenzamide tert-Butyl (6-(methylamino)hexyl)carbamate (4.2). To a solution of tert-butyl (6-hydroxyhexyl)carbamate 4.1 (4.0 g, 18.4 mmol) in DCM (100 mL) at 0° C. was added the periodinane (9.37 g, 22.0 mmol) and the resulting mixture was stirred for 2 h. The reaction was then quenched with a saturated solution of sodium bisulfate (100 mL) and a saturated solution of $NaHCO_3$ (100 mL). The phases were separated, and the aqueous phase was extracted with DCM (100 mL). Organic phases were combined and dried over $MgSO_4$, filtered and concentrated under reduced pressure to afford the crude aldehyde. Freshly prepared aldehyde in EtOH (80 mL) was stirred at room temperature. After 2 min, the MeNH2 2M in MeOH (73 mL) was added, and the mixture vigorously stirred. After stirring for 3 h, the resulting mixture was cooled down to 0° C. and $NaBH_4$ (731 mg, 19.3 mmol) was added. The reaction was stirred for 30 min and the resulting mixture was quenched with a saturated solution of $NaHCO_3$ and the organic material was extracted with DCM (3×300 mL), dried over sodium sulfate and concentrated under reduced pressure affording crude 4.2 (4.2 g, 99%). LC-MS: RT=1.09 min; MS cal.: 230.35; Mass found: [M-Boc+H]: 175.0. $^1H$ NMR (500 MHz, $CDCl_3$) δ 4.51 (s, 1H), 3.10 (d, J=6.0 Hz, 2H), 2.64-2.52 (m, 2H), 2.43 (s, 3H), 1.54-1.46 (m, 4H), 1.44 (s, 9H), 1.33 (dd, J=6.7, 2.9 Hz, 4H).

N-(6-(2-Chloropyrimidin-4-yl)amino)hexyl)-4-(N,N-dipropylsulfamoyl)-N-methylbenzamide (BT053). Triethylamine (10.3 mL, 73.6 mmol) was added to a solution of 4-(N,N-dipropylsulfamoyl)benzoic acid 1.1 (5.25 g, 18.4 mmol) dissolved in DMF (46.0 mL). Then HATU (7.07 g, 18.4 mmol) was added in the mixture at 0° C. and stirred for 5 min. A solution of tert-butyl (6-(methylamino)hexyl)carbamate 4.2 (4.24 g, 18.4 mmol) was added dropwise over 15 min to the mixture at 0° C. and the reaction was allowed to slowly warm up to room temperature and stirred for 18 h. Then EtOAc (50 mL) and water (50 mL) were added, the organic layer was washed with water (2×50 mL), washed with a saturated solution of $NaHCO_3$ (1×50 mL), washed with brine, dried over anhydrous sodium sulfate and concentrated under reduced pressure affording crude Boc protected amine (8.0 g, 93%) and was used without purification for the next step. LC-MS: RT=1.86 min; MS cal.: 497.69; Mass found: [M-Boc+H]: 398.3. Trifluoroacetic acid (11.4 mL, 148 mmol) was added to a solution of crude dissolved in DCM (36.9 mL). The reaction was stirred for 5 h at room temperature. The reaction was followed by LC-MS and starting material was still present. Trifluoroacetic acid (2.0 mL) was added and the reaction stirred for 18 h. The mixture was washed with a saturated solution of $NaHCO_3$ (2×20 mL), dried over anhydrous sodium sulfate and concentrated under reduced pressure affording the crude amine (7.65 g) and was used without purification for the next step. LC-MS: RT=1.34 min; MS cal.: 397.58; Mass found: [M+H]: 398.3. 2,4-Dichloropyrimidine (3.64 g, 23.9 mmol) was added to a solution of crude and triethylamine (20.6 mL, 147 mmol) dissolved in DCM (46.0 mL). The reaction was stirred for 3 h at 0° C. (the reaction was followed by LCMS and wasn't yet completed), Et3N (4.0 mL) was added and the resulting mixture was stirred for 18 h at room temperature. Then water (40 mL) was added and extracted with EtOAc (2×40 mL), washed with brine, dried over anhydrous sodium sulfate and concentrated under reduced pressure. The crude was purified by flash column chromatography (220 g silica, EtOAc in hexanes, 15 to 100%) affording compound BT053 (5.09 g, 54%) as a yellow oil. LC-MS: RT=1.73 min; Purity: 98.9%; MS cal.: 510.09; Mass found: [M+H]: 510.3. $^{1}$H NMR (500 MHz, CDCl3) δ 7.99 (s, 1H), 7.85 (d, J=8.1 Hz, 2H), 7.50 (d, J=7.9 Hz, 2H), 6.26 (d, J=6.0 Hz, 1H), 5.31 (s, 1H), 3.56 (t, J=6.9 Hz, 1H), 3.22-3.13 (m, 2H), 3.09 (s, 6H), 2.96 (s, 3H), 2.89 (d, J=11.7 Hz, 2H), 1.84-1.46 (m, 12H), 0.88 (t, J=7.4 Hz, 6H).

Scheme 11 - Synthesis of BT054

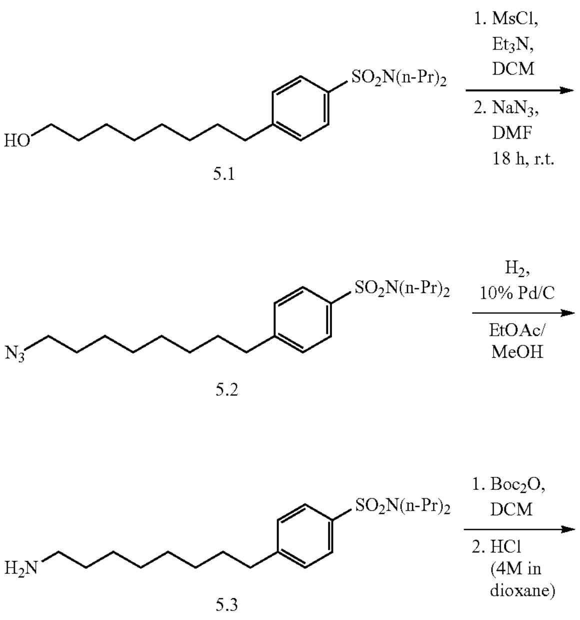

5.1

5.2

5.3

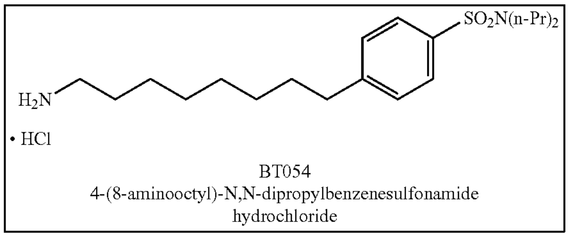

BT054
4-(8-aminooctyl)-N,N-dipropylbenzenesulfonamide hydrochloride 4-(8-Azidooctyl)-N,N-dipropylbenzenesulfonamide (5.2). Methanesulfonyl chloride (1.53 mL, 19.6 mmol) was added to a solution of 4-(8-hydroxyoctyl)-N,N-dipropylbenzenesulfonamide 5.1 (4.84 g, 13.1 mmol) and triethylamine (3.67 mL, 26.2 mmol) dissolved in DCM (43.7 mL) at 0° C. The reaction was stirred for 30 min at 0° C. and 30 min at room temperature. Then water (30 mL) was added and extracted with EtOAc (2×30 mL), washed with brine, dried with anhydrous sodium sulfate and concentrated under reduced pressure affording the crude mesylate as a yellow oil. LC-MS: RT=2.08 min; MS cal.: 447.65; Mass found: [M+H]: 448.4. $^{1}$H NMR (400 MHz, $CDCl_3$) δ 7.71 (d, J=8.4 Hz, 2H), 7.48 (d, J=8.4 Hz, 2H), 4.24 (t, J=6.5 Hz, 2H), 3.12-3.03 (m, 4H), 3.00 (s, 3H), 2.44 (t, J=7.0 Hz, 2H), 1.84-1.75 (m, 2H), 1.69-1.59 (m, 2H), 1.55-1.43 (m, 8H), 0.86 (t, J=7.4 Hz, 6H). Sodium azide (1.71 mL, 26.2 mmol) was added to a solution of crude mesylate (13.1 mmol) dissolved in DMF (65.5 mL). The reaction was stirred for 18 h at room temperature. Then EtOAc (30 mL) and water (30 mL) were added, the organic phase was washed with water (3×30 mL), washed with brine, dried over anhydrous sodium sulfate and concentrated under reduced pressure. The crude was purified by flash column chromatography (100 g silica, 1 to 20% EtOAc/Hexanes) affording azide 5.2 (3.65 g, 71% over 2 steps) as a colourless oil. LC-MS: RT=2.32 min; MS cal.: 394.67; Mass found: [M-N2]: 367.4. $^{1}$H NMR (400 MHz, $CDCl_3$) δ 7.70 (d, J=8.3 Hz, 2H), 7.28 (d, J=8.3 Hz, 2H), 3.25 (t, J=6.9 Hz, 2H), 3.10-3.00 (m, 4H), 2.69-2.61 (m, 2H), 1.70-1.45 (m, 8H), 1.42-1.28 (m, 8H), 0.87 (t, J=7.4 Hz, 6H).

4-(8-Aminooctyl)-N,N-dipropylbenzenesulfonamide (5.3). Palladium, 10% weight on activated carbon (150 mg) was added to a solution of 4-(8-azidooctyl)-N,N-dipropylbenzenesulfonamide 5.2 (1.45 g, 3.67 mmol) dissolved in EtOAc (36.9 mL) and MeOH (3.69 mL). After flushing (×3) the resulting mixture and adding hydrogen with a balloon, the reaction was stirred for 2 h at room temperature under hydrogen atmosphere. The mixture was filtered over Celite (MeOH was used for the washing) and concentrated under reduced pressure affording crude amine 5.3 (1.23 g, 91%) as a yellow oil. LC-MS: RT=1.57 min; MS cal.: 368.58; Mass found: [M+H]: 369.3.

4-(8-Aminooctyl)-N,N-dipropylbenzenesulfonamide hydrochloride (BT054 HCl salt). Di-tert-butyldicarbonate (1.53 mL, 6.67 mmol) was added to a solution of crude 5.3 (1.23 g, 3.34 mmol) dissolved in DCM (16.7 mL). The reaction was stirred for 30 min at room temperature. The resulting mixture was concentrated under reduced pressure and purified by flash column chromatography (100 g silica, 5 to 35% EtOAc/Hexanes) affording the Boc protected amine (1.45 g, 93%) as a yellow oil. LC-MS: RT=2.24 min; MS cal.: 468.69; Mass found: [M-Boc+H]: 369.4. Hydrochloric acid (3.09 mL, 12.4 mmol) (4 M solution in dioxane) was added to a solution of the Boc protected amine (1.45 g, 3.09 mmol). The reaction was stirred for 1 h at room temperature. Air was flushed in the flask to concentrate the resulting mixture affording BT054 HCl salt (1.20 g, 96%) as a white solid. LC-MS: RT=1.64 min; Purity: 95.5%; MS cal.: 405.04; Mass found: [M-Cl]: 369.2. $^{1}$H NMR (500 MHz, $CDCl_3$) δ 8.28 (s, 3H), 7.69 (d, J=8.2 Hz, 2H), 7.27 (d, J=7.6 Hz, 2H), 3.08-3.03 (m, 4H), 2.95 (m, 2H), 2.64 (t, J=7.7 Hz, 2H), 1.80-1.71 (m, 2H), 1.64-1.59 (m, 2H), 1.54 (dq, J=14.9, 7.5 Hz, 4H), 1.42-1.35 (m, 2H), 1.30 (s, 6H), 0.86 (t, J=7.4 Hz, 6H).

Scheme 12 - Synthesis of BT055

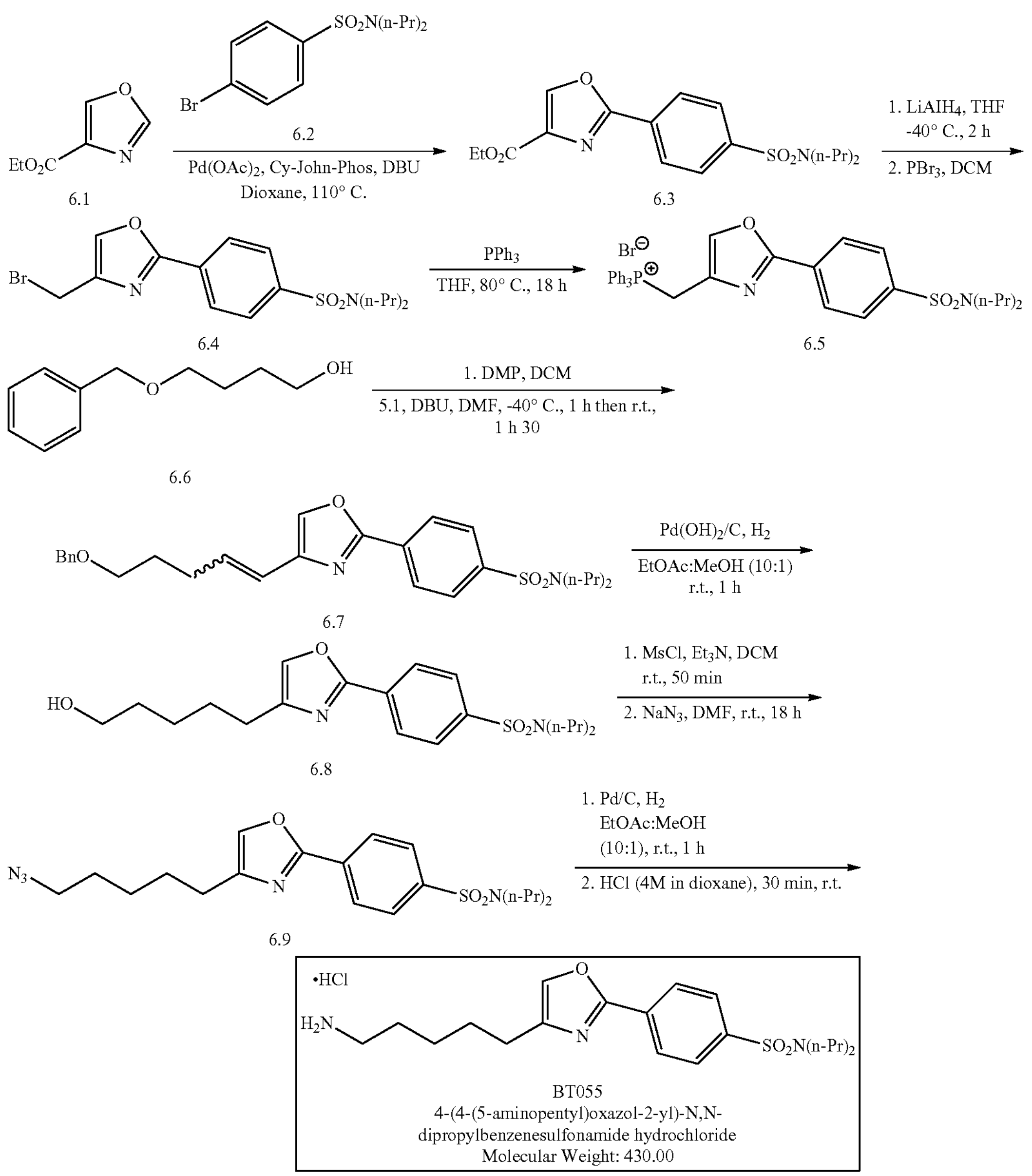

Ethyl 2-(4-(N,N-dipropylsulfamoyl)phenyl)oxazole-4-carboxylate (6.3). Ethyl oxazole-4-carboxylate 6.1 (4.0 g, 28 mmol) was placed in a sealed tube (250 mL) with DBU (8.47 mL, 57 mmol), $Pd(OAc)_2$ (318.2 mg, 1.4 mmol) and Cy-John-Phos ligand (994 mg, 2.8 mmol). A solution of bromide 6.2 (9.0 g, 28 mmol) in dry dioxane (80 mL) was added and the resulting mixture was purged with nitrogen for a period of 10 min. The mixture was stirred at 110° C. for 18 h. After filtration through Celite and concentration in vacuo, the crude product was purified by flash column chromatography (330 g silica, 5 to 35% EtOAc/Hexanes) affording 6.3 (6.70 g, 62%) as a white powder. LC-MS: RT=1.86 min; MS cal.: 380.46; Mass found: [M+H]: 381.2. $^1H$ NMR (400 MHz, $CDCl_3$) δ 8.32 (s, 1H), 8.25-8.22 (m, 2H), 7.93-7.88 (m, 2H), 4.44 (q, J=7.1 Hz, 2H), 3.14-3.07 (m, 4H), 1.57-1.49 (m, 4H), 1.42 (t, J=7.1 Hz, 3H), 0.87 (t, J=7.4 Hz, 6H).

4-(4-(Bromomethyl)oxazol-2-yl)-N,N-dipropylbenzenesulfonamide (6.4). Lithium aluminum hydride (10.1 mL, 20.1 mmol, 2.0 M in THF) was added dropwise over 10 min to a solution of ethyl 2-(4-(N,N-dipropylsulfamoyl)phenyl)oxazole-4-carboxylate 6.3 (3.83 g, 10.1 mmol) dissolved in THF (101 mL) at −40° C. (using a bath of dry ice and acetonitrile) under argon atmosphere. The reaction was stirred for 2 h at −40° C. Then a solution of sat. Rochelle salt (30 mL) was added in the reaction mixture at −40° C., anhydrous sodium sulfate was added and the mixture was vigorously agitated at room temperature. The mixture was filtered and concentrated under reduced pressure affording crude alcohol (3.17 g, 93%) as a yellow solid. LC-MS: RT=1.56 min; MS cal.: 338.42; Mass found: [M+H]: 339.3. Phosphorus tribromide (1.78 mL, 18.7 mmol) was added dropwise to a solution of crude alcohol (3.17 g, 9.37 mmol) dissolved in DCM (62.4 mL) at 0° C. The reaction was stirred at this temperature for 1 h. The mixture was stirred at room temperature for 4 h. Then water (50 mL) was added and extracted with EtOAc (2×50 mL), washed with brine, dried over anhydrous sodium sulfate, filtered and concentrated under reduced pressure. The crude was purified with a silica pad (30% EtOAc/Hexanes) affording 6.4 (2.68 g, 71%) as a yellow powder. LC-MS: RT=1.91 min; MS cal.: 401.32; Mass found: [M+H]: 403.0.

((2-(4-(N,N-dipropylsulfamoyl)phenyl)oxazol-4-yl) methyl)triphenylphosphonium bromide (6.5). Triphenylphosphine (1.47 g, 5.61 mmol) was added to a solution of 6.4 (2.25 g, 5.61 mmol) dissolved in THF (22.4 mL). The reaction was refluxed for 18 h. Then the resulting mixture was concentrated under reduced pressure affording crude 6.5 (3.73 g, 100%) as a pale yellow solid. The material was used in the next step without purification. LC-MS: RT=1.80 min; MS cal.: 663.60; Mass found: [M-Br]: 583.4. $^1$H NMR (500 MHz, $CDCl_3$) δ 8.48 (d, J=4.4 Hz, 1H), 7.90 (ddt, J=9.4, 3.6, 1.3 Hz, 8H), 7.84-7.76 (m, 5H), 7.69-7.64 (m, 6H), 5.60 (d, J=14.0 Hz, 2H), 3.13-3.04 (m, 4H), 1.60-1.50 (m, 4H), 0.87 (t, J=7.4 Hz, 6H).

4-(4-(5-(Benzyloxy)pent-1-en-1-yl)oxazol-2-yl)-N,N-dipropylbenzenesulfonamide (6.7). Dess-martin periodinane (2.91 g, 6.73 mmol) was added to a solution of 4-(benzyloxy)butan-1-ol 6.6 (987 μL, 5.61 mmol) dissolved in DCM (28.1 mL) at 0° C. The reaction was stirred at room temperature for 1 h 30 min. Then a sat. solution of $NaHCO_3$ (50 mL) and a sat. solution of $Na_2S_2O_3$ (50 mL) were added and the resulting mixture was stirred for 30 min, extracted with DCM (2×50 mL), washed with brine, dried over anhydrous sodium sulfate and concentrated under reduced pressure affording crude aldehyde as a yellow oil. The crude was used in the next step reaction without purification. 1,8-diazabicyclo[5.4.0]undec-7-ene (DBU) (1.28 mL, 8.42 mmol) was added to a solution of crude aldehyde and phosphonium salt 6.5 (3.72 g, 5.61 mmol) dissolved in DMF (28.1 mL) at −40° C. under argon. The reaction was stirred at this temperature for 1 h then at r.t. for 1 h 30 min. Then water (50 mL) and EtOAc (50 mL) were added, washed with water (2×50 mL), washed with brine (×2), dried over anhydrous sodium sulfate and concentrated under reduced pressure. The crude was purified by flash column chromatography (silica 100 g, 10 to 100% EtOAc/hexanes) affording 6.7 (1.78 g, 66%) as a yellow oil. LC-MS: RT=2.25 min; MS cal.: 482.63; Mass found: [M+H]: 483.4. $^1$H NMR (500 MHz, CDCl3) δ 8.20-8.13 (m, 2H), 7.91-7.83 (m, 2H), 7.74 (s) and 7.57 (s) (1H, E/Z isomers), 7.37-7.31 (m, 5H), 6.56 (dt, J=15.6, 7.0 Hz, 0.5H), 6.27 (ddd, J=13.5, 5.3, 3.9 Hz, 1H), 5.83 (dt, J=11.5, 7.4 Hz, 0.5H), 4.52 (s, 2H), 3.55 (dt, J=11.4, 6.4 Hz, 2H), 3.14-3.08 (m, 4H), 2.60 (qd, J=7.5, 1.6 Hz, 1H), 2.34 (q, J=6.9 Hz, 1H), 1.89-1.77 (m, 2H), 1.60-1.50 (m, 4H), 0.87 (td, J=7.4, 2.8 Hz, 6H).

4-(4-(5-Hydroxypentyl)oxazol-2-yl)-N,N-dipropylbenzenesulfonamide (6.8). Palladium hydroxide (20 wt. % Pd on carbon wet, 178 mg) was added to a solution of 6.7 (1.78 g, 3.69 mmol) dissolved in MeOH (3.35 mL) and EtOAc (33.5 mL). After flushing (×3) the resulting mixture and adding hydrogen with a balloon, the reaction was stirred for 1 h at room temperature under hydrogen atmosphere. The mixture was filtered over Celite (EtOAc was used for the washing) and concentrated under reduced pressure affording crude alcohol 6.8 (1.11 g, 76%) as a white solid. LC-MS: RT=1.75 min; MS cal.: 394.53; Mass found: [M+H]: 395.3. $^1$H NMR (500 MHz, CDCl3) δ 8.12 (d, J=8.5 Hz, 2H), 7.86 (d, J=8.5 Hz, 2H), 7.47 (s, 1H), 3.65 (t, J=6.5 Hz, 2H), 3.14-3.03 (m, 4H), 2.60 (t, J=7.5 Hz, 2H), 1.72 (dt, J=15.4, 7.7 Hz, 2H), 1.66-1.58 (m, 2H), 1.53 (m, 4H), 1.50-1.42 (m, 2H), 0.86 (t, J=7.4 Hz, 6H).

4-(4-(5-Azidopentyl)oxazol-2-yl)-N,N-dipropylbenzenesulfonamide (6.9). Methanesulfonyl chloride (885 μL, 11.4 mmol) was added to a solution of 6.8 (3.00 g, 7.60 mmol) and triethylamine (2.13 mL, 15.2 mmol) dissolved in DCM (38.0 mL) at 0° C. The reaction was stirred at this temperature for 10 min and at r.t. for 50 min. Then water (50 mL) was added, extracted with EtOAc (2×50 mL), washed with brine, dried over anhydrous sodium sulfate and concentrated under reduced pressure affording crude mesylate as a yellow oil. The crude was used in the next step without purification. LC-MS: RT=1.90 min; MS cal.: 472.62; Mass found: [M+H]: 473.3. Sodium azide (993 μL, 15.2 mmol) was added to a solution of crude mesylate (7.60 mmol) dissolved in DMF (38.0 mL). The reaction was stirred for 18 h at room temperature. Then EtOAc (50 mL) and water (50 mL) were added, washed with water (3×50 mL), washed with brine, dried over anhydrous sodium sulfate and concentrated under reduced pressure. The crude was purified by flash column chromatography (silica 100 g, 5 to 100% EtOAc/hexanes) affording 6.9 (2.61 g, 82% over 2 steps) as a colourless oil. LC-MS: RT=2.12 min; MS cal.: 419.54; Mass found: [M+H]: 420.3. $^1$H NMR (500 MHz, $CDCl_3$) δ 8.14 (d, J=8.6 Hz, 2H), 7.88 (d, J=8.6 Hz, 2H), 7.49 (s, 1H), 3.29 (t, J=6.9 Hz, 2H), 3.14-3.06 (m, 4H), 2.62 (t, J=7.3 Hz, 2H), 1.78-1.44 (m, 10H), 0.87 (t, J=7.4 Hz, 6H).

4-(4-(5-Aminopentyl)oxazol-2-yl)-N,N-dipropylbenzenesulfonamide hydrochloride (BT055 HCl salt). Palladium (10% wt on activated carbon, 261 mg) was added to a solution of 6.9 (2.61 g, 6.22 mmol) dissolved in MeOH (5.66 mL) and EtOAc (56.6 mL). After flushing (×3) the resulting mixture and adding hydrogen with a balloon, the reaction was stirred for 1 h at room temperature under hydrogen atmosphere. The mixture was filtered over Celite (EtOAc was used for the washing) and concentrated under reduced pressure affording crude amine. Then a solution of hydrochloric acid (4 M in dioxane, 3 eq.) was added and the reaction was stirred for 30 min at r.t. The resulting mixture was concentrated under reduced pressure, agitated in MTBE and filtered affording BT055 HCl salt (2.33 g, 87%) as a white solid. LC-MS: RT=1.48 min; Purity: 97.02%; MS cal.: 430.00; Mass found: [M-Cl]: 394.3. $^1$H NMR (500 MHz, $CDCl_3$) δ 8.35 (s, 3H), 8.28 (d, J=8.5 Hz, 2H), 7.92 (d, J=8.6 Hz, 2H), 7.65 (s, 1H), 3.10 (dd, J=8.6, 6.7 Hz, 4H), 3.01 (m, 2H), 2.70 (t, J=7.5 Hz, 2H), 1.81 (m, 4H), 1.54 (m, 6H), 0.86 (t, J=7.4 Hz, 6H).

Scheme 13 - Synthesis of BT056

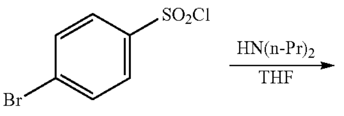

7.1

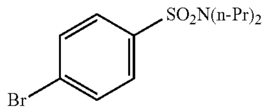

7.2

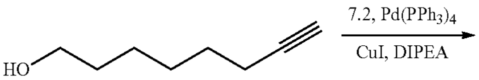

7.3

-continued

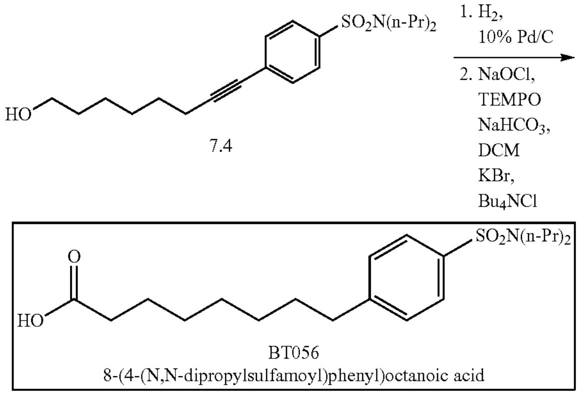

7.4

BT056

8-(4-(N,N-dipropylsulfamoyl)phenyl)octanoic acid

4-Bromo-N,N-dipropylbenzenesulfonamide (7.2). Dipropylamine (31.9 mL, 230 mmol) was added to a solution of 4-bromobenzenesulfonyl chloride 7.1 (20.0 g, 76.7 mmol) dissolved in THF (153 mL) at 0° C. The reaction was stirred for 1 h at room temperature. Then a saturated solution of $NH_4Cl$ (50 mL) was added, extracted with EtOAc (2×50 mL), washed with brine, dried over sodium sulfate and concentrated under reduced pressure affording compound 7.2 (24.6 g, 100% yield) as a white solid. LC-MS: RT=1.95 min; MS cal.: 320.25; Mass found: [M+H]: 320.1. $^1$H NMR (400 MHz, $CDCl_3$) δ 7.70-7.59 (m, 4H), 3.10-3.03 (m, 4H), 1.60-1.50 (m, 4H), 0.87 (t, J=7.4 Hz, 6H).

4-(8-Hydroxyoct-1-yn-1-yl)-N,N-dipropylbenzenesulfonamide (7.4). Tetrakis (triphenylphosphine)palladium(O) (5.17 g, 4.39 mmol) was added to a solution of oct-7-yn-1-ol 7.3 (4.52 g, 35.1 mmol), 4-bromo-N,N-dipropylbenzenesulfonamide 7.2 (5.62 g, 17.6 mmol) and CuI (3.34 g, 17.6 mmol) dissolved in diisopropylethylamine (88.0 mL). The reaction was stirred for 2 h at 150° C. Then EtOAc (50 mL) and a saturated solution of $NH_4Cl$ (50 mL) were added, extracted with EtOAc (2×50 mL), washed with brine, dried over anhydrous sodium sulfate and concentrated under reduced pressure. The crude was purified by flash column chromatography (220 g, EtOAc in hexanes, 5 to 100%) affording compound 7.4 (4.80 g, 75%) as a yellow oil. LC-MS: RT=1.91 min; MS cal.: 365.53; Mass found: [M+H]: 366.3. $^1$H NMR (400 MHz, CDCl3) δ 7.71 (d, J=8.5 Hz, 2H), 7.48 (d, J=8.5 Hz, 2H), 3.66 (t, J=6.6 Hz, 2H), 3.11-3.02 (m, 4H), 2.43 (t, J=7.0 Hz, 2H), 1.73-1.36 (m, 12H), 0.86 (t, J=7.4 Hz, 6H).

8-(4-(N,N-Dipropylsulfamoyl)phenyl)octanoic acid (BT056). Palladium 10% wt on activated carbon (1.11 g, 13.1 mmol) was added to a solution of 4-(8-hydroxyoct-1-yn-1-yl)-N,N-dipropylbenzenesulfonamide 7.4 dissolved in MeOH (87.5 mL). After flushing (×3) the resulting mixture and adding hydrogen with a balloon, the reaction was stirred for 2 h at room temperature under hydrogen atmosphere. The mixture was filtered over Celite® (MeOH was used for the washing) and concentrated under reduced pressure affording crude alcohol (4.32 g, 89%) as a colourless oil. LC-MS: RT=1.98 min; MS cal.: 369.56; Mass found: [M+H]: 370.3. $^1$H NMR (400 MHz, $CDCl_3$) δ 7.69 (d, J=8.3 Hz, 2H), 7.28 (d, J=8.3 Hz, 2H), 3.63 (t, J=6.6 Hz, 2H), 3.10-2.99 (m, 4H), 2.71-2.58 (m, 2H), 1.72-1.44 (m, 10H), 1.32 (m, 6H), 0.86 (t, J=7.4 Hz, 6H). To a solution of the crude alcohol (974 mg, 2.64 mmol) in DCM (7 mL) containing Tempo (8.40 mg, 52.7 μmol) was added a solution of saturated aqueous $NaHCO_3$ (7 mL) containing KBr (47.5 mg, 395 μmol) and TBAC (75.5 mg, 264 μmol). The resulting mixture was then cooled down to 0° C. and a solution of NaOCl (6 mL, 8.57 mmol), saturated $NaHCO_3$ (3 mL) and brine (3 mL) was added dropwise over 15 min. LC-MS show the corresponding carboxylic acid and still have some starting material alcohol left. Another portion of NaOCl (6 mL) mixed with saturated $NaHCO_3$ (3 mL) and brine (3 mL) was added over 5 min and the reaction was stirred for 15 min. No more alcohol was observed by LC-MS. The reaction was diluted with water (10 mL) and DCM (10 mL) and the phases were separated. The organic material (DCM) was extracted with water (2×10 mL). The combined aqueous phases were treated at room temperature with 10% HCl until pH around 4. The organic material was then extracted with EtOAc (3×10 mL) from the resulting acid aqueous phase. Dried over anhydrous sodium sulfate, filtered and concentrated under reduced pressure. The crude was purified by flash column chromatography (50 g silica, EtOAc in hexanes, 10 to 100%) affording compound BT056 (795 mg, 79%) as a white solid. LC-MS: RT=1.93 min; Purity: 97%; MS cal.: 383.55; Mass found: [M−H]: 382.5. $^1$H NMR (500 MHz, $CDCl_3$) δ 7.70 (d, J=8.4 Hz, 2H), 7.28 (d, J=8.4 Hz, 2H), 3.12-3.01 (m, 4H), 2.71-2.59 (m, 2H), 2.35 (t, J=7.5 Hz, 2H), 1.63 (s, 3H), 1.55 (dq, J=14.9, 7.4 Hz, 4H), 1.34 (m, 3H), 0.87 (t, J=7.4 Hz, 6H).

Scheme 14 - Synthesis of BT057

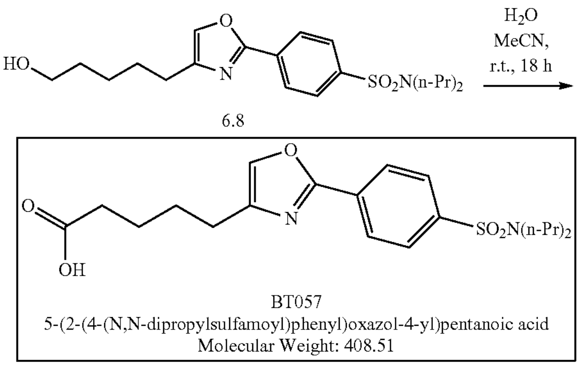

6.8

BT057

5-(2-(4-(N,N-dipropylsulfamoyl)phenyl)oxazol-4-yl)pentanoic acid

Molecular Weight: 408.51

5-(2-(4-(N,N-Dipropylsulfamoyl)phenyl)oxazol-4-yl) pentanoic acid (BT057). Tetrapropylammonium perruthenate (111 mg, 317 μmol) was added to a solution of 6.8 (1.25 g, 3.17 mmol), 4-methylmorpholine N-oxide (3.44 g, 28.5 mmol) and $H_2O$ (85.5 μL, 4.75 mmol) dissolved in MeCN (12.7 mL). The reaction was stirred for 18 h at room temperature. The reaction was quenched with isopropyl alcohol (15 mL) and concentrated under reduced pressure. The crude was purified by flash column chromatography (50 g silica, 0 to 30% MeOH/DCM) affording BT057 as a white solid. LC-MS: RT=1.73 min; Purity: 96.4%; MS cal.: 408.51; Mass found: [M+H]: 409.0. $^1$H NMR (500 MHz, $CDCl_3$) δ 8.13 (d, J=8.7 Hz, 2H), 7.88 (d, J=8.7 Hz, 2H), 7.50 (s, 1H), 3.15-3.07 (m, 4H), 2.64 (t, J=6.7 Hz, 2H), 2.43 (t, J=7.0 Hz, 2H), 1.80-1.71 (m, 4H), 1.60-1.47 (m, 4H), 0.87 (t, J=7.4 Hz, 6H).

The following compounds were prepared using the procedures given above or by adapting the above-procedures using appropriate starting materials. As shown in the Table, each compound made gave the expected molecular ion or will give the expected molecular ion.

| Compound designation | Molecular weight | m/z [M + H]$^+$ |
|---|---|---|
| BT032 | 403.53 | 404 |
| BT137 | 444.54 | 445 |
| BT136 | 410.55 | 411 |
| BT135 | 410.57 | 411 |
| BT163 | 389.51 | 390 |
| BT160 | 369.52 | 370 |
| BT004 | 368.21 | 370 |
| BT005 | 298.14 | 299.92 |
| BT006 | 312.15 | 313.96 |
| BT007 | 285.10 | 286.89 |
| BT008 | 301.10 | 302.92 |
| BT009 | 249.31 | 250.85 |
| BT010 | 283.09 | 284.90 |
| BT011 | 345.41 | 346.91 |
| BT026 | 397.58 | |
| BT027 | 452.61 | 454.13 |
| BT028 | 412.54 | 413.31 |
| BT029 | 398.52 | 399.24 |
| BT030 | 388.57 | |
| BT031 | 388.57 | 385.99* |
| BT032 | 403.53 | 404 |
| BT033 | 403.53 | 405.10 |
| BT034 | 467.58 | 468.39 |
| BT041 | 383.55 | 384.3 |
| BT043 | 411.61 | 412.6 |
| BT052 | 496.07 | 496.4 |
| BT053 | 510.09 | 510.3 |
| BT054 | 368.58 | 369.2 |
| BT055 | 393.53 | 394.3 |
| BT056 | 383.55 | 382.5* |
| BT057 | 408.51 | 409.0 |
| BT058 | 352.41 | 351.4* |

Example 2: Inhibition of Inflammasome Activation by Compounds of the Present Technology This example demonstrates the efficacy of the compounds of the present technology in inhibiting NLRP3 inflammasome activation in vitro, and that the compounds of the present technology exhibit a dose-responsive inhibition of inflammasome activation as assessed by IL-1β secretion.

In vitro stimulation of murine macrophages. Immortalized wild-type C57BL/6 bone-marrow derived macrophages (iBMDMs) were grown in DMEM supplemented with 10% heat inactivated FBS and 2 mM glutamine. iBMDMs were seeded in 96-well plates 24 hours prior incubation with lipopolysaccharide (LPS; 100 ng/mL) for 3 hours. Cells were then incubated with a control probenecid compound (probenecid dissolved in DMSO (Prob/D), probenecid dissolved in PBS (Prob/P)) or one of the probenecid analogs of the present technology (BT032, BT132, BT133, BT134, BT135, BT136, BT137, BT138, BT139, or BT140) at concentrations of 300 μM, 150 μM, 30 μM, or 3 μM 1 hour prior to stimulation with NLRP3 inflammasome activators, silica (250 μg/mL) or nigericin (6 μM). After an additional 6 hours, cell supernatants were collected and levels of IL-1β were quantified by ELISA. These experiments were run in triplicate three times.

Figure 2:
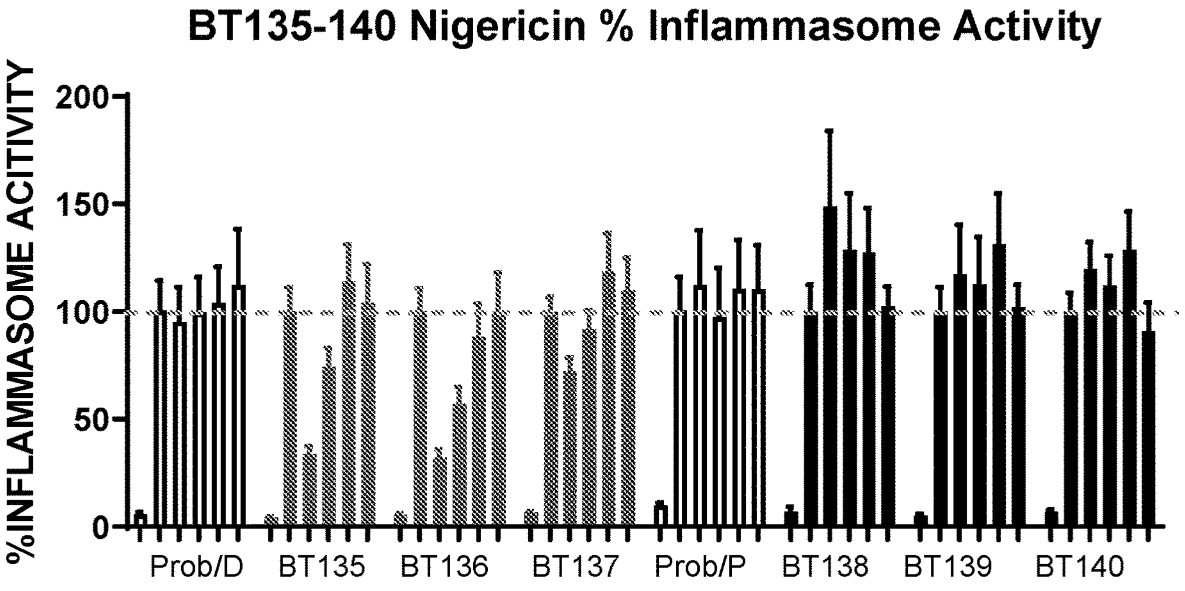
FIG. 2 is a chart showing the dose-response of probenecid analogs BT135, BT136, BT137, BT138, BT139, and BT140 on the inhibition of inflammasome activity as assessed by secreted IL-1β ELISA in macrophages pre-activated with lipopolysaccharide (LPS; 100 ng/mL). The macrophages were stimulated with the NLRP3 activator, nigericin (604). From left to right, the first bar for each compound (cluster) is non-silica activated, the second bar is activated but no compound, the following bars are the compound at 300 μM, 150 μM, 30 μM, and 3 μM. Prob/D=probenecid dissolved in DMSO; Prob/P=probenecid dissolved in PBS. The experiments were performed in triplicate three times.
Figure 3A:
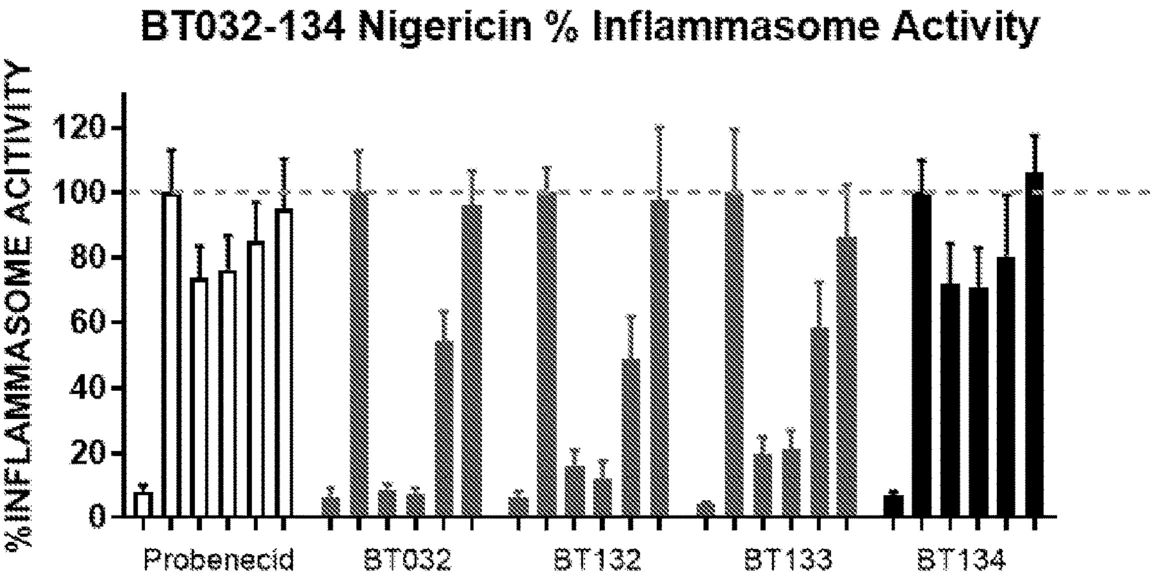
FIGS. 3A and 3B are charts showing the dose-response of probenecid analogs BT032, BT132, BT133, and BT134, on the inhibition of inflammasome activity as assessed by secreted IL-1β ELISA in macrophages pre-activated with lipopolysaccharide (LPS; 100 ng/mL). The macrophages were stimulated with either the NLRP3 activator, nigericin (604) (FIG. 3A) or silica (250 μg/mL) (FIG. 3B). From left to right, the first bar for each compound (cluster) is non-nigericin or non-silica activated, the second bar is activated but no compound, the following bars are the compound at 300 μM, 150 μM, 30 μM, and 3 μM. The experiments were performed in triplicate.
Figure 3B:
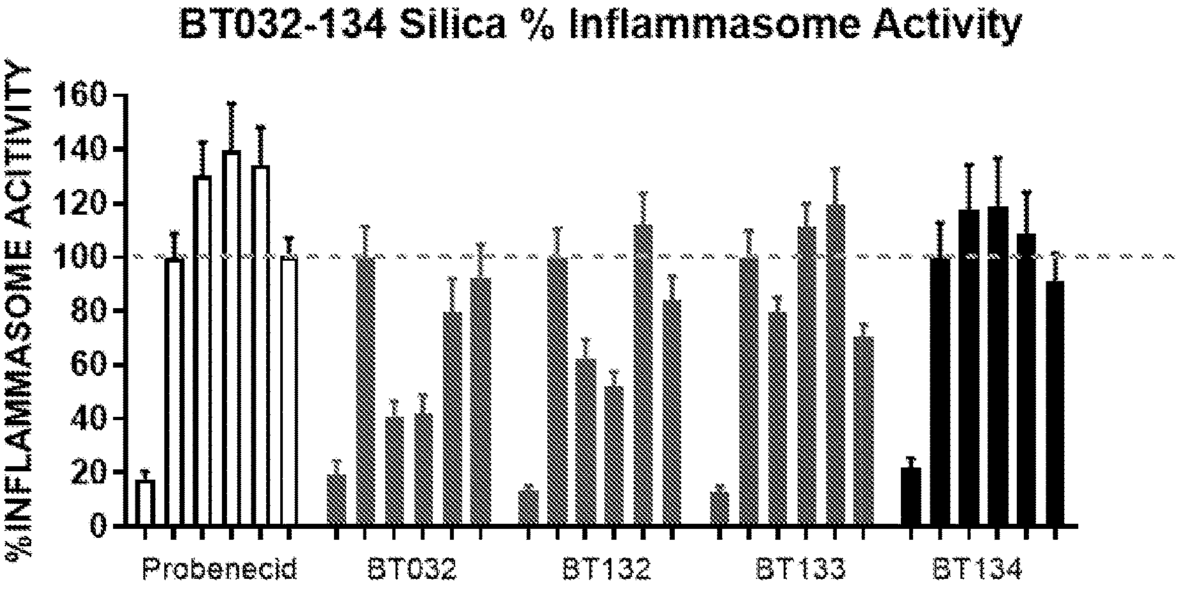

Results. As shown by FIG. 2 and FIGS. 3A and 3B, treatment with the probenecid analogs of the present technology reduced IL-1β secretion in a dose-dependent manner in response to different NLRP3 stimuli (i.e., silica and nigericin). Overall, probenecid analogs BT032, BT132, BT133, and BT136 are more potent than the control probenecid compounds.

Accordingly, these results demonstrate that probenecid analogs of the present technology are useful in methods for inhibiting NLRP3 inflammasome activation and for treating or preventing inflammasome-mediated lung disease or conditions.

Example 3: Probenecid Analogs of the Present Technology for the Prevention and Treatment of Inflammasome-Mediated Lung Disease—Pandemic Influenza Model This example demonstrates the capability of the probenecid analogs of the present technology to reduce inflammasome-mediated disease or conditions and hyperinflammation in vivo during high dose influenza A challenge in mice.

Influenza virus infection in mice. Six- to eight-week old C57BL/6 male and female mice are maintained in a pathogen-free facility. The influenza A virus strain used in this study was HKx31 (H3N2) pandemic strain. Additional strains, such as A/PR/8/34 (H1N1), may also be studied. Viruses were grown in 10-day embryonated chicken eggs by standard procedures and titrated on Madin-Darby Canine Kidney (MDCK) cells.

For virus infection studies, groups of five to fourteen male and female C57BL/6 mice were randomized into treatment groups (BT032, BT133, BT135, or PBS). Mice were lightly anesthetized and infected intranasally with $10^5$ plaque-forming units (pfu) of HKx31 (H3N2) in 50-4, PBS. Following infection on day 0, mice were treated one day post-infection (day 1) and every 48 hours thereafter (e.g., on days 1, 3, 5 post-infection) or three days post-infection (day 3) and every 48 hours thereafter (e.g., on days 3, 5, 7 post-infection) with 40 mg/kg probenecid analog of the present technology (BT032, BT133, BT135) via the intranasal route in 50 μL PBS. Control mice were treated with PBS alone. Mice were weighed daily and assessed for visual signs of clinical disease, including inactivity, ruffled fur, labored breathing, and huddling behavior. Animals that lost ≥20% of their original body weight or displayed severe clinical signs of disease were euthanized.

For analysis of the impact of the probenecid analogs of the present technology on cellular infiltrates in the lungs, groups of C57BL/6 mice were intranasally infected with a high dose of HKx31 ($10^5$ pfu; n=8 for PBS, IAV alone and IAV with BT032 treatment; n=4 for BT032 alone (no infection)) on day 0, and were treated once with 40 mg/kg probenecid analog of the present technology (BT032) or PBS on day 3 post-infection, and 24 hours later, the mice were euthanized. Bronchoalveolar lavage (BAL) fluid was immediately obtained following euthanasia by flushing the lungs three times with 1 mL PBS.

Recovery and characterization of leukocytes from mice. For flow cytometric analysis, BAL cells were treated with red blood cell lysis buffer (Sigma Aldrich), and cell numbers and viability were assessed via trypan blue exclusion using a hemocytometer. BAL cells were incubated with Fc block, followed by staining with fluorochrome-conjugated monoclonal antibodies to Ly6C, Ly6G, CD11c, and I-$A^b$ (BD Biosciences, USA). Neutrophils (Ly6$G^+$), airway macrophages (CD11$c^+$ I-$A^{b\ high}$), inflammatory macrophages (Ly6$G^-$ Ly6$C^+$) were quantified by flow cytometry, as described in Tate et al., *Scientific Reports* 6, 27912 (2016). Live cells (propidium iodide negative) were analyzed using a flow cytometer. Total cell counts were calculated from viable cell counts performed via trypan blue exclusion.

Macrophage infiltrates and proinflammatory chemokine concentrations from mice. C57BL/6 mice (n=8 per group) were intranasally infected with $10^5$ PFU HKx31 IAV. On day 3 post-infection, mice were treated or not with 20 mg/kg of BT032 and euthanized after 24 h treatment. Bronchoalveolar lavage (BAL) fluid (BALF) was obtained from mice and assayed for macrophage numbers ($CD11c^+$, $I\text{-}Ab^{low}$) and MCP-1 concentration determined by cytokine bead analysis as determined by flow cytometry.

Figure 4A:
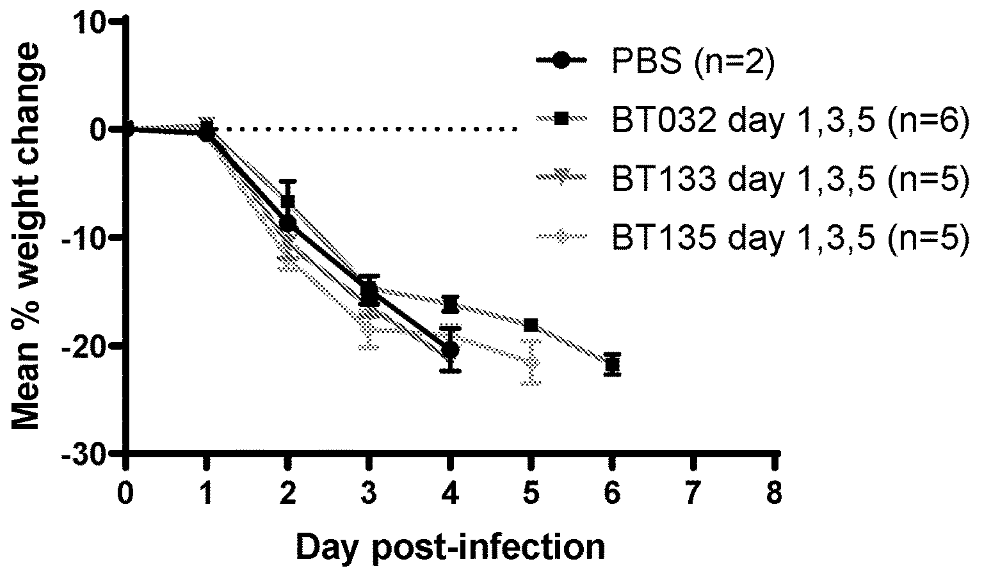
FIGS. 4A-4E are charts showing the mean percent daily weight change (FIGS. 4A and 4D) and survival curves (FIGS. 4B, 4C, and 4E) for groups of C57BL/6 mice infected intranasally (n=5-14 per group) with a high dose of HKx31 ($10^5$ pfu). Mice were treated intranasally with 40 mg/kg of a probenecid analog of the present technology (BT032, BT133, or BT135) or PBS on either day 1 or day 3 post-infection and every 48 hours thereafter.
Figure 4B:
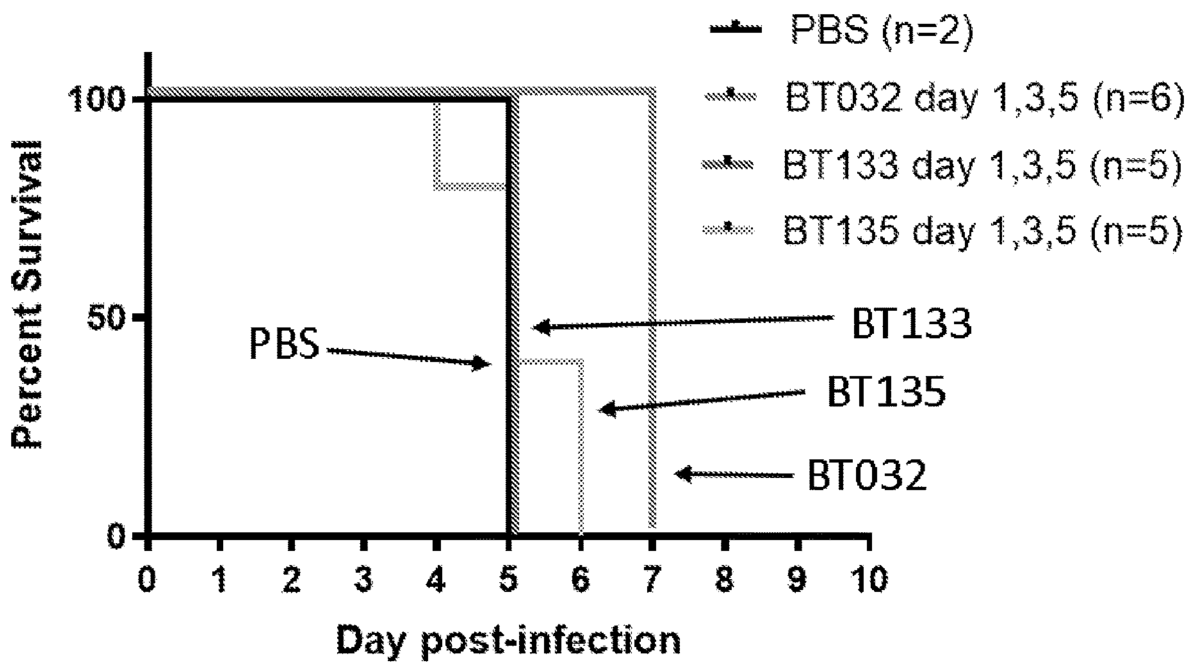
Figure 4C:
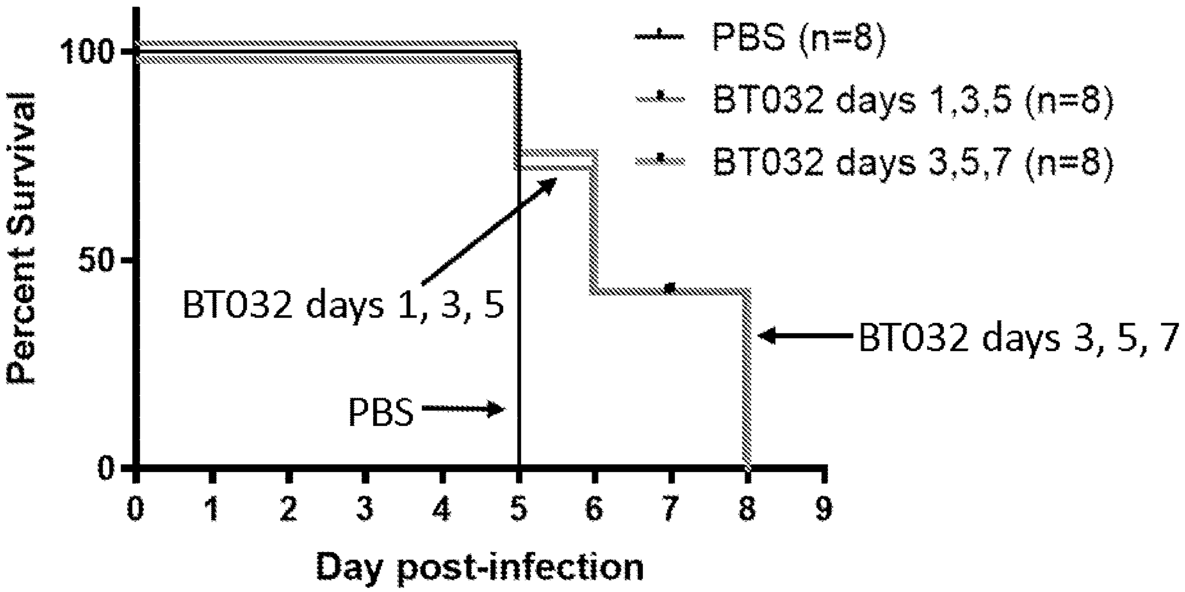
Figure 4D:
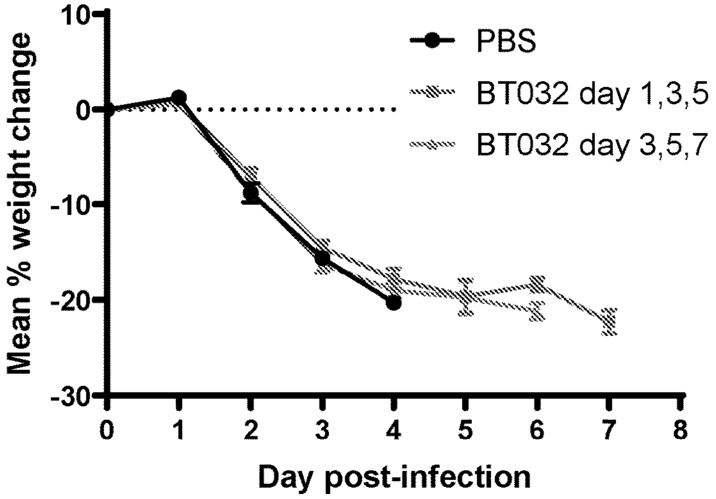
Figure 4E:
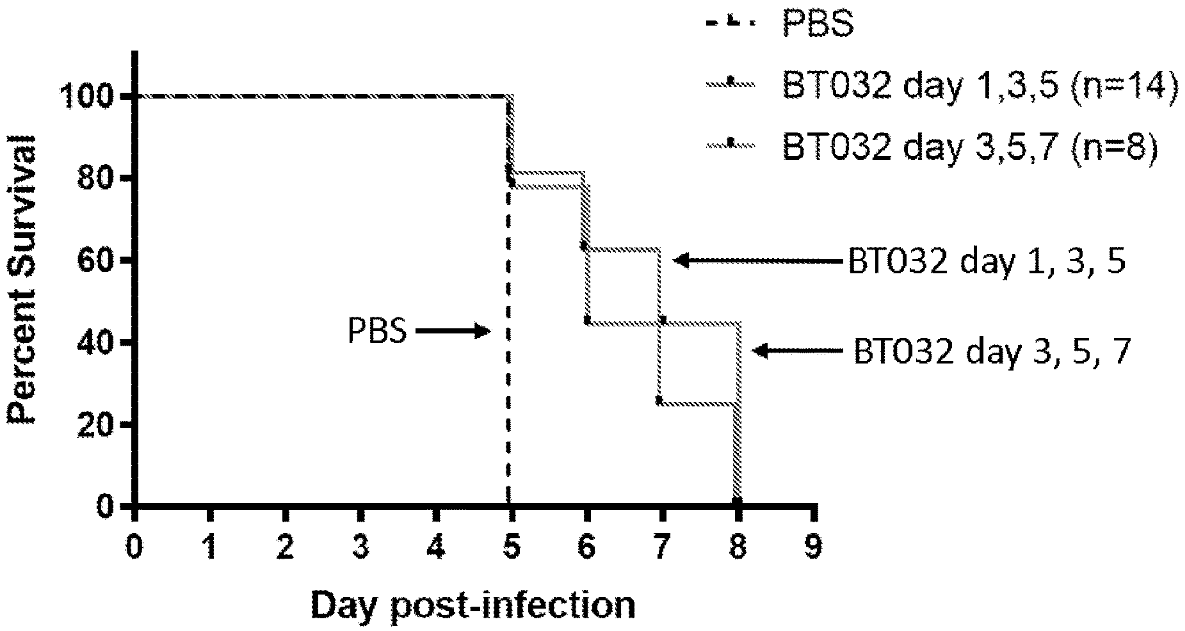

Results. Intranasal treatment of mice with the probenecid analogs of the present technology reduced clinical signs of disease including weight loss (FIGS. 4A and 4D) and prolonged the survival of mice post-infection (FIGS. 4B, 4C, and 4E). In particular, BT032 prolonged the survival of mice from 5 days up to 7-9 days post-infection (FIGS. 4B, 4C, and 4E).

These results demonstrate that early treatment (on day 1 post-infection with HKx31, and every 48 hours thereafter) of the mice with the probenecid analogs of the present technology is effective in methods for treating or preventing inflammasome-mediated lung disease or conditions and does not result in adverse effects (FIGS. 4A-4E).

These results also demonstrate that commencing treatment of the mice with the probenecid analogs of the present technology on day 3 post-infection (which has been determined to be the peak of disease following HKx31 (H3N2) challenge; Tate et al. (2016)) and every 48 hours thereafter (e.g., days 5, 7), results in reduced clinical signs of the disease including weight loss and prolonged survival (FIGS. 4C-4E). Accordingly, these results demonstrate that the probenecid analogs of the present technology are effective in methods for treating inflammasome-mediated lung disease or conditions, for example, in the late stages of severe and highly virulent influenza A infection.

Figure 5A:
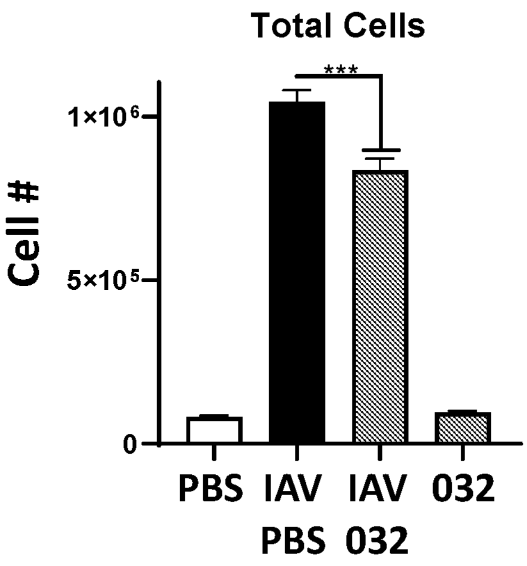
FIGS. 5A-5E are charts showing the administration of probenecid analogs of the present technology (e.g., BT032) reduce hyperinflammation in the airways during HKx31 infection. Groups of C57BL/6 mice were infected intranasally with a high dose of HKx31 ($10^5$ pfu; n=8 for PBS, IAV alone and IAV with BT032 treatment; n=4 for BT032 alone (no infection)). Mice were treated intranasally with 20 mg/kg of a probenecid analog of the present technology (BT032) or PBS on day 3 post-infection. Total numbers of leukocytes in BAL were determined by viable cell counts (FIG. 5A), and total $CD11c^+$ I-$A^{b\ low}$ macrophages (FIG. 5B), $Ly6G^+$ neutrophils (FIG. 5C), $Ly6C^+$ inflammatory macrophages (FIG. 5D), and $CD11c^+$ I-$A^{b\ low}$ dendritic cells (FIG. 5E) were determined by flow cytometry.
Figure 5B:
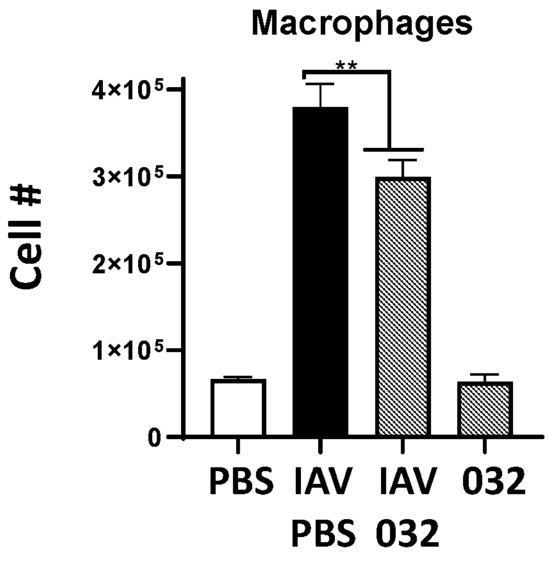
Figure 5C:
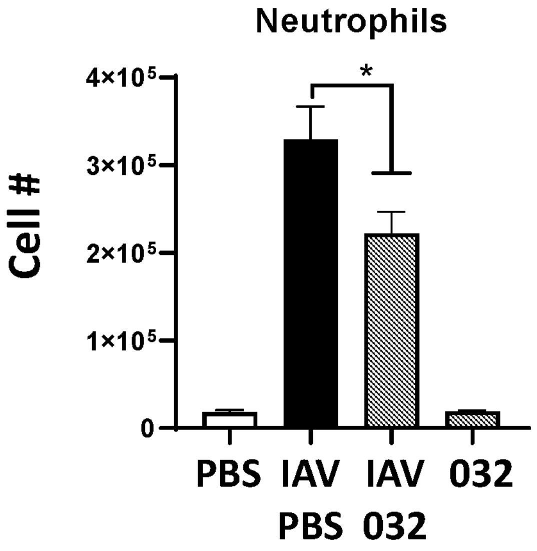
Figure 5D:
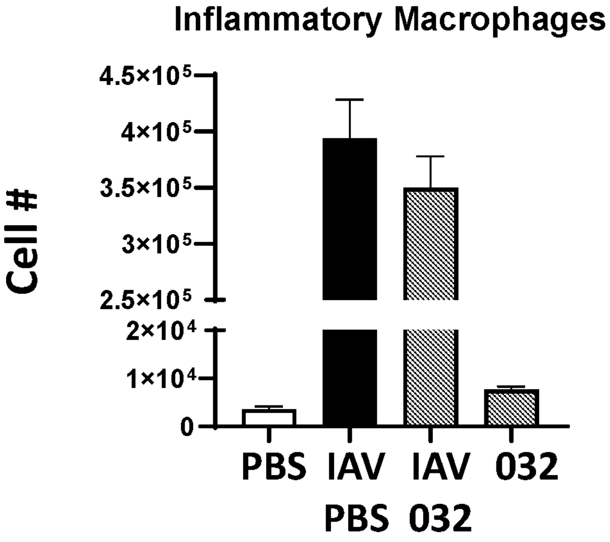
Figure 5E:
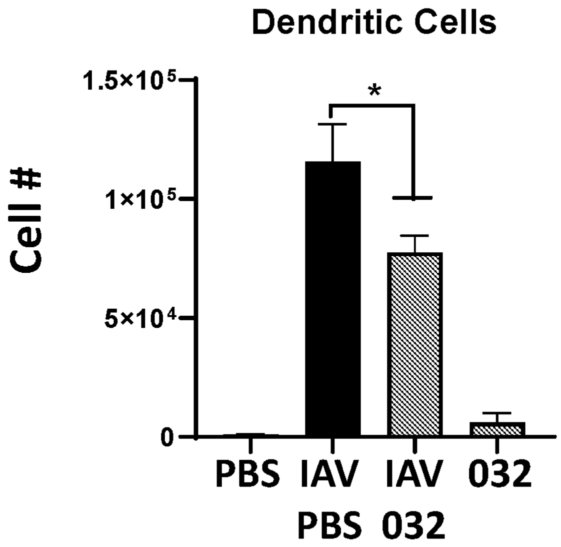
Figure 5F:
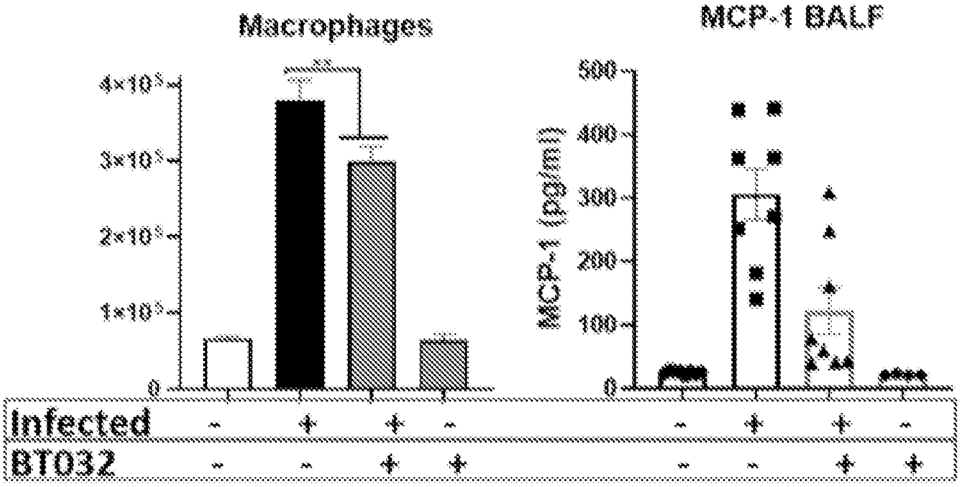
FIG. 5F is a chart showing macrophage infiltrates and proinflammatory chemokine concentrations in the airways of mice treated or not as indicated (n=8 mice per group) with $10^5$ PFU HKx31 IAV. On day 3 post-infection, mice were treated with 20 mg/kg of BT032 and euthanized after 24 h treatment. Bronchoalveolar lavage (BAL) fluid (BALF) was obtained from mice and assayed for macrophage numbers ($CD11c^+$, I-$Ab^{low}$) and MCP-1 concentration determined by cytokine bead analysis as determined by flow cytometry. The BALF concentration of chemokine MCP-1 was determined by cytokine bead array.

As shown in FIGS. 5A-5F, probenecid analog treatment groups exhibited reduced biomarkers of excessive pulmonary inflammation and cellular infiltrates, including reduced total numbers of cellular infiltrates in the airways (FIG. 5A), such as alveolar macrophages (FIG. 5B), neutrophils (FIG. 5C), inflammatory $Ly6C^+$ macrophages (FIG. 5D), dendritic cells (FIG. 5E), and chemokine, MCP-1 (FIG. 5F).

Accordingly, these results demonstrate that the probenecid analogs of the present technology are effective in methods for preventing and treating inflammasome-mediated lung disease or conditions.

Example 4: Probenecid Analogs of the Present Technology for the Prevention and Treatment of Inflammasome-Mediated Lung Disease This example will demonstrate the capability of the probenecid analogs of the present technology to reduce inflammasome-mediated disease or conditions and hyperinflammation in vivo during high dose influenza A challenge in subjects.

Animal Models

Animal models suitable for use in this example include, but are not limited to, animal influenza models, such as that described herein. One of skill in the art will understand that the following description is illustrative and may be applied as appropriate to other animal models.

Influenza virus infection in mice. Six- to eight-week old C57BL/6 male and female mice will be maintained in a pathogen-free facility. Influenza A virus strains to be used in this study include A/PR/8/34 (H1N1) and HKx31 (H3N2). Viruses are grown in 10-day embryonated chicken eggs by standard procedures and titrated on Madin-Darby Canine Kidney (MDCK) cells.

For virus infection studies, groups of eight male and female C57BL/6 mice are randomized into treatment groups. Mice are lightly anesthetized and infected intranasally with $10^5$ plaque-forming units (pfu) of HKx31 (H3N2) or 50 pfu PR8 (H1N1) in 50-4, PBS. Following infection, mice are treated on day 3 post-infection and every 48 hours thereafter (e.g., on days 5, 7, 9, 11 etc., post-infection) with 40 mg/kg probenecid analog of the present technology via the intranasal route in 50 μL PBS. Control mice are treated with PBS alone or 40 mg/kg probenecid control compound. Uninfected mice treated with the probenecid analogs of the present technology are included for comparison. Mice are weighed daily and assessed for visual signs of clinical disease, including inactivity, ruffled fur, labored breathing, and huddling behavior. Animals that lose ≥20% of their original body weight or display severe clinical signs of disease will be euthanized.

Bronchoalveolar lavage (BAL) fluid is immediately obtained following euthanasia by flushing the lungs three times with 1 mL PBS. The lungs are then removed and immediately frozen in liquid nitrogen. Titers of infectious virus in lung homogenates are determined by standard plaque assay on MDCK cells.

Quantification of pro-inflammatory cytokines in BAL fluid. To detect cytokines, BAL fluid is collected and stored at −80° C. IL-1β is quantified by ELISA. Levels of IL-6, CCL2, IFN-γ, IL-10, IL12p70, and TNF-α proteins are determined by cytokine bead array and mouse inflammation kit (Becton Dickinson).

Recovery and characterization of leukocytes from mice. For flow cytometric analysis, BAL cells are treated with red blood cell lysis buffer (Sigma Aldrich), and cell numbers and viability are assessed via trypan blue exclusion using a hemocytometer. BAL cells are incubated with Fc block, followed by staining with fluorochrome-conjugated monoclonal antibodies to Ly6C, Ly6G, CD11c, and $I\text{-}A^b$ (BD Biosciences, USA). Neutrophils ($Ly6G^+$), airway macrophages ($CD11c^+$ $I\text{-}A^{b\ high}$), inflammatory macrophages ($Ly6G^-$ $Ly6C^+$) are quantified by flow cytometry, as described in Tate et al., *Scientific Reports* 6, 27912 (2016). Live cells (propidium iodide negative) are analyzed using a flow cytometer. Total cell counts are calculated from viable cell counts performed via trypan blue exclusion.

Results. It is expected that intranasal treatment of mice with the probenecid analogs of the present technology will reduce clinical signs of disease including weight loss and prolong the survival of mice post-infection. It also anticipated that these results will show that treatment of uninfected mice with the probenecid analogs of the present technology will not result in weight loss or any clinical signs of the disease.

It is expected that commencing treatment of the mice with the probenecid analogs of the present technology on day 3 post-infection (which has been determined to be the peak of disease following H3N2 challenge; Tate et al. (2016)) and every 48 hours thereafter (e.g., days 7, 9, and 11), will result in reduced clinical signs of the disease including weight loss and prolonged survival. Similarly, it is expected that commencing treatment of the mice with the probenecid analogs of the present technology on day 7 (the onset of severe disease following PR8 H1N1 challenge; Tate et al. (2016)) and every 48 hours thereafter, will result in reduced weight loss and improved survival and recovery. In addition, it is expected that the treatment groups will exhibit reduced biomarkers of excessive pulmonary inflammation and cellular infiltrates, including reduced total numbers of cellular infiltrates in the airways, such as alveolar macrophages, neutrophils, inflammatory $Ly6C^+$ macrophages, and dendritic cells (DCs), and that levels of IL-1β production and hyperinflammation in the airways will be reduced. Accordingly, these results will show that the probenecid analogs of the present technology are effective in methods for treating inflammasome-mediated lung disease or conditions, for example, in the late stages of severe and highly virulent influenza A infection.

It is also expected that commencing early treatment of the mice with the probenecid analogs of the present technology will be effective in methods for treating or preventing inflammasome-mediated lung disease or conditions and will not result in adverse effects. It is anticipated that treatment with the probenecid analogs of the present technology on day 1 (HKx31) or day 5 (PR8) post-infection, and every 48 hours thereafter, will result in reduced clinical signs of the disease including weight loss and prolonged survival. Collectively, these results will show that the probenecid analogs of the present technology are effective in methods for treating or preventing inflammasome-mediated lung disease or conditions, at any stage of clinical presentation without adverse effects or enhancement of disease.

Human Subjects

Human subjects diagnosed as having or suspected to have an inflammasome-mediated lung disease or conditions or a related disorder and presently displaying one or more symptoms and/or pathologies of inflammasome-mediated lung disease or conditions or a related disorder, are recruited using selection criteria known and accepted in the art.

Methods of Prevention and Treatment: Subjects are administered probenecid analogs of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered probenecid analogs of the present technology prior to or subsequent to the development of symptoms and/or pathologies of inflammasome-mediated lung disease or conditions or related disorders and assessed for reversal of symptoms/pathologies or attenuation of expected symptoms/pathologies using methods known in the art.

Results: It is expected that the probenecid analogs of the present technology will induce reversal of symptoms and/or pathologies of inflammasome-mediated lung disease or conditions and related disorders in human subjects. These results will show that compounds of the present technology are useful and effective for the prevention and treatment of such disorders.

Example 5: Inhibition of NLRP1 and NLRP3 Inflammasomes by Probenecid Analogs of the Present Technology This example demonstrates the efficacy of the compounds of the present technology in inhibiting NLRP1 and NLRP3 inflammasome activation in vitro, and that the compounds of the present technology exhibit a dose-responsive inhibition of inflammasome activation as assessed by IL-1β secretion.

IC50 curves. Immortalized BMDMs grown in DMEM/10% FCS, 2 mM glutamine at 5% CO2 were seeded at $4\times10^4$ cells in 96 well format, 20 h prior to priming with 100 ng/ml LPS *E. coli* 055:B5 for a further 3 h. Macrophages were treated with drug (3.9-350 μM) or vehicle (DMSO) in serum-free media for 60 mins prior to challenge with nigericin (3 μM) for 120 mins. Cultured supernatants were assayed for secreted IL-1β by ELISA according to manufacturer's instruction.

In vitro stimulation of human macrophages. Immortalized BMDMs grown in DMEM/10% FCS, 2 mM glutamine at 5% CO2 were seeded at $4\times10^4$ cells in 96 well format, 20 h prior to priming with 100 ng/ml LPS *E. coli* 055:B5 (except for LPS (B4) priming done with $Pam_3Cys$; 100 ng/ml) for a further 3 h. Macrophages were treated with vehicle (DMSO), BT032 (20, 100 μM), or MCC950 (5 μM) where indicated in serum-free media for 60 mins prior to challenge with NLR agonists; nigericin (3 μM; 120 mins), monosodium urate crystals; MSU (250 μg/ml; 6 h), silica MSU (250 μg/ml; 6 h), L18-MDP (100 μg/ml; 16 h), LPS Serotype 0111:B4 (2 μg; 16 h), poly dA:dT (1 μg; 6 h) and Flagellin (200 μg; 6 h) all complexed with Lipofectamine 2000. Cultured supernatants were assayed for secreted IL-1β by ELISA according to manufacturer's instructions.

Figure 6A:
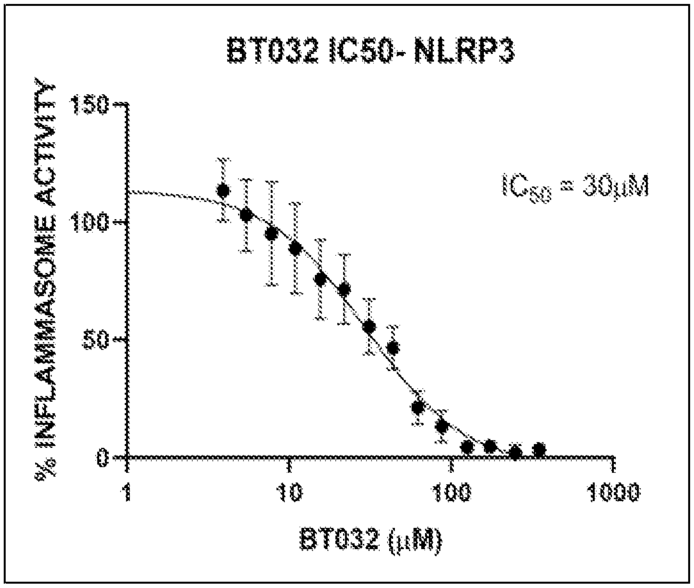
FIGS. 6A and 6B are charts showing inflammasome activity as determined by measuring secreted IL-1β concentrations in murine immortalized BMDMs pre-activated with lipopolysaccharide (LPS; 100 ng/mL) for 3 h. The macrophages were stimulated with either the NLRP3 activator, nigericin (3 μM) (FIG. 6A) or the NLRP1 agonist L18-MDP (100 μg/mL) (FIG. 6B) and treated or not with BT032 (3.9-350 μM). Secreted IL-1β concentrations were measured by ELISA and are represented as the mean±SEM of the pooled results of 3 independent experiments conducted in triplicate where activity was normalized as percentage of activity as related to the DMSO-treated control cells and non-stimulated (FIG. 6A) or as IL-1β concentration (FIG. 6B) and shown as the curve of the Log [M] BT032 versus normalized responses (variable slope).
Figure 6B:
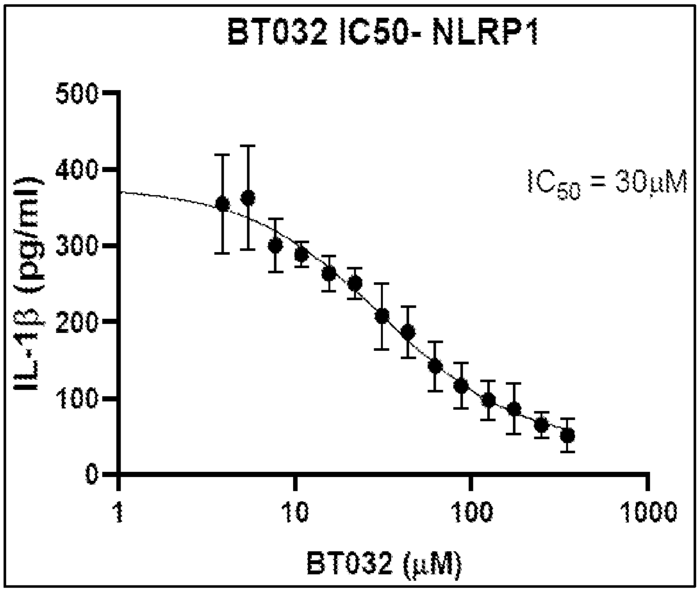
Figure 6C:
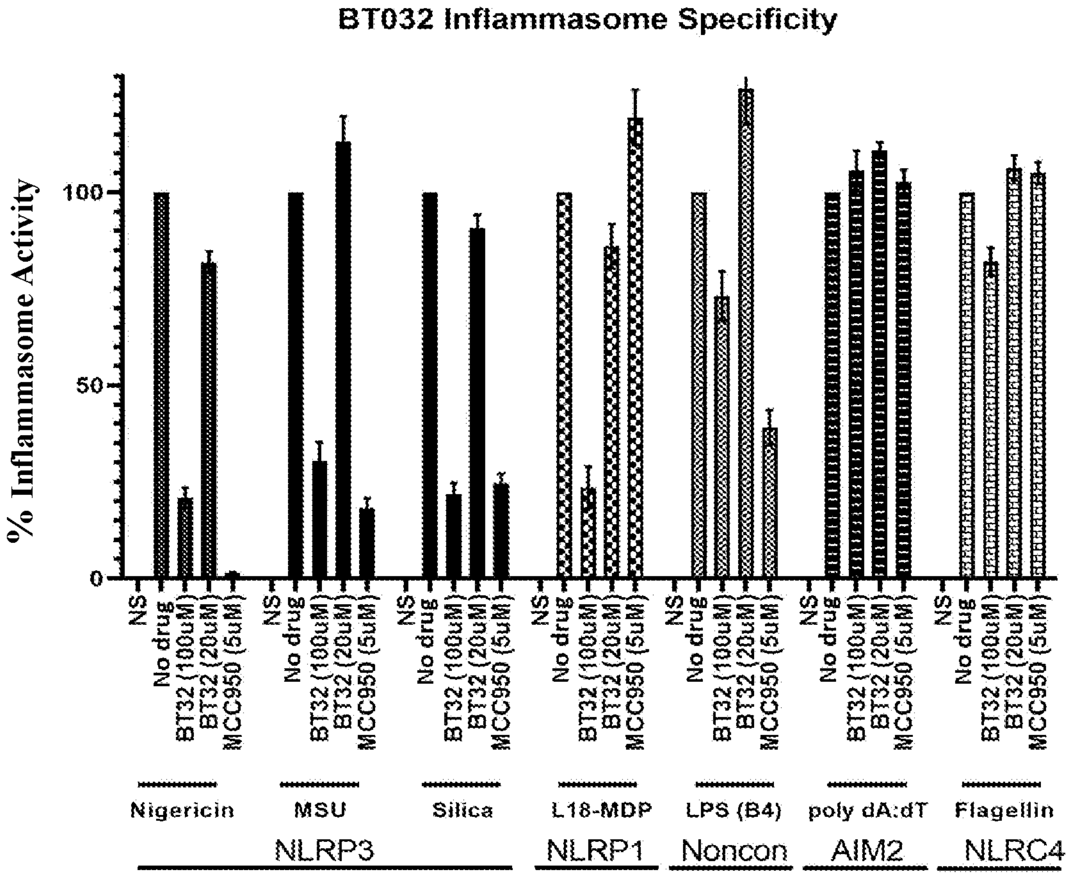
FIG. 6C is a chart showing the effects of treatment of macrophages with BT032 on NLRP3 (from left to right: Nigericin, Monosodium Urate (MSU), and Silica)- and NLRP1 (L18-MDP)-induced inflammasome activation, on non-canonical inflammasome activity (LPS (B4)), and on AIM2 (poly dA:dT) and NLRC4 (Flagellin)-mediated inflammasome activation. MCC950 is an NLRP3-specific inhibitor; MSU=monosodium urate; LPS=lipopolysaccharide; BT32=BT032. Secreted IL-1β concentrations were measured by ELISA and are represented as the mean±SEM of the pooled results of 3 independent experiments conducted in triplicate where activity was normalized as percentage of activity as related to the DMSO-treated control cells ("no-drug") and non-stimulated ("NS") cells.

Results. As shown by FIGS. 6A and 6B, the half maximal inhibitory concentration (IC50) for BT032 inhibition of NLRP3- and NLRP1-mediated inflammasome activity, respectively, is 30 μM. As shown by FIG. 6C, treatment of macrophages with BT032 specifically dose-dependently inhibited NLRP3 (Nigericin, Monosodium Urate; MSU, and Silica)- and NLRP1 (L18-MDP)-induced inflammasome activation. BT032, however, had limited impact upon non-canonical inflammasome activity (LPS (B4)) and no effect upon both AIM2 (poly dA:dT) and NLRC4 (Flagellin)-mediated inflammasome activation. Importantly, while the specific NLRP3 inhibitor MCC950 inhibited nigericin, MSU, and silica inflammasome activation, unlike BT032, it had no impact upon NLRP1 activity. These findings demonstrate that probenecid analogs of the present technology (e.g., BT032) are specific NLRP1 and NLRP3 inhibitors.

Accordingly, these results demonstrate that probenecid analogs of the present technology, such as BT032, are useful in methods for inhibiting NLRP3 and NLRP1 inflammasome activation and for treating or preventing inflammasome-mediated diseases or conditions.

Example 6: Inhibition of NLRP1 Activation in Human Bronchial Epithelial Cells by Probenecid Analogs of the Present Technology Epithelial cell NLRP1 is activated by double-stranded (ds) RNA (e.g., rhinovirus, coronavirus, Flaviviruses, Dengue virus, Zika virus, West Nile virus infection, etc.). This example demonstrates the efficacy of the compounds of the present technology in inhibiting NLRP1 inflammasome activation in primary bronchial epithelial cells isolated from human subjects.

Methods. Primary bronchial epithelial cells (PBEC) were obtained from bronchial brushings and cultured under submerged conditions on collagen-coated flasks in supplemented bronchial epithelial growth medium. PBECs were seeded at $2.5\times10^5$/ml cells in collagen-coated 96 well plates overnight. PBECs were treated with BT032 (20, 100, 350 μM), MCC950 (MCC; 5 μM) or vehicle (DMSO) in serum-free media for 60 mins prior to challenge with high-molecular weight poly (I:C) complexed with Lipofectamine 2000 for 10 h. Cultured supernatants were assayed for secreted IL-1β by ELISA according to manufacturer's instruction.

Figure 7:
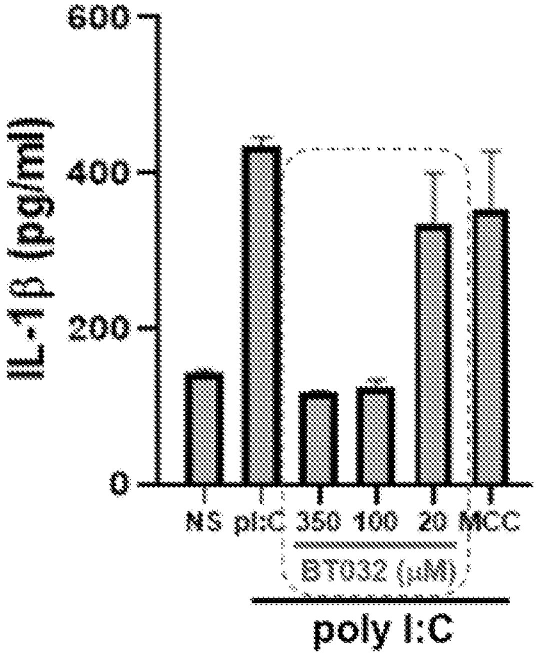
FIG. 7 is a chart showing the effect of BT032 (20, 100 and 350 μM) inhibition on the challenge of primary derived human bronchial epithelial cells ($5\times10^4$) obtained from consenting volunteers and treated with the NLRP1 viral mimic dsRNA poly I:C (1.0 μg/ml) transfected into cells with Lipofectamine. The NLRP3 selective inhibitor MCC950 (MCC: 5 μM) was used as a negative control. Secreted IL-1β concentrations were assayed by ELISA from cultured supernatants and results are shown as the mean±SEM of two independent experiments conducted in triplicate.
Figure 8A:
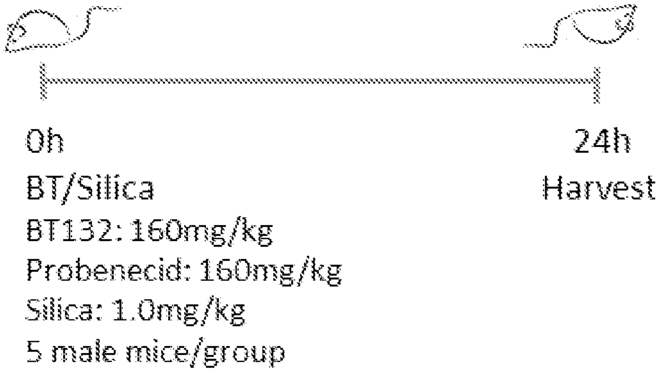
FIG. 8A is a schematic of the mouse lung silicosis model experiment.
Figure 8B:
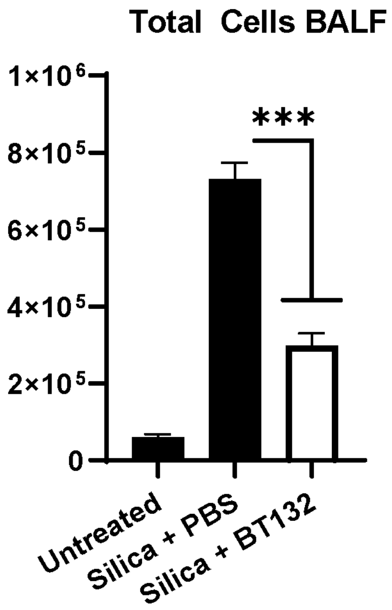
FIGS. 8B-8E are charts showing the administration of probenecid analogs of the present technology (e.g., BT132) reduce hyperinflammation in the airways following challenge with silica. C57BL/6 mice (n=5 per group) were intranasally treated with PBS (50 μl), silica (1 mg in 50 μl PBS) or silica (1 mg) in conjunction with BT132 (40 mg/kg) in a total volume of 50 μl for 24 h. Airway leukocytes in bronchoalveolar lavage (BAL) fluid (BALF) were determined by viable cell counts (FIG. 8B), $Ly6G^+$ neutrophils (FIG. 8C), and total $CD11c^+$ Ab low macrophages (FIG. 8D). IL-1β concentrations in the BALF were determined by ELISA (FIG. 8E). Data presented as the mean±SEM from 5 mice per group, significant difference from silica-alone challenged mice, *$p<0.05$, ***$p<0.001$, one-way ANOVA.
Figure 8C:
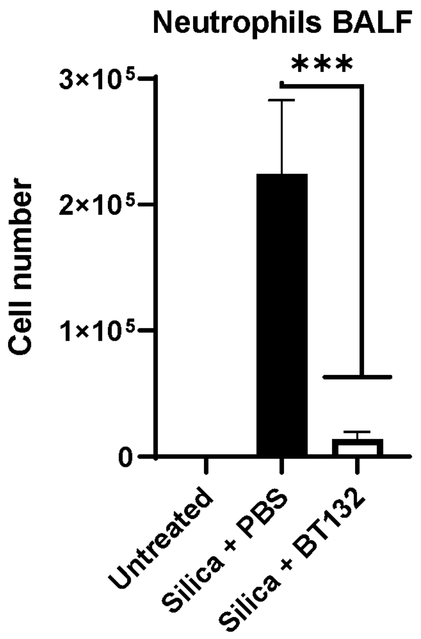
Figure 8D:
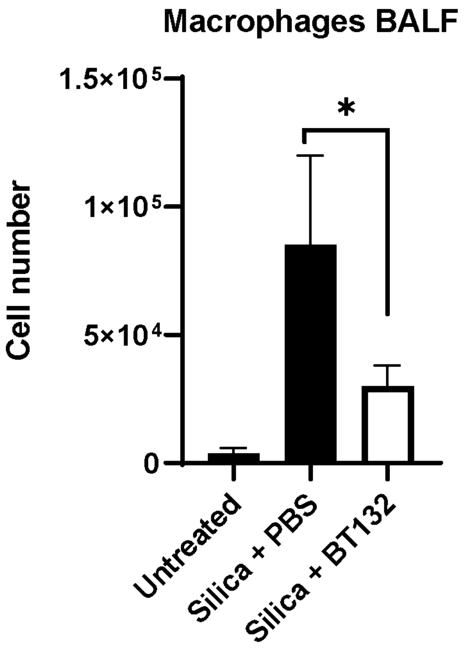
Figure 8E:
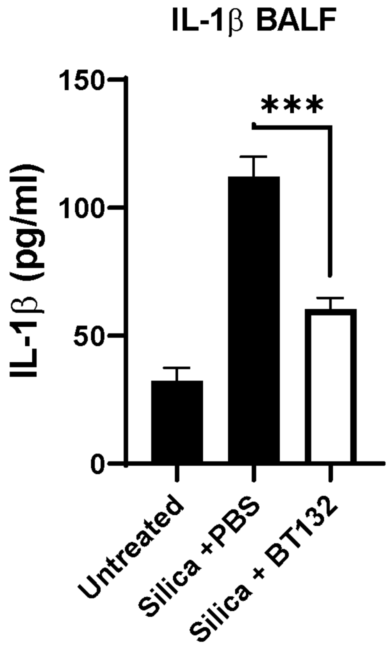

Results. As shown by FIG. 7, treatment with the probenecid analog, BT032, inhibited poly I:C NLRP1 activation in primary human bronchial epithelial cells as demonstrated by the dose-dependent reduction in IL-1β secretion.

Accordingly, these results demonstrate that probenecid analogs of the present technology, such as BT032, are useful in methods for inhibiting inflammasome activation in human bronchial epithelial cells and for treating or preventing inflammasome-mediated lung disease or conditions. These results further demonstrate that probenecid analogs of the present technology, such as BT032, are useful in methods of treating viral infections associated with NLRP1 activation by dsRNA such as respiratory viral infections caused by, but not limited to, rhinovirus, coronavirus, Flaviviruses, Dengue virus, Zika virus, and West Nile virus.

Collectively, Example 5 and Example 6 demonstrate that BT032 is capable of dual inhibition of the NLRP3 and NLRP1 inflammasomes. Accordingly, these results demonstrate that the probenecid analogs of the present technology (e.g., BT032) dampen inflammation mediated by both macrophages and epithelial cells and are useful in methods of preventing or treating inflammasome-mediated lung disease or conditions, such as acute exacerbations of COPD (AECOPD).

Example 7: BT132 is Efficacious in a Mouse Lung Silicosis Model

This example demonstrates the efficacy of the compounds of the present technology in reducing inflammation associated with the inhalation of silica in a mouse lung silicosis model.

Methods. Groups of 5 C57Bl/6 mice (6-8 weeks old) were anaesthetized and intranasally treated with 50 μl of either PBS, 1 mg silica in PBS, or 1 mg silica/BT132 (40 mg/kg). Mice were euthanized 24 h following challenge and BAL obtained from euthanized mice by flushing the lungs three times with 1 ml of PBS. For flow cytometric analysis, BAL cells were treated with red blood cell lysis buffer, and cell numbers and viability were assessed via Trypan blue exclusion using a haemocytometer. BAL cells were incubated with Fc block (2.4G2), followed by staining with fluorochrome-conjugated monoclonal antibodies to Ly6C, Ly6G, CD11c, and I-Ab (MHC-II). Neutrophils ($Ly6G^+$) and, airway macrophages ($CD11c^+$ I-Ab low) were quantified by flow cytometry. Live cells (propidium iodide negative) were analyzed using a flow cytometer and FlowJo software. Total cell counts were calculated from viable cell counts performed via Trypan blue exclusion. BAL IL-1β concentrations were assayed by ELISA according to manufacturer's instruction.

Results. As shown by FIGS. 8B-8E, while silica induced a robust inflammatory response as evidenced by increased cells in the BAL fluid (BALF) of mice, constituting increased neutrophils and macrophages, mice simultaneously treated with BT132 display significantly decreased pulmonary leukocyte influx and IL-1β concentrations, indicative of reduced pulmonary inflammatory burden.

Accordingly, these results demonstrate that probenecid analogs of the present technology, such as BT132, are useful in methods for reducing cellular infiltrate (immune cell infiltration) levels and cytokine levels in the lung and for treating or preventing inflammasome-mediated lung disease or conditions, including inflammasome-mediated lung disease or conditions associated with inhalation of an irritant.

Example 8: BT032 Inhibits Nigericin-Induced ASC Speck Formation

This example demonstrates the efficacy of the compounds of the present technology in inhibiting the formation of ASC (apoptosis-associated speck-like protein containing a caspase activating and recruitment domain) specks.

Methods. NLRP3-deficient immortalized macrophages stably expressing ASC-cerulean and NLRP3 were seeded in 8-well Ibidi chamber slides ($2\times10^5$/ml) 24 h prior to stimulation. Macrophages were treated with BT032 (350 μM) or vehicle (DMSO) in serum-free media for 60 mins prior to challenge with nigericin (3 μM; 90 mins). 10 mins prior to harvesting, cells were treated with Hoechst 33342, washed and fixed in 4% paraformaldehyde and stored in PBS. Six random fields were imaged at 60× magnification with 40 z planes. Images are deconvoluted z stacks by overlapping scanning processed using ImageJ. ASC-cerulean specks were counted for each field and as percentage of specks per field and represented as a percentage of total Hoechst positive cells.

Figure 9E:
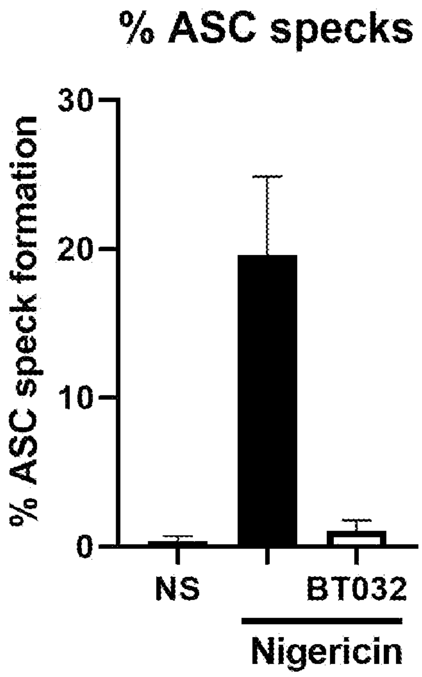
FIG. 9E is a chart showing the number of ASC specks detected per field (6-7 fields per sample) compared to the total number of cells/field as determined by staining nuclei. Data is represented as a percentage of ASC-specks per field of view for each treatment group as outlined in FIGS. 9B-9D.

Results. As shown by FIGS. 9B-9E, while ASC appears diffuse in the cytosol of unstimulated cells (FIG. 9B), upon stimulation with nigericin, ASC staining appears intense and punctate, indicative of inflammasome activation in approximately 20% of cells (FIG. 9E). However, when macrophages are pretreated with BT032, they demonstrate substantially reduced ASC specks in cells (FIGS. 9D and 9E) indicating that BT032 inhibited inflammasome oligomeric formation. Importantly, as ASC-cerulean macrophages do not require priming for activation, this result also demonstrates that BT032 specifically inhibits formation of the oligomeric inflammasome complex and not priming (i.e., NF-κB activation and upregulation of IL-1β and NLRP3).

Accordingly, these results demonstrate that probenecid analogs of the present technology, such as BT032, are useful in methods for inhibiting inflammasome formation and for treating or preventing inflammasome-mediated disease or conditions.

Example 9: Lipopolysaccharide (LPS) Model for NLRP3 Inflammation

This example demonstrates the efficacy of the compounds of the present technology in inhibiting NLRP3 inflammasome activation following acute intraperitoneal (i.p.) challenge with LPS.

Figure 10A:
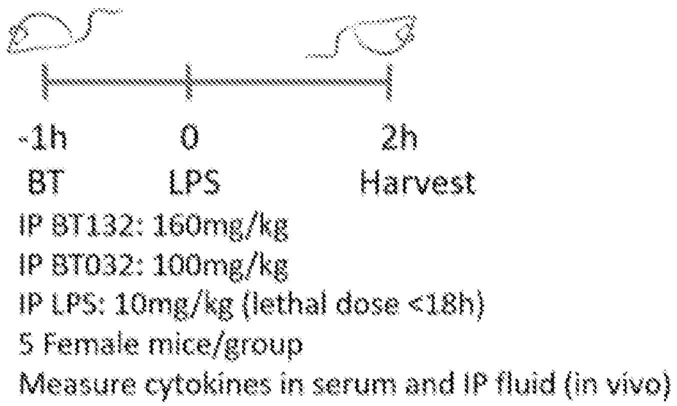
FIG. 10A is a schematic of the mouse IP LPS challenge model for NLRP3 inflammation experiment.

In vivo LPS challenge. As shown in FIG. 10A, female C57BL/6 mice (6-8 weeks old) were injected intraperitoneally (i.p.) with PBS or drug (i.e., BT132 or BT032) in PBS 1 hour before i.p. injection of 10 mg/kg LPS *Escherichia coli* 055:B5 (Sigma Aldrich) or PBS. After 2 hours, the mice were sacrificed and serum and i.p. fluid levels of IL-1β and TNF-α were measured by ELISA.

Figure 10B:
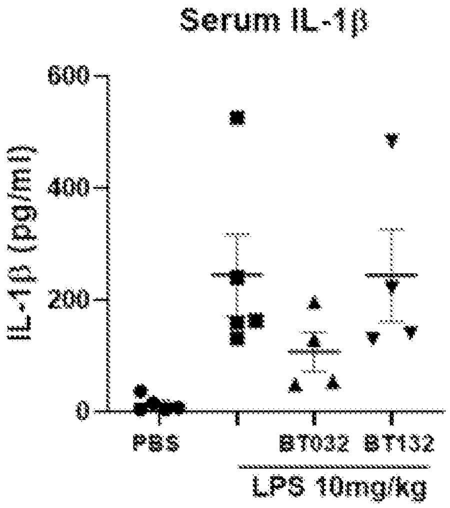
FIG. 10B is a chart showing IL-1β levels (pg/mL) in mouse serum after administration of PBS or LPS (10 mg/kg) intraperitoneally (IP) with or without IP administration of BT032 (100 mg/kg) or BT132 (160 mg/kg) 1 hour prior to LPS administration.
Figure 10C:
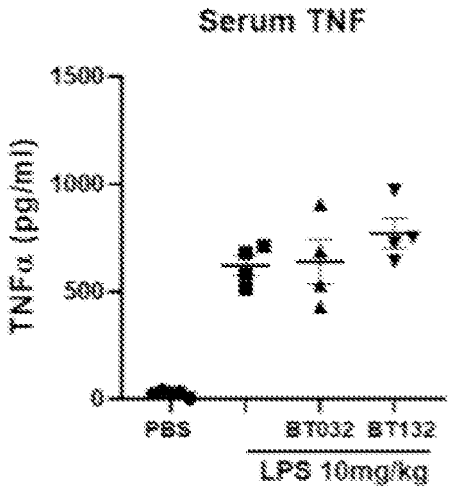
FIG. 10C is a chart showing TNFα levels (pg/mL) in mouse serum after administration of PBS or LPS (10 mg/kg) IP with or without IP administration of BT032 (100 mg/kg) or BT132 (160 mg/kg) 1 hour prior to LPS administration.
Figure 10D:
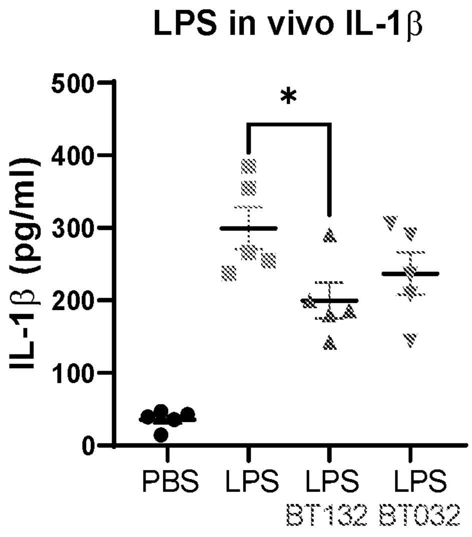
FIG. 10D is a chart showing IL-1β levels (pg/mL) in mouse IP fluid after administration of PBS or LPS (10 mg/kg) intraperitoneally (IP) with or without IP administration of BT032 (100 mg/kg) or BT132 (160 mg/kg) 1 hour prior to LPS administration.
Figure 10E:
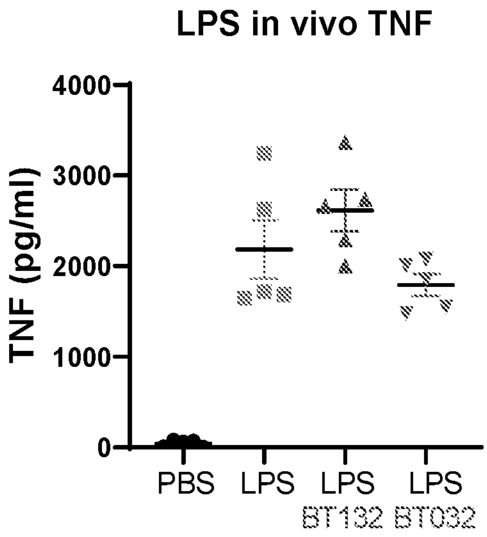
FIG. 10E is a chart showing TNFα levels (pg/mL) in mouse IP fluid after administration of PBS or LPS (10 mg/kg) intraperitoneally (IP) with or without IP administration of BT032 (100 mg/kg) or BT132 (160 mg/kg) 1 hour prior to LPS administration.

Results. Overall, the results show that the probenecid analogs of the present technology are effective in methods for reducing serum and i.p. fluid IL-1β production (FIGS. 10B and 10D). In addition, the results demonstrate that the effect is NLPR3-specific in that serum and i.p. fluid TNF-α levels were not affected (FIGS. 10C and 10E).

Accordingly, these results demonstrate that probenecid analogs of the present technology, such as BT032 and BT132, are useful in methods for inhibiting inflammasome activation and for treating or preventing inflammasome-mediated disease or conditions.

Example 10: Inhibition of NLRP1 Inflammasomes by Probenecid Analogs of the Present Technology This example demonstrates the efficacy of the compounds of the present technology in inhibiting NLRP1 inflammasome activation in vitro, and that the compounds of the present technology exhibit a dose-responsive inhibition of inflammasome activation as assessed by IL-1β secretion.

Figure 11:
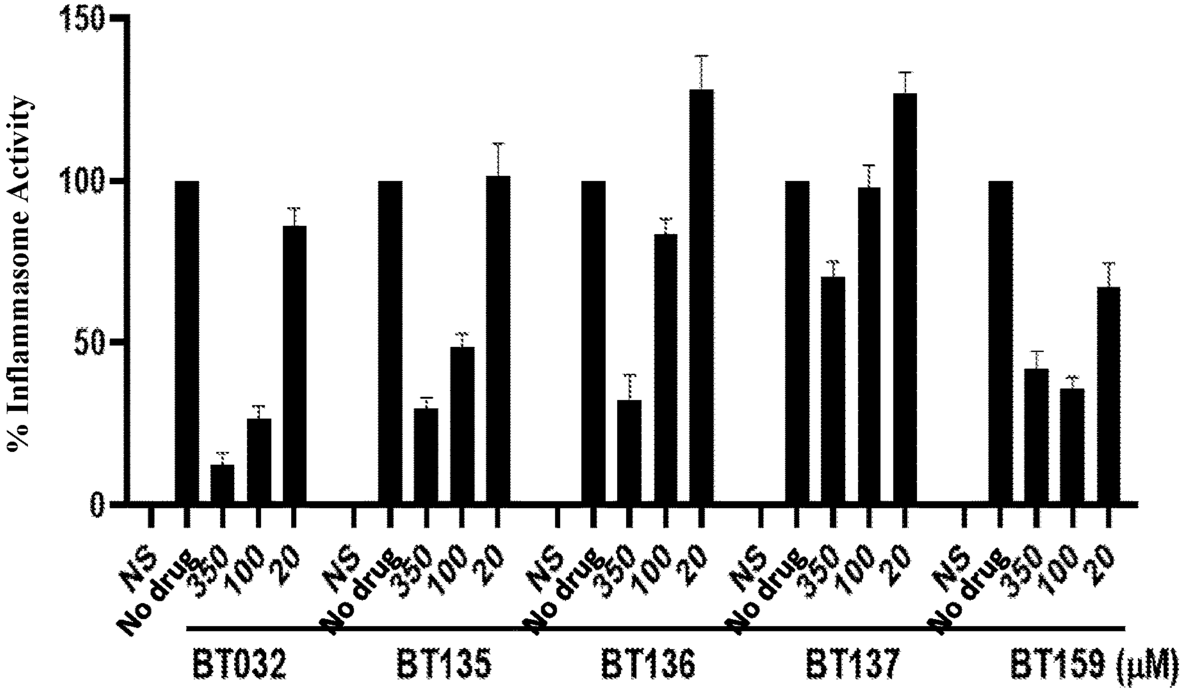
FIG. 11 is a chart showing the effects of treatment of macrophages with BT032, BT135, BT136, BT137, and BT159 (also known as BT052) on NLRP1 (L18-MDP)-induced inflammasome activation. Secreted IL-1β concentrations were measured by ELISA and are represented as the % maximal activation of untreated macrophages ("no drug"). Pooled results of 3 independent experiments were conducted in triplicate where activity was normalized as percentage of activity as related to the DMSO-treated control cells ("no drug") and non-stimulated ("NS") cells.

In vitro stimulation of human macrophages. Immortalized BMDMs grown in DMEM/10% FCS, 2 mM glutamine at 5% CO2 were seeded at $4\times10^4$ cells in 96 well format, 20 h. Macrophages were treated with BT032 (20, 100, 350 μM), BT135 (20, 100, 350 μM), BT136 (20, 100, 350 μM), BT137 (20, 100, 350 μM), or BT159 (also known as BT052) (20, 100, 350 μM) where indicated in serum-free media for 60 mins prior to challenge with NLRP1 agonist, L18-MDP (100 μg/mL; 16 hours) (NS=non-stimulated cells). Cultured supernatants were assayed for secreted IL-1β by ELISA according to manufacturer's instructions and are represented in FIG. 11 as the % maximal activation of untreated macrophages ("no drug"). Pooled results of 3 independent experiments were conducted in triplicate where activity was normalized as percentage of activity as related to the DMSO-treated control cells ("no drug") and non-stimulated (NS) cells.

Results. As shown by FIG. 11, treatment of macrophages with BT032, BT135, BT136, and BT159 (also referred to as BT052 herein) dose-dependently inhibited NLRP1 (L18-MDP)-induced inflammasome activation. These results demonstrate that probenecid analogs of the present technology (e.g., BT032, BT135, BT136, BT159) are NLRP1 inhibitors.

Accordingly, these results demonstrate that probenecid analogs of the present technology, such as BT032, BT135, BT136, BT159, are useful in methods for inhibiting NLRP1 inflammasome activation and for treating or preventing inflammasome-mediated diseases or conditions.

Example 11: Human Microdosing

Human microdosing has been used to safely investigate the pharmacodynamic effects of experimental drugs prior to full Phase 1 studies (Lewis, 2009). Localized dosing of up to 100 μg of drug can be assessed by IV administration as well as by direct instillation to the lung.

Methods. At time 0, an alveolar transbronchial catheter (Knighton, 2018 *J. Med. Dev.*) is used to deliver a microdose (100 μg, 30 μg, 3 μg) of BT032 to a single alveolus to: i) healthy human lungs; ii) healthy human lungs challenged with LPS (50 μg) by inhalation; and iii) lungs of diseased humans (COPD, Acute respiratory distress syndrome (ARDS)). At times 1 h, 4 h, and 8 h, aspirates from the alveolus are withdrawn and immune cells (e.g., macrophages, neutrophils, total cells) and cytokines (e.g., IL-1B, IL-6, IL-18, TNF-alpha, etc.) are assessed. Immune cell quantification is determined by flow cytometry coupled with cell-specific labels. Cytokine levels are determined using standard ELISA assays.

Results. It is anticipated that BT032 will not induce an inflammatory response when microdosed to healthy human lungs, as assessed by immune cell infiltration and cytokine levels. LPS challenge in healthy human lungs is predicted to result in significant infiltration of total cells, neutrophils and macrophages as well as significantly elevated cytokine levels. BT032 administration to LPS-challenged lungs is anticipated to result in a dose-dependent inhibition of immune cell infiltration as well as cytokine induction. Aspirates from COPD and ARDS patients are anticipated to exhibit elevated levels of both immune cell infiltrates and cytokines. Instillation of microdoses of BT032 are anticipated to result in a dose-dependent decrease in these markers of inflammation.

Accordingly, these results will show that compounds of the present technology are useful and effective for the treatment of inflammasome-mediated lung disease or conditions in humans.

Example 12: Probenecid Analogs of the Present Technology for the Prevention and Treatment of Inflammasome-Mediated Lung Disease—AECOPD Model This example will demonstrate the capability of the probenecid analogs of the present technology to reduce inflammasome-mediated disease or conditions and hyperinflammation in vivo during acute exacerbation of chronic obstructive pulmonary disease (AECOPD) in subjects.

Animal Models

Animal models suitable for use in this example include, but are not limited to, animal AECOPD models, such as those described by Chow et al., ((Dec. 20, 2017), Animal Models of Chronic Obstructive Pulmonary Disease, COPD—An Update in Pathogenesis and Clinical Management, Cormac McCarthy, IntechOpen, DOI: 10.5772/intechopen.70262, available from: www.intechopen.com/books/copd-an-update-in-pathogenesis-and-clinical-management/animal-models-of-chronic-obstructive-pulmonary-disease). One of skill in the art will understand that the following description is illustrative and may be applied as appropriate to other animal models.

Quantification of pro-inflammatory cytokines in BAL fluid. To detect cytokines, BAL flued is collected and stored at −80° C. IL-1β is quantified by ELISA. Levels of IL-6, CCL2, IFN-γ, IL-10, IL12p70, MCP-1, and TNF-α proteins are determined by cytokine bead array and mouse inflammation kit (Becton Dickinson).

Recovery and characterization of leukocytes from mice. For flow cytometric analysis, BAL cells are treated with red blood cell lysis buffer (Sigma Aldrich), and cell numbers and viability are assessed via trypan blue exclusion using a hemocytometer. BAL cells are incubated with Fc block, followed by staining with fluorochrome-conjugated monoclonal antibodies to Ly6C, Ly6G, CD11c, and I-$A^b$ (BD Biosciences, USA). Neutrophils ($Ly6G^+$), airway macrophages ($CD11c^+$ I-$A^{b\ high}$), inflammatory macrophages ($Ly6G^-$ $Ly6C^+$) are quantified by flow cytometry, as described in Tate et al., *Scientific Reports* 6, 27912 (2016). Live cells (propidium iodide negative) are analyzed using a flow cytometer. Total cell counts are calculated from viable cell counts performed via trypan blue exclusion.

Results. It is expected that intranasal treatment of mice with the probenecid analogs of the present technology will reduce clinical signs of disease and prolong the survival of mice. In addition, it is expected that the treatment groups will exhibit reduced biomarkers of excessive pulmonary inflammation and cellular infiltrates, including reduced total numbers of cellular infiltrates in the airways, such as alveolar macrophages, neutrophils, inflammatory $Ly6C^+$ macrophages, and dendritic cells (DCs), and that levels of IL-1β production and hyperinflammation in the airways will be reduced.

Accordingly, these results will show that the probenecid analogs of the present technology are effective in methods for treating inflammasome-mediated lung disease, for example, in AECOPD.

Human Subjects

Human subjects diagnosed as having or suspected to have an inflammasome-mediated lung disease or condition or a related disorder and presently displaying one or more symptoms and/or pathologies of inflammasome-mediated lung disease or condition or a related disorder, such as AECOPD, are recruited using selection criteria known and accepted in the art.

Methods of Prevention and Treatment: Subjects are administered probenecid analogs of the present technology at a dosage and frequency commensurate with the stage and severity of disease. In some embodiments a compound is administered once daily, once weekly, or once monthly. In some embodiments, a compound is administered multiple times daily, weekly, or monthly. In some embodiments, the probenecid analogs of the present technology are formulated for intra-alveolar administration.

To demonstrate methods of prevention and treatment in humans, subjects are administered probenecid analogs of the present technology prior to or subsequent to the development of symptoms and/or pathologies of inflammasome-mediated lung disease or condition (e.g., AECOPD) or related disorders and assessed for reversal of symptoms/pathologies or attenuation of expected symptoms/pathologies using methods known in the art.

Results: It is expected that the probenecid analogs of the present technology will induce reversal of symptoms and/or pathologies of inflammasome-mediated lung disease or condition (e.g., AECOPD) and related disorders in human subjects. These results will show that compounds of the present technology are useful and effective for the prevention and treatment of such disorders.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

Each and every publication and patent mentioned in the above specification is herein incorporated by reference in its entirety for all purposes. Various modifications and variations of the described methods and system of the present technology will be apparent to those skilled in the art without departing from the scope and spirit of the present technology. Although the present technology has been described in connection with specific embodiments, the present technology as claimed should not be unduly limited to such specific embodiments. Indeed, various modifications of the described modes for carrying out the present technology which are obvious to those skilled in the art and in fields related thereto are intended to be within the scope of the following claims.

What is claimed is:

1. A compound having the structure of Formula I,

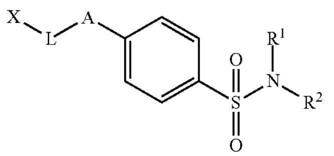

I tautomers thereof and/or pharmaceutically acceptable salts thereof; wherein

A is $C(O)N(R^3)$, phenylene, oxazolylene, thiazolylene, piperidinylene, or

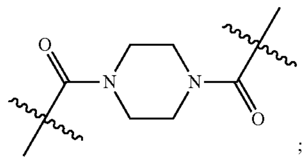 [SMILES: *C(=O)N1CCN(C(*)=O)CC1]

;

L is $C_{3-10}$ alkylene;

X is CHO, COOH, $C(O)NR^4R^5$, $COOR^6$, $NH_2$ or NHR;

R is 2-chloropyrimidin-4-yl;

$R^1$ and $R^2$ are independently a substituted or unsubstituted $C_{1-6}$ alkyl group, or one of $R^1$ and $R^2$ is H, and the other is cyclohexyl-NH—C(O), or $R^1$ and $R^2$ together are a $C_{4-6}$ alkylene group and form a 5-, 6-, or 7-member ring with the nitrogen to which they are attached, said ring optionally substituted with a phenyl group;

$R^3$ and $R^4$ are independently selected from H or a $C_{1-6}$ alkyl group;

$R^5$ is selected from H, PEG, or a $C_{1-6}$ alkyl group; and $R^6$ is selected from a substituted or unsubstituted $C_{1-10}$ alkyl, $C_{2-10}$ alkenyl, or $C_{7-14}$ aralkyl group.

2. The compound of claim 1, wherein A is $C(O)N(R^3)$.

3. The compound of claim 2, wherein $R^3$ is H or methyl.

4. The compound of claim 1, wherein A is phenylene, oxazolylene, thiazolylene, piperidinylene or

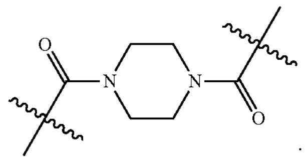 [SMILES: *C(=O)N1CCN(C(*)=O)CC1]

.

5. The compound of claim 1, wherein A is phenylene, oxazolylene, thiazolylene, or piperidinylene.

6. The compound of claim 1, wherein X is CHO, COOH, $C(O)NR^4R^5$, $NH_2$ or NHR.

7. The compound of claim 1, wherein X is COOH.

8. The compound of claim 1, wherein X is $COOR^6$.

9. The compound of claim 1, wherein X is $C(O)NR^4R^5$.

10. The compound of claim 1, wherein X is $NH_2$ or NHR.

11. The compound of claim 1, wherein each of $R^1$ and $R^2$ is independently a $C_{1-6}$ alkyl, optionally substituted with one or more F, OH, $CF_3$, $C_{3-7}$ cycloalkyl group or $SO_2$-alkyl.

12. The compound of claim 1, wherein $R^1$ and $R^2$ together are a $C_{3-5}$ alkylene group and form a 5-, 6-, or 7-member ring with the nitrogen to which they are attached.

13. The compound of claim 1, wherein one of $R^1$ and $R^2$ is H, and the other is cyclohexyl-NH—C(O).

14. The compound of claim 1, wherein

A is $C(O)N(R^3)$, phenylene, oxazolylene, thiazolylene, or piperidinylene;

L is $C_{3-10}$ alkylene;

X is COOH or $NH_2$;

$R^1$ and $R^2$ are independently a substituted or unsubstituted $C_{1-6}$ alkyl group; and $R^3$ is selected from H or a $C_{1-6}$ alkyl group.

15. The compound of claim 14, wherein A is phenylene, oxazolylene, thiazolylene, or piperidinylene, and L is $C_{3-5}$ alkylene.

16. The compound of claim 1, wherein the compound is

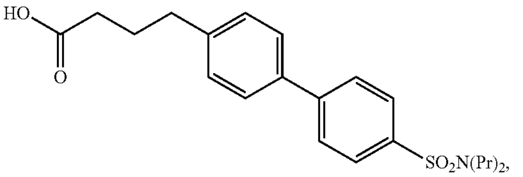

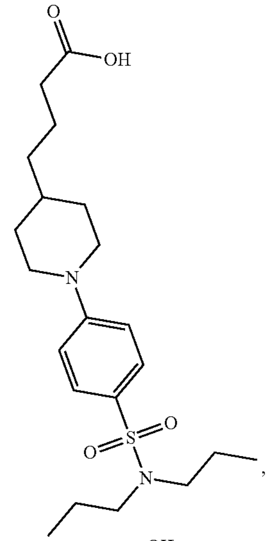

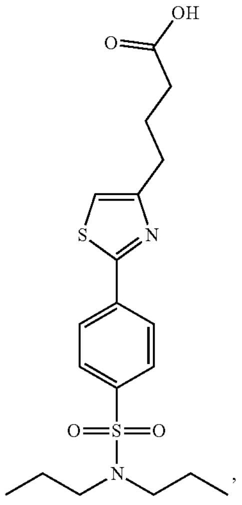

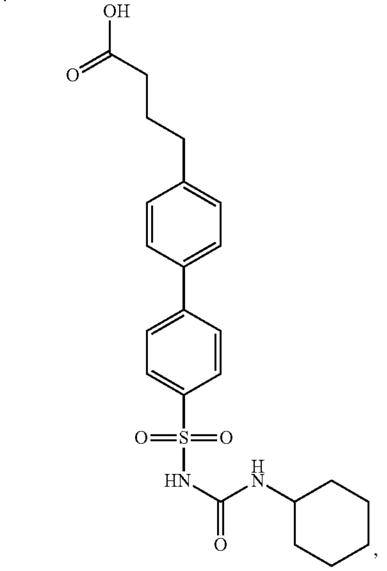

-continued

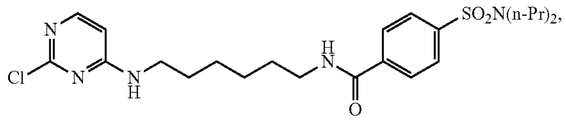

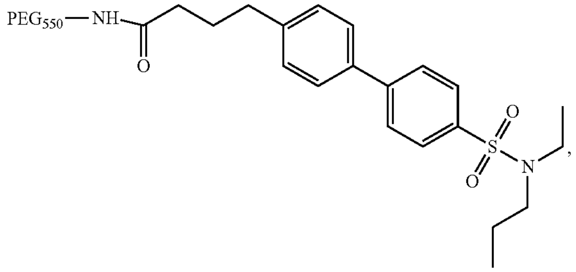

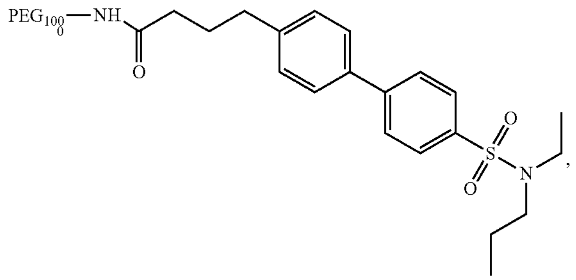

or a pharmaceutically acceptable salt thereof.

17. A pharmaceutical composition comprising a compound, tautomer thereof, and/or pharmaceutically acceptable salt of claim 1 and a pharmaceutically acceptable carrier.

18. A method for treating or preventing an inflammasome-mediated disease or condition in a mammalian subject in need thereof, comprising administering to the subject a therapeutically effective amount of a compound, tautomer thereof, and/or pharmaceutically acceptable salt of claim 1.

19. The method of claim 18, wherein the inflammasome-mediated disease or condition is associated with NLRP1 inflammasome activation and/or NLRP3 inflammasome activation.

20. The method of claim 18, wherein the inflammasome-mediated disease or condition is an inflammasome-mediated lung disease or condition.

21. The method of claim 18, wherein the compound, tautomer thereof, and/or pharmaceutically acceptable salt is selected from the group consisting of

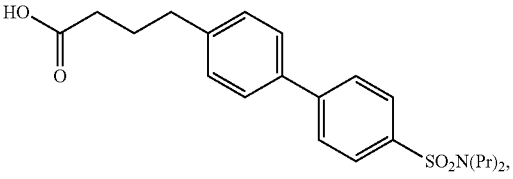

-continued

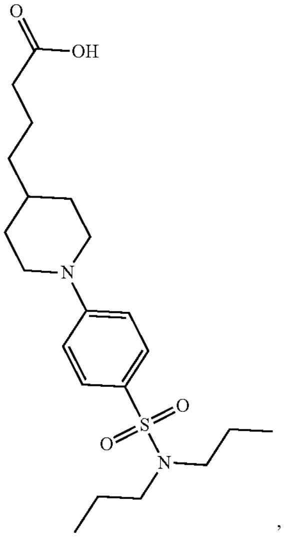

,

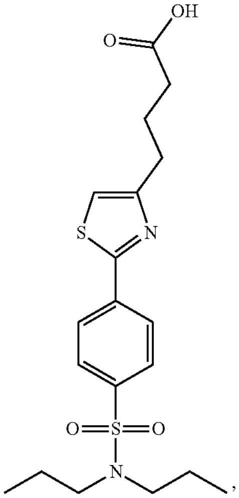

,

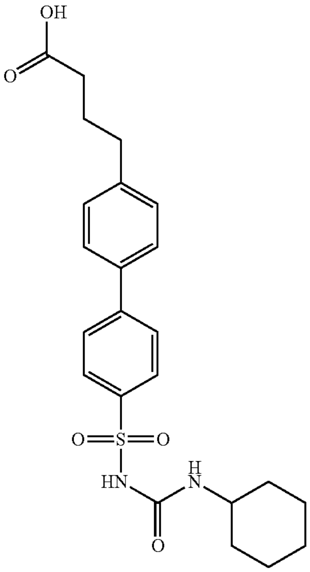

,

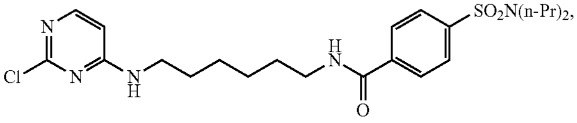

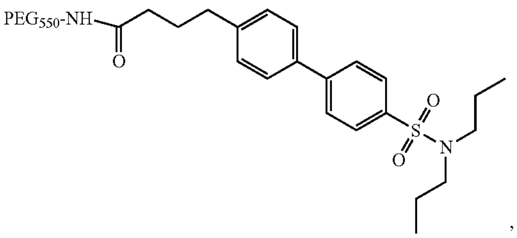

, and

-continued

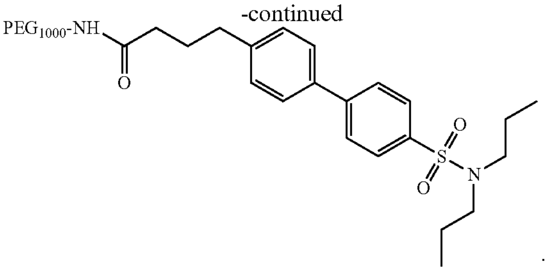

.

22. The method of claim 20, wherein the inflammasome-mediated lung disease or condition is/is caused by a pathogen selected from the group consisting of: pandemic influenza; *Streptococcus pneumonia; Pseudomonas aeruginosa, Mycobacterium tuberculosis*; respiratory syndromes caused by rhinovirus, Flaviviruses, Dengue virus, Zika virus, or West Nile virus; idiopathic pulmonary fibrosis (IPF); chronic obstructive pulmonary disease (COPD); acute exacerbations of COPD (AECOPD); asthma; acute respiratory distress syndrome (ARDS); COVID-19; Middle East Respiratory Syndrome (MERS); Severe Acute Respiratory Syndrome (SARS); silicosis; and asbestosis; or the inflammasome-mediated lung disease or condition is associated with inhalation of an irritant.

23. The method of claim 22, wherein the inhaled irritant comprises a gas, a mist, a fume, a dust, silica, asbestos, smoke, cigarette smoke, or nanoparticles.

24. The method of claim 18, wherein the administering step is selected from the group consisting of intranasal administration, intramuscular administration, subcutaneous administration, administration by inhalation, and oral administration.

25. The method of claim 18, wherein the treating or preventing inflammasome-mediated disease or condition comprises reducing the level of one or more inflammatory cytokines in the subject as compared to an untreated control subject, wherein the one or more inflammatory cytokines is selected from the group consisting of IL-1β, IL-18, IL-1α, IL-6, IL-33, TNF-α, CCL2, IFN-γ, IL-10, IL12p70, MCP-1, HMGB1, and any combination thereof.

26. The method of claim 20, wherein the treating or preventing inflammasome-mediated lung disease or condition comprises reducing cellular infiltrate levels in the lungs of the subject as compared to an untreated control subject, wherein the cellular infiltrates comprise one or more of alveolar macrophages, neutrophils, inflammatory $Ly6C^+$ macrophages, and dendritic cells.

27. The method of claim 18, wherein the treating or preventing inflammasome-mediated disease or condition comprises reducing apoptosis-associated speck-like protein containing a caspase activating and recruitment domain (ASC) speck formation in the subject as compared to an untreated control subject.

28. The compound of claim 1, wherein the compound is

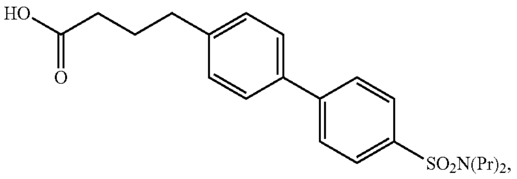

a tautomer thereof, and/or pharmaceutically acceptable salt thereof.
29. The method of claim 18, wherein the compound is
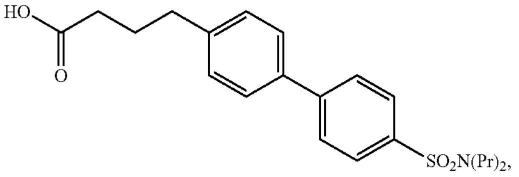
a tautomer thereof, and/or pharmaceutically acceptable salt thereof.
* * * * *